US011382653B2

(12) United States Patent
Patel et al.

(10) Patent No.: US 11,382,653 B2
(45) Date of Patent: *Jul. 12, 2022

(54) ATHERECTOMY CATHETER

(71) Applicant: Avinger, Inc., Redwood City, CA (US)

(72) Inventors: Himanshu N. Patel, San Jose, CA (US); John B. Simpson, Woodside, CA (US); Charles W. McNall, Cottonwood Heights, UT (US); Maegan K. Spencer, Emerald Hills, CA (US); Michael Zung, San Carlos, CA (US); Priyanshu Gupta, Hornsby (AU); Nicholas J. Spinelli, San Carlos, CA (US); Myra L. Fabro, San Jose, CA (US); Eduardo Sucgang, South San Francisco, CA (US); Theodore W. Ketai, San Francisco, CA (US)

(73) Assignee: Avinger, Inc., Redwood City, CA (US)

( * ) Notice: Subject to any disclaimer, the term of this patent is extended or adjusted under 35 U.S.C. 154(b) by 193 days.

This patent is subject to a terminal disclaimer.

(21) Appl. No.: 16/460,903

(22) Filed: Jul. 2, 2019

(65) Prior Publication Data

US 2020/0060718 A1    Feb. 27, 2020

Related U.S. Application Data

(63) Continuation-in-part of application No. 15/162,330, filed on May 23, 2016, now Pat. No. 10,349,974, and (Continued)

(51) Int. Cl.
*A61B 17/3207* (2006.01)
*A61B 1/00* (2006.01)
(Continued)

(52) U.S. Cl.
CPC .. *A61B 17/320783* (2013.01); *A61B 1/00179* (2013.01); *A61B 1/00183* (2013.01);
(Continued)

(58) Field of Classification Search
CPC .... A61B 17/320783; A61B 17/320725; A61B 17/320758; A61B 1/00179;
(Continued)

(56) References Cited

U.S. PATENT DOCUMENTS 3,367,727 A    2/1968   Ward et al.
3,908,637 A    9/1975   Doroshow
(Continued)

FOREIGN PATENT DOCUMENTS

CN    1875242 A    12/2006
CN    1947652 A    4/2007
(Continued)

OTHER PUBLICATIONS

Stamper et al.; Plaque characterization with optical coherence tomography. Journal of the American College of Cardiology. 47(8); pp. 69-79; Apr. 18, 2006.
(Continued)

*Primary Examiner* — Sarah A Simpson
(74) *Attorney, Agent, or Firm* — Shay Glenn LLP

(57) ABSTRACT

Described herein are atherectomy catheters, systems and methods that include longitudinally displaceable drive shafts that drive actuation of one or more cutters at the distal end of the catheter. The catheters described herein may include one or more imaging sensors for imaging before, during or after cutting tissue. In some variations the imaging sensor may be rotated around the perimeter of the catheter independently of the rotation of the cutter. Also describe herein are imaging catheters that may be used without cutters.

10 Claims, 80 Drawing Sheets

Related U.S. Application Data a continuation-in-part of application No. 14/424,266, filed as application No. PCT/US2013/032196 on Mar. 15, 2013, now Pat. No. 10,335,173, and a continuation-in-part of application No. 13/654,357, filed on Oct. 17, 2012, now Pat. No. 10,363,062, said application No. 15/162,330 is a continuation of application No. 13/175,232, filed on Jul. 1, 2011, now Pat. No. 9,345,510.

(60) Provisional application No. 61/697,726, filed on Sep. 6, 2012, provisional application No. 61/646,843, filed on May 14, 2012, provisional application No. 61/548,179, filed on Oct. 17, 2011, provisional application No. 61/492,693, filed on Jun. 2, 2011, provisional application No. 61/468,396, filed on Mar. 28, 2011, provisional application No. 61/360,886, filed on Jul. 1, 2010.

(51) Int. Cl.
*A61B 1/313* (2006.01)
*A61B 90/00* (2016.01)
*A61B 5/00* (2006.01)
*A61B 17/00* (2006.01)

(52) U.S. Cl.
CPC .... *A61B 1/3137* (2013.01); *A61B 17/320725* (2013.01); *A61B 17/320758* (2013.01); *A61B 1/00165* (2013.01); *A61B 5/0066* (2013.01); *A61B 90/37* (2016.02); *A61B 2017/00292* (2013.01); *A61B 2017/320791* (2013.01); *A61B 2090/3614* (2016.02); *A61B 2090/3735* (2016.02)

(58) Field of Classification Search
CPC .............. A61B 1/00183; A61B 1/3137; A61B 2017/320791; A61B 1/00165
See application file for complete search history.

(56) References Cited

U.S. PATENT DOCUMENTS

| | | |
|---|---|---|
| 4,178,935 A | 12/1979 | Gekhaman et al. |
| 4,487,206 A | 12/1984 | Aagard |
| 4,527,553 A | 7/1985 | Upsher |
| 4,552,554 A | 11/1985 | Gould et al. |
| 4,578,061 A | 3/1986 | Lemelson |
| 4,611,600 A | 9/1986 | Cohen |
| 4,621,353 A | 11/1986 | Hazel et al. |
| 4,639,091 A | 1/1987 | Huignard et al. |
| 4,651,753 A | 3/1987 | Lifton |
| 4,654,024 A | 3/1987 | Crittenden et al. |
| 4,681,106 A | 7/1987 | Kensey et al. |
| 4,686,982 A | 8/1987 | Nash |
| 4,691,708 A | 9/1987 | Kane |
| 4,729,763 A | 3/1988 | Henrie |
| 4,771,774 A | 9/1988 | Simpson et al. |
| 4,781,186 A | 11/1988 | Simpson et al. |
| 4,841,977 A | 6/1989 | Griffith et al. |
| 4,857,046 A | 8/1989 | Stevens et al. |
| 4,920,961 A | 5/1990 | Grossi et al. |
| 4,926,858 A | 5/1990 | Gifford, III et al. |
| 5,000,185 A | 3/1991 | Yock |
| 5,018,529 A | 5/1991 | Tenerz et al. |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,372,601 A | 12/1994 | Lary |
| 5,383,460 A | 1/1995 | Jang et al. |
| 5,383,467 A | 1/1995 | Auer et al. |
| 5,425,273 A | 6/1995 | Chevalier |
| 5,429,136 A | 7/1995 | Milo et al. |
| 5,431,673 A | 7/1995 | Summers et al. |
| 5,437,284 A | 8/1995 | Trimble |
| 5,459,570 A | 10/1995 | Swanson et al. |
| 5,460,168 A | 10/1995 | Masubuchi et al. |
| 5,465,147 A | 11/1995 | Swanson |
| 5,507,725 A | 4/1996 | Savage et al. |
| 5,507,760 A | 4/1996 | Wynne et al. |
| 5,507,795 A | 4/1996 | Chiang et al. |
| 5,517,998 A | 5/1996 | Madison |
| 5,556,405 A | 9/1996 | Lary |
| 5,607,394 A | 3/1997 | Andersen et al. |
| 5,620,426 A | 4/1997 | Braithwaite |
| 5,632,754 A | 5/1997 | Farley et al. |
| 5,632,755 A | 5/1997 | Nordgren et al. |
| 5,674,232 A | 10/1997 | Halliburton |
| 5,681,336 A | 10/1997 | Clement et al. |
| 5,690,634 A | 11/1997 | Muller et al. |
| 5,722,403 A | 3/1998 | McGee et al. |
| 5,728,148 A | 3/1998 | Bostrom et al. |
| 5,749,846 A | 5/1998 | Edwards et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,843,103 A | 12/1998 | Wulfman |
| 5,851,212 A | 12/1998 | Zirps et al. |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,938,602 A | 8/1999 | Lloyd |
| 5,938,671 A | 8/1999 | Katoh et al. |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,285,903 B1 | 9/2001 | Rosenthal et al. |

(56) References Cited

U.S. PATENT DOCUMENTS

| | | |
|---|---|---|
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,375,615 B1 | 4/2002 | Flaherty et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,216 B1 | 11/2002 | Hiblar et al. |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,544,230 B1 | 4/2003 | Flaherty et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,599,296 B1 | 7/2003 | Gillick et al. |
| 6,615,071 B1 | 9/2003 | Casscells, III et al. |
| 6,629,953 B1 | 10/2003 | Boyd |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,002,763 B2 | 8/2011 | Berthiaume |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,647,335 B2 | 2/2014 | Markus |
| 8,696,695 B2 | 4/2014 | Patel et al. |
| 8,911,459 B2 | 12/2014 | Simpson et al. |
| 9,119,662 B2 | 9/2015 | Moberg |
| 9,125,562 B2 | 9/2015 | Spencer et al. |
| 9,333,007 B2 | 5/2016 | Escudero et al. |
| 9,345,398 B2 | 5/2016 | Tachibana et al. |
| 9,345,406 B2 | 5/2016 | Spencer et al. |
| 9,345,510 B2 * | 5/2016 | Patel .................. A61B 1/00179 |
| 9,345,511 B2 | 5/2016 | Smith et al. |
| 9,351,757 B2 | 5/2016 | Kusleika |
| 9,498,247 B2 | 11/2016 | Patel et al. |
| 9,498,600 B2 | 11/2016 | Rosenthal et al. |
| 9,557,156 B2 | 1/2017 | Kankaria |
| 9,572,492 B2 | 2/2017 | Simpson et al. |
| 9,579,157 B2 | 2/2017 | Moberg |
| 9,592,075 B2 | 3/2017 | Simpson et al. |
| 9,642,646 B2 | 5/2017 | Patel et al. |
| 9,788,790 B2 | 10/2017 | Black et al. |
| 9,854,979 B2 | 1/2018 | Smith et al. |
| 9,918,734 B2 | 3/2018 | Patel et al. |
| 9,949,754 B2 | 4/2018 | Newhauser et al. |
| 10,052,125 B2 | 8/2018 | Rosenthal et al. |
| 10,130,386 B2 | 11/2018 | Simpson et al. |
| 10,213,224 B2 | 2/2019 | Guggenheimer et al. |
| 10,244,934 B2 | 4/2019 | Tachibana et al. |
| 10,314,667 B2 | 6/2019 | Garvey et al. |
| 10,335,173 B2 | 7/2019 | Carver et al. |
| 10,342,491 B2 | 7/2019 | Black et al. |
| 10,349,974 B2 * | 7/2019 | Patel .................. A61B 1/00179 |
| 10,357,277 B2 | 7/2019 | Patel et al. |
| 10,363,062 B2 | 7/2019 | Spencer et al. |
| 10,406,316 B2 | 9/2019 | Garvey et al. |
| 2001/0005788 A1 | 6/2001 | McGuckin, Jr. |
| 2001/0020126 A1 | 9/2001 | Swanson et al. |

(56) References Cited

U.S. PATENT DOCUMENTS

| | | |
|---|---|---|
| 2002/0019644 A1 | 2/2002 | Hastings et al. |
| 2002/0072706 A1 | 6/2002 | Hiblar et al. |
| 2002/0082585 A1 | 6/2002 | Carroll et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0139751 A1 | 7/2003 | Evans et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1* | 8/2004 | Simpson ............... A61B 1/05 606/159 |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0193140 A1 | 9/2004 | Griffin et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0027199 A1 | 2/2005 | Clarke |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0197623 A1 | 9/2005 | Leeflang et al. |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0011820 A1 | 1/2006 | Chow-Shing et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0050019 A1 | 3/2007 | Hyde |
| 2007/0078469 A1 | 4/2007 | Soito et al. |
| 2007/0078500 A1 | 4/2007 | Ryan et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0167710 A1 | 7/2007 | Unal et al. |
| 2007/0196926 A1 | 8/2007 | Soito et al. |
| 2007/0213618 A1 | 9/2007 | Li et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0015618 A1 | 1/2008 | Sonnenschein et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0095421 A1 | 4/2008 | Sun et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0132929 A1 | 6/2008 | O'Sullivan et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0154296 A1 | 6/2008 | Taylor et al. |
| 2008/0177138 A1 | 7/2008 | Courtney et al. |
| 2008/0186501 A1 | 8/2008 | Xie |
| 2008/0207996 A1 | 8/2008 | Tsai |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0043191 A1 | 2/2009 | Castella et al. |
| 2009/0073444 A1 | 3/2009 | Wang |

(56) References Cited

U.S. PATENT DOCUMENTS

| | | |
|---|---|---|
| 2009/0076447 A1 | 3/2009 | Casas et al. |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0004544 A1 | 1/2010 | Toida |
| 2010/0021926 A1 | 1/2010 | Noordin |
| 2010/0049225 A1 | 2/2010 | To et al. |
| 2010/0080016 A1 | 4/2010 | Fukui et al. |
| 2010/0082000 A1 | 4/2010 | Honeck et al. |
| 2010/0125253 A1 | 5/2010 | Olson |
| 2010/0130996 A1 | 5/2010 | Doud et al. |
| 2010/0217245 A1 | 8/2010 | Prescott |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0312263 A1 | 12/2010 | Moberg et al. |
| 2010/0317973 A1 | 12/2010 | Nita |
| 2010/0324472 A1 | 12/2010 | Wulfman |
| 2011/0023617 A1 | 2/2011 | Yu et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0208222 A1 | 8/2011 | Ljahnicky et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |
| 2012/0123352 A1 | 5/2012 | Fruland et al. |
| 2012/0136350 A1 | 5/2012 | Goshgarian et al. |
| 2012/0238869 A1 | 9/2012 | Schmitt et al. |
| 2012/0259337 A1 | 10/2012 | del Rio et al. |
| 2012/0277730 A1 | 11/2012 | Salahieh et al. |
| 2012/0289971 A1 | 11/2012 | Segermark et al. |
| 2013/0035692 A1 | 2/2013 | Sorensen et al. |
| 2013/0065124 A1 | 3/2013 | Morishima et al. |
| 2013/0072787 A1 | 3/2013 | Wallace et al. |
| 2013/0184549 A1 | 7/2013 | Avitall et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0287282 A1 | 10/2013 | Yokota |
| 2013/0296695 A1 | 11/2013 | Spencer et al. |
| 2013/0317519 A1 | 11/2013 | Romo et al. |
| 2013/0325003 A1 | 12/2013 | Kapur et al. |
| 2013/0331819 A1 | 12/2013 | Rosenman et al. |
| 2014/0005534 A1 | 1/2014 | He et al. |
| 2014/0046250 A1 | 2/2014 | Jain et al. |
| 2014/0128893 A1 | 5/2014 | Guggenheimer et al. |
| 2014/0187949 A1 | 7/2014 | Zhao et al. |
| 2014/0222042 A1 | 8/2014 | Kessler |
| 2014/0222047 A1 | 8/2014 | Vreeman |
| 2014/0275996 A1 | 9/2014 | Stigall |
| 2014/0291985 A1 | 10/2014 | Cabrera et al. |
| 2014/0343410 A1 | 11/2014 | Graf et al. |
| 2014/0371718 A1 | 12/2014 | Alvarez et al. |
| 2015/0025310 A1 | 1/2015 | Everingham et al. |
| 2015/0036146 A1 | 2/2015 | Staloff |
| 2015/0141816 A1 | 5/2015 | Gupta et al. |
| 2015/0146211 A1 | 5/2015 | Bhagavatula et al. |
| 2015/0320975 A1 | 11/2015 | Simpson et al. |
| 2016/0008025 A1 | 1/2016 | Gupta et al. |
| 2016/0038030 A1 | 2/2016 | Smith et al. |
| 2016/0144155 A1 | 5/2016 | Simpson et al. |
| 2016/0262839 A1 | 9/2016 | Spencer et al. |
| 2016/0310700 A1 | 10/2016 | Drake et al. |
| 2016/0354109 A1 | 12/2016 | Guggenheimer et al. |
| 2016/0354110 A1 | 12/2016 | Guggenheimer et al. |
| 2017/0065295 A1 | 3/2017 | Patel et al. |
| 2017/0172666 A1 | 6/2017 | Govar et al. |
| 2017/0238803 A1 | 8/2017 | Kankaria |
| 2017/0238808 A1 | 8/2017 | Simpson et al. |
| 2017/0273711 A1 | 9/2017 | Simpson et al. |
| 2018/0042520 A1 | 2/2018 | Patel et al. |
| 2018/0192880 A1 | 7/2018 | Patel et al. |
| 2018/0200488 A1 | 7/2018 | Drake et al. |
| 2018/0207417 A1 | 7/2018 | Zung et al. |
| 2018/0256039 A1 | 9/2018 | Smith et al. |
| 2018/0256187 A1 | 9/2018 | Patel et al. |
| 2018/0364024 A1 | 12/2018 | Baca et al. |
| 2018/0368688 A9 | 12/2018 | Simpson et al. |
| 2019/0021679 A1 | 1/2019 | Christensen |
| 2019/0021760 A1 | 1/2019 | Newhauser et al. |
| 2019/0029714 A1 | 1/2019 | Patel et al. |
| 2019/0110809 A1 | 4/2019 | Rosenthal et al. |
| 2019/0159796 A1 | 5/2019 | Simpson et al. |
| 2019/0209206 A1 | 7/2019 | Patel et al. |

FOREIGN PATENT DOCUMENTS

| | | |
|---|---|---|
| CN | 101601581 A | 12/2009 |
| CN | 103027727 A | 4/2013 |
| CN | 104968285 A | 10/2015 |
| DE | 202006018883.5 U | 2/2007 |
| EP | 0347098 A2 | 12/1989 |
| EP | 0808638 A1 | 11/1997 |
| EP | 0845692 B1 | 11/2005 |
| EP | 1859732 A1 | 11/2007 |
| EP | 2090245 A1 | 8/2009 |
| EP | 2353526 B1 | 9/2013 |
| EP | 2942028 A1 | 11/2015 |
| JP | S62-275425 A | 11/1987 |
| JP | 03502060 A | 2/1990 |
| JP | 05103763 A | 4/1993 |
| JP | 06027343 A | 2/1994 |
| JP | H07184888 A | 7/1995 |
| JP | 07308393 A | 11/1995 |
| JP | 2002214127 A | 7/2002 |
| JP | 2004509695 A | 4/2004 |
| JP | 2004516073 A | 6/2004 |
| JP | 2005114473 A | 4/2005 |
| JP | 2005230550 A | 9/2005 |
| JP | 2005249704 A | 9/2005 |
| JP | 2005533533 A | 11/2005 |
| JP | 2008175698 A | 7/2006 |
| JP | 2006288775 A | 10/2006 |
| JP | 2006313158 A | 11/2006 |
| JP | 2006526790 A | 11/2006 |
| JP | 2006326157 A | 12/2006 |
| JP | 200783053 A | 4/2007 |
| JP | 200783057 A | 4/2007 |

(56) References Cited

FOREIGN PATENT DOCUMENTS

| | | | |
|---|---|---|---|
| JP | 2007225349 A | 9/2007 |
| JP | 2007533361 A | 11/2007 |
| JP | 2008023627 | 2/2008 |
| JP | 2008128708 A | 6/2008 |
| JP | 2008145376 A | 6/2008 |
| JP | 2008183208 A | 8/2008 |
| JP | 2008253492 A | 10/2008 |
| JP | 200914751 A | 1/2009 |
| JP | 2009509690 A | 3/2009 |
| JP | 200978150 A | 4/2009 |
| JP | 2009066252 A | 4/2009 |
| JP | 2009201969 A | 9/2009 |
| JP | 2010042182 A | 2/2010 |
| JP | 2010518900 A | 6/2010 |
| JP | 2011521747 A | 7/2011 |
| JP | 2012143558 A | 8/2012 |
| JP | 2012229976 A | 11/2012 |
| JP | 2012533353 A | 12/2012 |
| JP | 2013512736 A | 4/2013 |
| JP | 2013/524930 A | 6/2013 |
| JP | 2015533584 A | 11/2015 |
| JP | 2016508758 A | 3/2016 |
| KR | 2007/0047221 A | 5/2007 |
| RU | 2185859 C2 | 7/2002 |
| RU | 2218191 C2 | 12/2003 |
| WO | WO91/17698 A1 | 11/1991 |
| WO | WO99/23958 A1 | 5/1999 |
| WO | WO00/54659 A1 | 9/2000 |
| WO | WO01/15609 A1 | 3/2001 |
| WO | WO01/76680 A1 | 10/2001 |
| WO | WO2006/133030 A2 | 12/2006 |
| WO | WO2008/005888 A2 | 1/2008 |
| WO | WO2008/029506 A1 | 3/2008 |
| WO | WO2008/042987 A2 | 4/2008 |
| WO | WO2008/051951 A1 | 5/2008 |
| WO | WO2008/065600 A2 | 6/2008 |
| WO | WO2008/086613 A1 | 7/2008 |
| WO | WO2008/087613 A2 | 7/2008 |
| WO | WO2009/005779 A1 | 1/2009 |
| WO | WO2009/006335 A1 | 1/2009 |
| WO | WO2009/009799 A1 | 1/2009 |
| WO | WO2009/009802 A1 | 1/2009 |
| WO | WO2009/023635 A1 | 2/2009 |
| WO | WO2009/024344 A1 | 2/2009 |
| WO | WO2009/094341 A2 | 7/2009 |
| WO | WO2009/140617 A2 | 11/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |
| WO | WO2011/062087 A1 | 5/2011 |
| WO | WO2012/057940 A1 | 5/2012 |
| WO | WO2012/061935 A1 | 5/2012 |
| WO | WO2012/123737 A1 | 9/2012 |
| WO | WO2012/166332 A1 | 12/2012 |
| WO | WO2013/033490 A1 | 3/2013 |
| WO | WO2013/056262 A1 | 4/2013 |
| WO | WO2014/077870 A1 | 5/2014 |
| WO | WO2014/093148 A2 | 6/2014 |
| WO | WO2015/074018 A1 | 5/2015 |
| WO | WO2015/101747 A1 | 7/2015 |
| WO | WO2015/120146 A1 | 8/2015 |
| WO | WO2015/165736 A1 | 11/2015 |
| WO | WO2017/007853 A1 | 1/2017 |
| WO | WO2017/132247 A1 | 8/2017 |
| WO | WO2017/161166 A1 | 9/2017 |
| WO | WO2018/094041 A1 | 5/2018 |
| WO | WO2019/204797 A1 | 10/2019 |

OTHER PUBLICATIONS

Black et al; U.S. Appl. No. 16/506,851 entitled "Optical coherence tomography for biological imaging," filed Jul. 9, 2019.

Patel et al.; U.S. Appl. No. 16/516,093 entitled "High speed chronic total occlusion crossing devices," filed Jul. 18, 2019.

Patel et al.; U.S. Appl. No. 16/681,807 entitled "Atherectomy catheters and occlusion crossing devices," filed Nov. 12, 2019.

Bayer Material Science.; Snap-Fit Joints for Plastics; 26 pages; retrieved from the Internet: ( https://web.archive.org/web/201 21119232733if_/http://fab.cba.mit.edu:80/classes/S62.12/people/vernelle.noel/Plastic_Snap_fit_design.pd) on Sep. 26, 2018.

Schmitt et al.; A new rotational thrombectomy catheter: System design and first clinical esperiences: Cardiovascular and Interventional Radiology; Sprinver-Verlag; 22(6); pp. 504-509; Nov. 1, 1999.

Patel et al.; U.S. Appl. No. 16/801,047 entitled "Micro-molded anamorphic reflector lens for image guided therapeutic/diagnostic catheters," filed Feb. 25, 2020.

Sharma et al.; Common-path optical coherence tomography with side-viewing bare fiber probe for endoscopic optical coherence tomography; vol. 78; 113102; 5 pages; Nov. 6, 2007.

Merriam Webster; Proximal (Definition); 10 pages; retrieved from the internet (https://www.merriam-webster.com/dictionary/proximai) on Jun. 9, 2021.

Wikipedia; Hinge; 4 pages; retrieved from the internet (https://en.wikipedia.org/w/index.php?title=Hinge&oldid=479569345) on Jun. 9, 2021.

Smith et al.; U.S. Appl. No. 17/189,123 entitled "Optical pressure sensor assembly," filed Mar. 1, 2021.

Kankaria, U.S. Appl. No. 17/209,162 entitled "Optical coherence tomography with graded index fiber for biological imaging," filed Mar. 22, 2021.

Newhauser et al.; U.S. Appl. No. 17/209,168 entitled "Occlusion-crossing devices," filed Mar. 22, 2021.

Patel et al.; U.S. Appl. No. 17/347,419 entitled "Micro-molded anamorphic reflector lens for image guided therapeutic/diagnostic catheters," filed Jun. 14, 2021.

Smith et al.; U.S. Appl. No. 16/941,310 entitled "Chronic total occlusion crossing devices with imaging," filed Jul. 28, 2020.

Spencer et al.; U.S. Appl. No. 16/943,446 entitled "Catheter-based off-axis optical coherence tomography imaging system," filed Jul. 30, 2020.

Aziz et al.; Chronic total occlusions—a stiff challenge requiring a major breakthrough: is there light at the end of the tunnel?; Heart; vol. 91; suppl. III; pp. 42-48; Jun. 2005.

Choma et al.; Sensitivity advantage of swept source and fourier domain optical coherence tomography; Optics Express; 11(18); pp. 2183-2189; Sep. 8, 2003.

De Boer et al.; Improved signal-to-noise ratio in spectral-domain compared with time-domain optical coherence tomography; Optics Letters; 28(21); pp. 2067-2069; Nov. 2003.

Emkey et al.; Analysis and evaluation of graded-index fiber-lenses; Journal of Lightwave Technology; vol. LT-5; No. 9; pp. 1156-1164; Sep. 1987.

Gonzalo et al.; Optical coherence tomography patterns of stent restenosis; Am. Heart J.; 158(2); pp. 284-293; Aug. 2009.

Han et al.; In situ Frog Retina Imaging Using Common-Path OCT with a Gold-Coated Bare Fiber Probe; CFM6; San Jose, California; CLEO, May 4, 2008; 2 pages.

Leitgeb et al.; Performance of fourier domain vs time domain optical coherence tomography; Optics Express; 11(8); pp. 889-894; Apr. 21, 2003.

Linares et al.; Arbitrary single-mode coupling by tapered and nontapered grin fiber lenses; Applied Optics; vol. 29; No. 28; pp. 4003-4007; Oct. 1, 1990.

Muller et al.; Time-gated infrared fourier-domain optical coherence tomography; CFM5; San Jose, California; CLEO May 4, 2008; 2 pages.

Rollins et al.; Optimal interferometer designs for optical coherence tomography; Optics Letters; 24(21); pp. 1484-1486; Nov. 1999.

Sharma et al.; Optical coherence tomography based on an all-fiber autocorrelator using probe-end reflection as reference; CWJ13; San Francisco, California; CLEO May 16, 2004; 4 pages.

Shinkle et al.; Evaluation of stent placement and outcomes with optical coherence tomography; Interv. Cardiol.; 2(4); pp. 535-543; (manuscript version, 12 pages); Aug. 2010.

Suparno et al.; Light scattering with single-mode fiber collimators; Applied Optics; vol. 33; No. 30; pp. 7200-7205; Oct. 20, 1994.

(56) References Cited

OTHER PUBLICATIONS

Tanaka et al.; Challenges on the frontier of intracoronary imaging: atherosclerotic plaque macrophage measurement by optical coherence tomography; Journal of Biomedical Optics; 15(1); pp. (011104-1)-(011104-8); Jan.-Feb. 2010.

Wang et al.; Common-path endoscopic Fourier domain OCT with a reference Michelson interferometer; Proceedings of the SPIE; vol. 7566; pp. 75660L-75660L-7; Jan. 2010.

Fernandez et al., U.S. Appl. No. 16/305,136 entitled "Catheter device with detachable distal end," filed Nov. 28, 2018.

Tachibana et al.; U.S. Appl. No. 16/372,112 entitled "Atherectomy catheter drive assemblies," filed Apr. 1, 2019.

Radjabi et al.; U.S. Appl. No. 16/347,840 entitled "Methods, systems and apparatuses for displaying real-time catheter position," filed May 7, 2019.

Patel et al.; U.S. Appl. No. 17/046,066 entitled "Occlusion-crossing devices," filed Oct. 8, 2020.

Simpson et al.; U.S. Appl. No. 17/075,548 entitled "Identification of elastic lamina to guide interventional therapy," filed Oct. 20, 2020.

Patel et al.; U.S. Appl. No. 17/443,398 entitled "Guidewire positioning catheter," filed Jul. 26, 2021.

Gupta et al.; U.S. Appl. No. 17/445,648 entitled "Tissue collection device for catheter," filed Aug. 23, 2021.

Simpson et al.; U.S. Appl. No. 17/449,867 entitled "Occlusion-crossing devices, imaging, and atherectomy devices," filed Oct. 4, 2021.

Spencer et al.; U.S. Appl. No. 17/449,895 entitled "Occlusion-crossing devices, atherectomy devices, and imaging," filed Oct. 4, 2021.

Patel et al.; U.S. Appl. No. 17/450,658 entitled "High speed chronic total occlusion crossing devices," filed Oct. 12, 2021.

\* cited by examiner

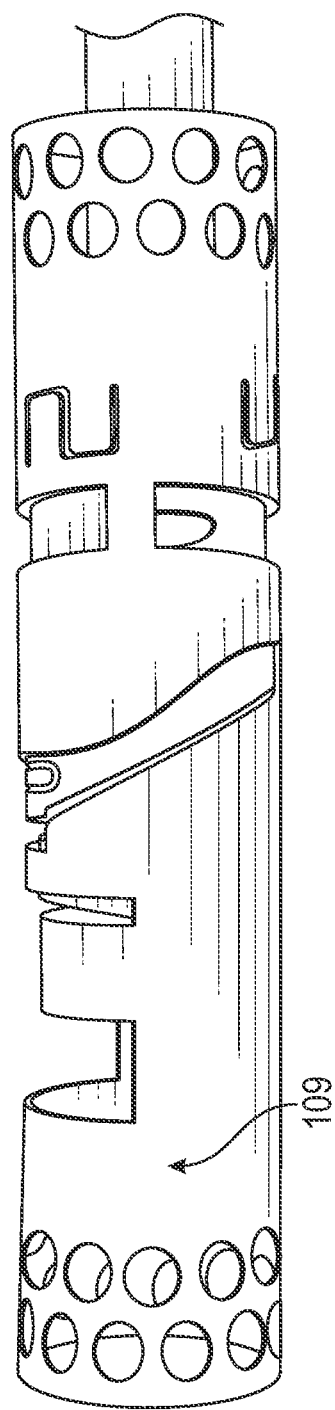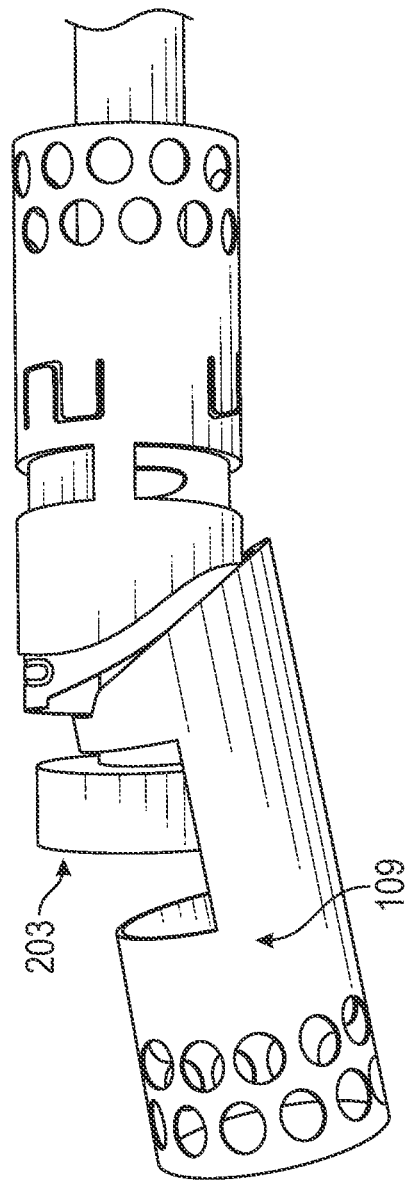
FIG. 2A
FIG. 2B

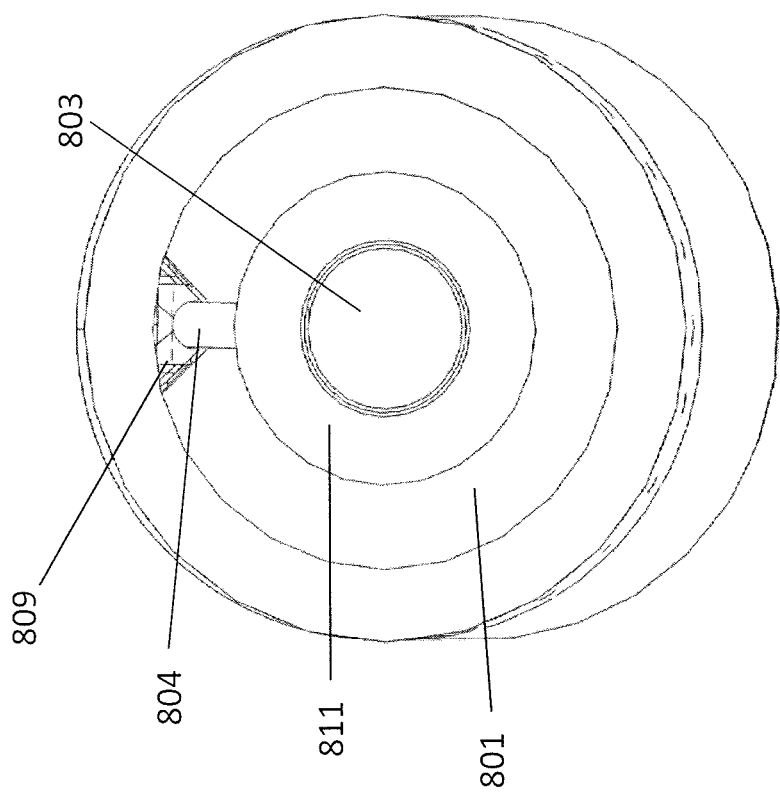
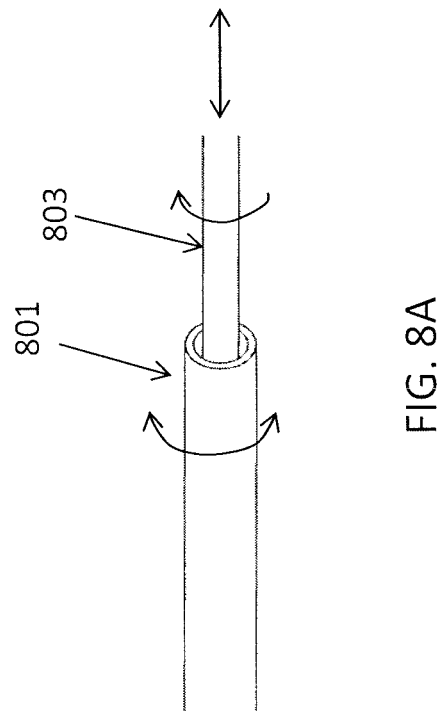

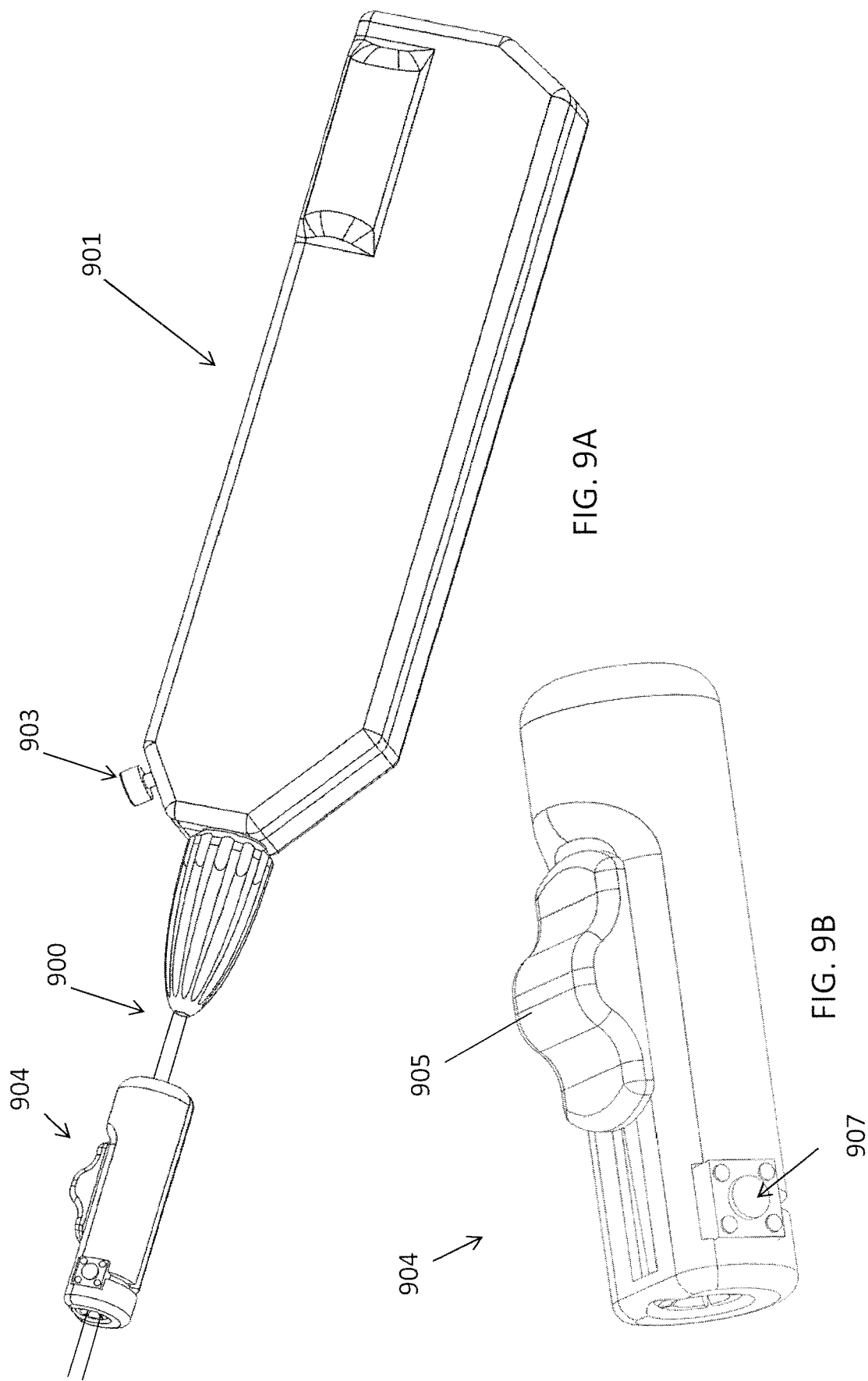

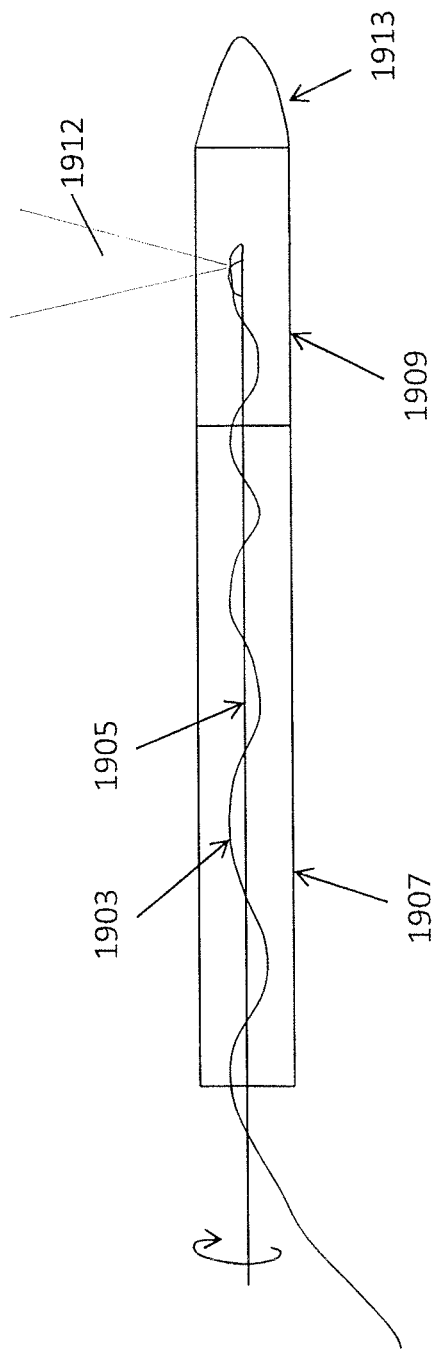
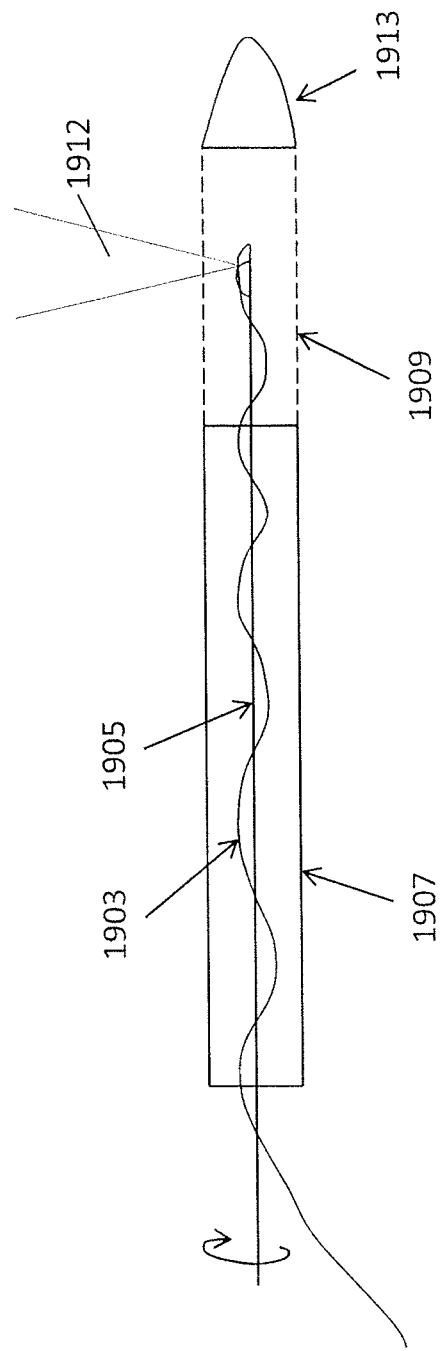
FIG. 19A
FIG. 19B

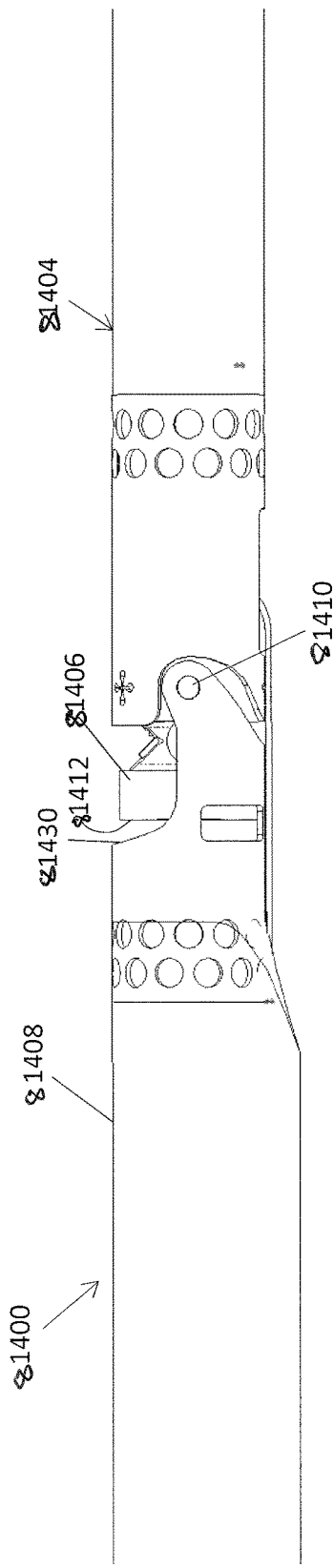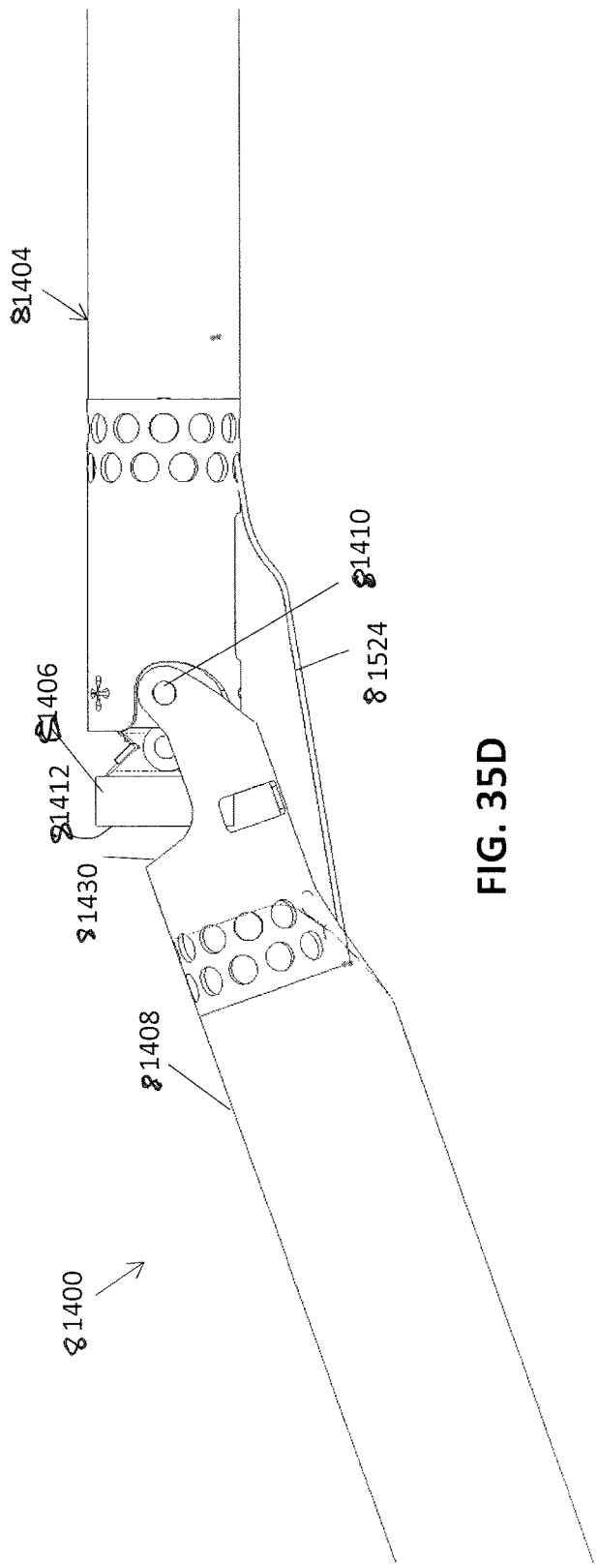
FIG. 35C
FIG. 35D

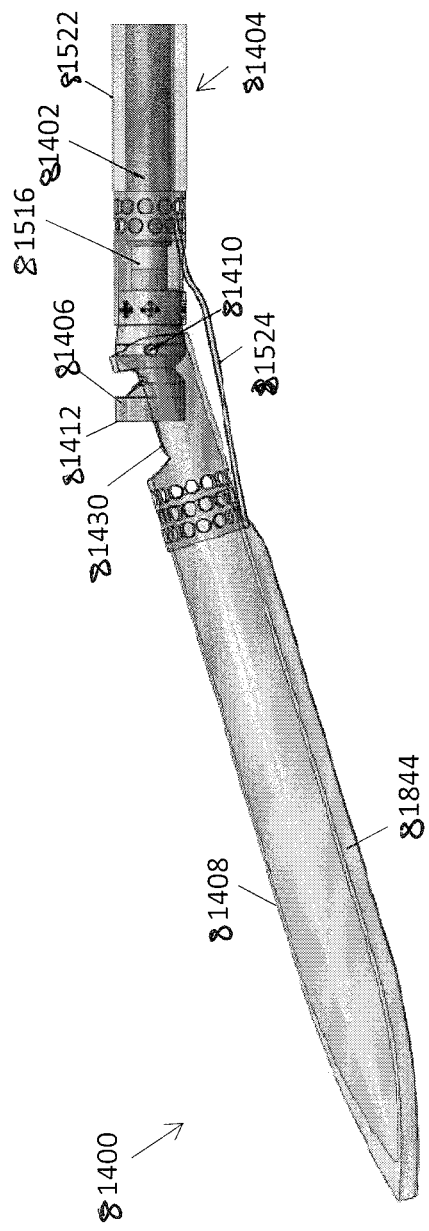
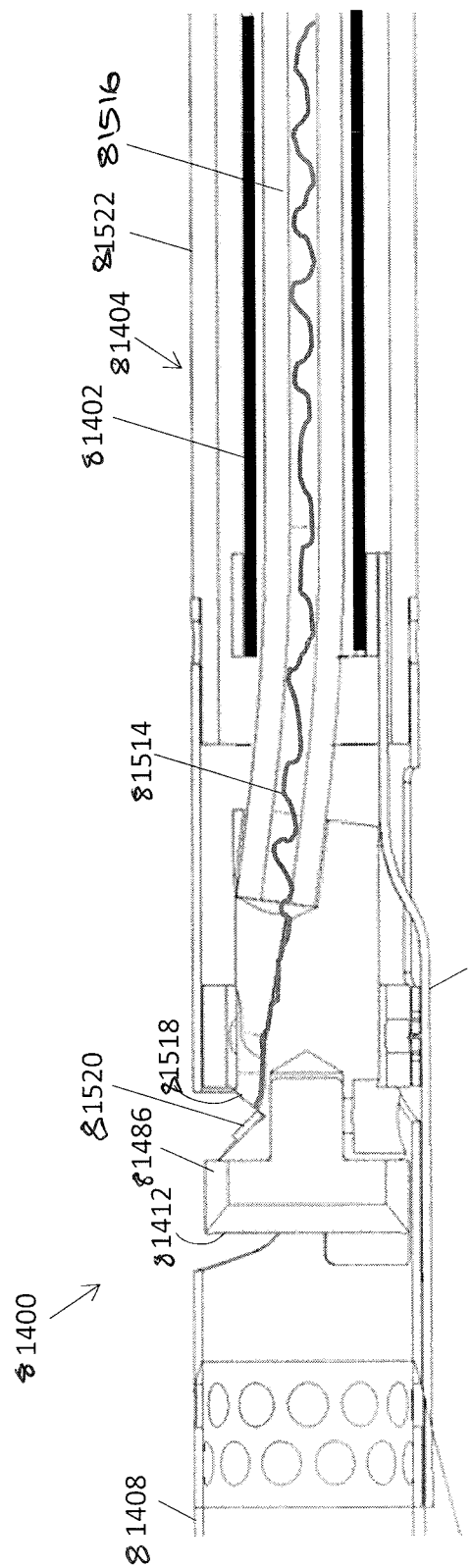
FIG. 36A
FIG. 36B

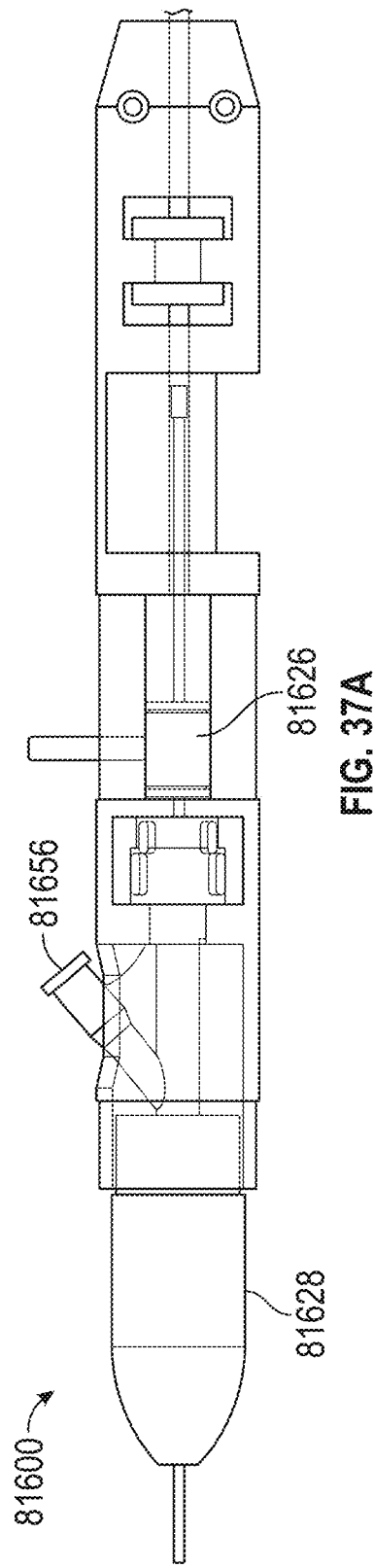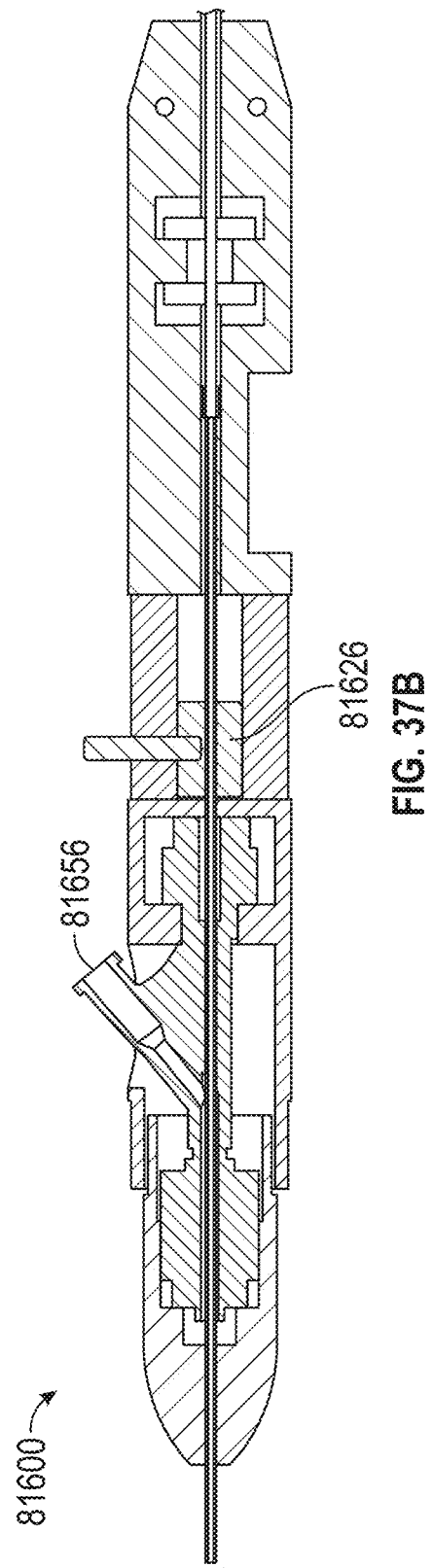

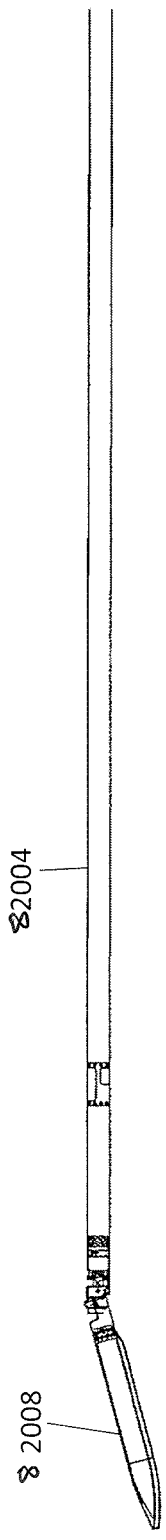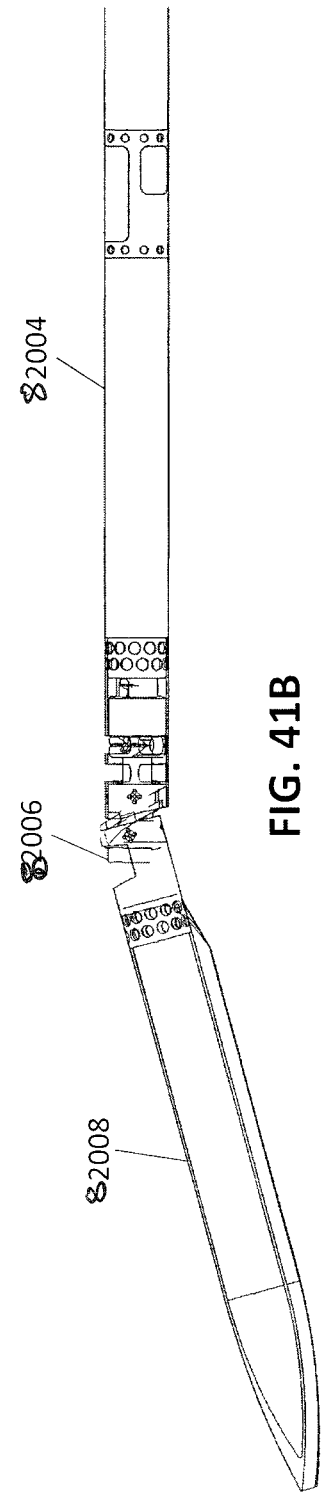

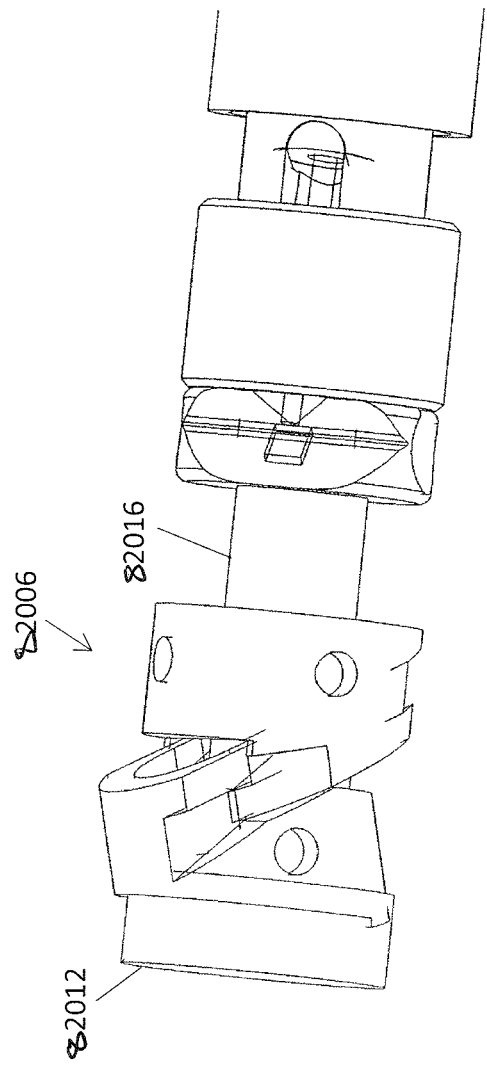
FIG. 41E
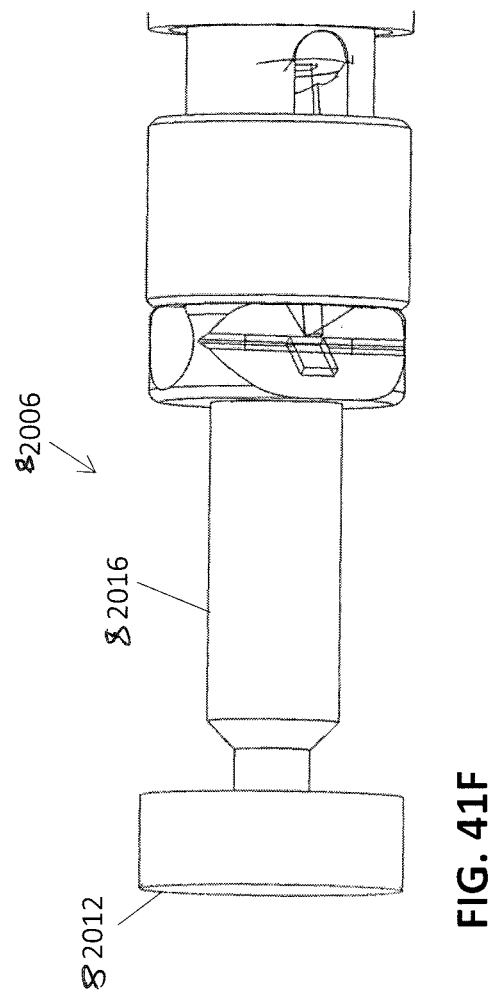
FIG. 41F
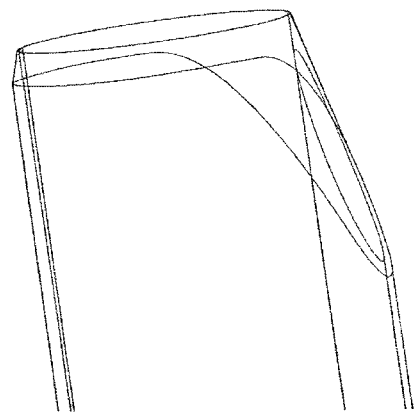
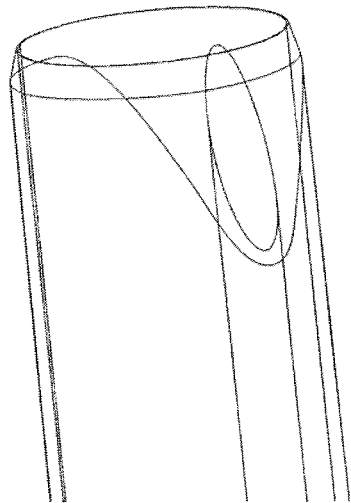

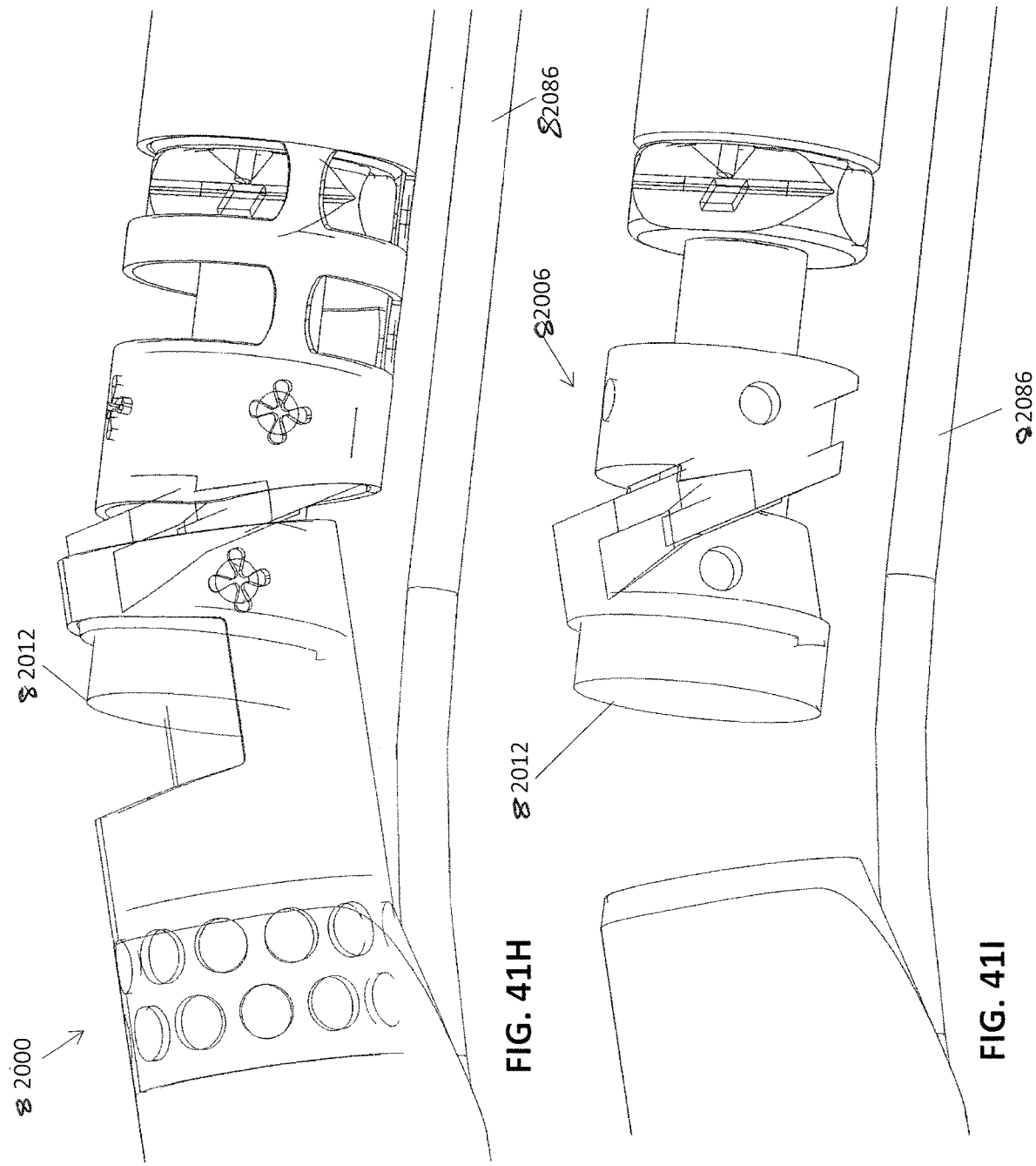

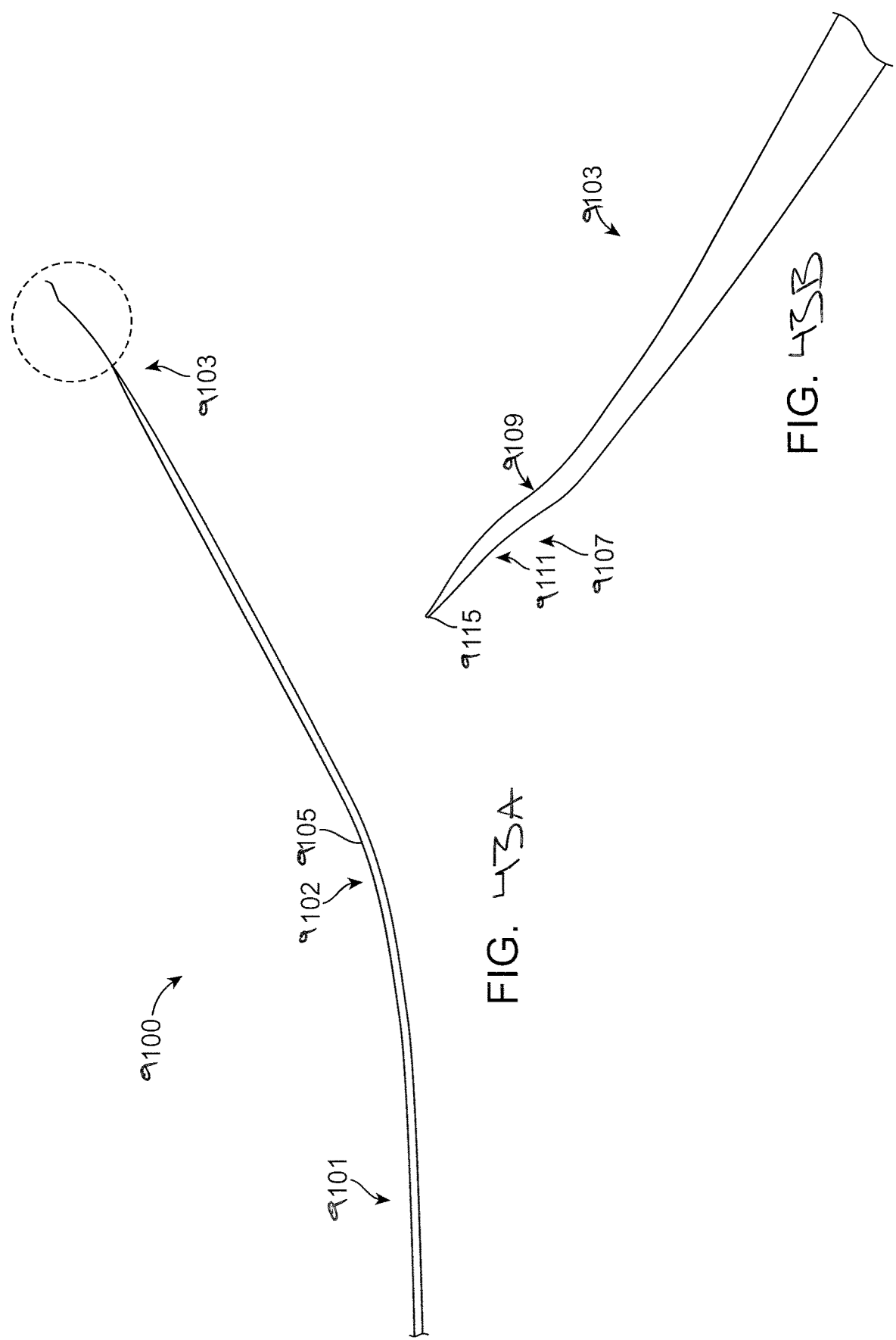

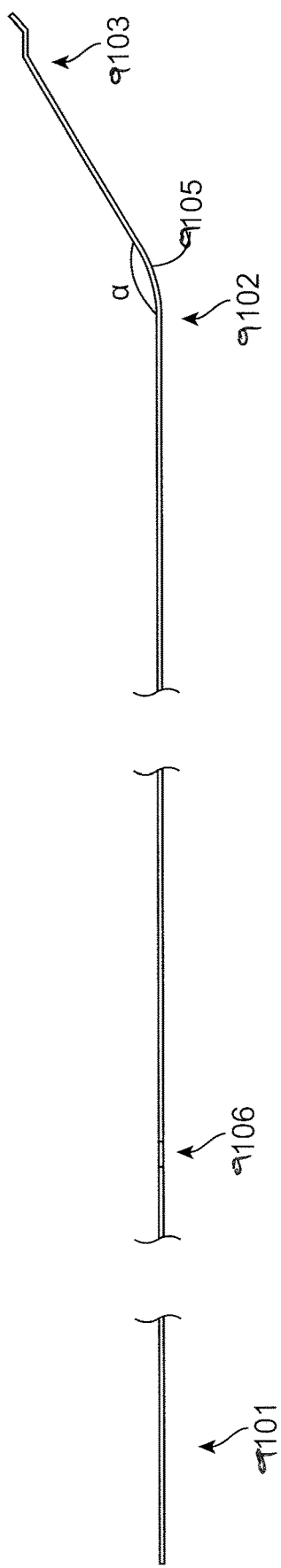
FIG. 44A
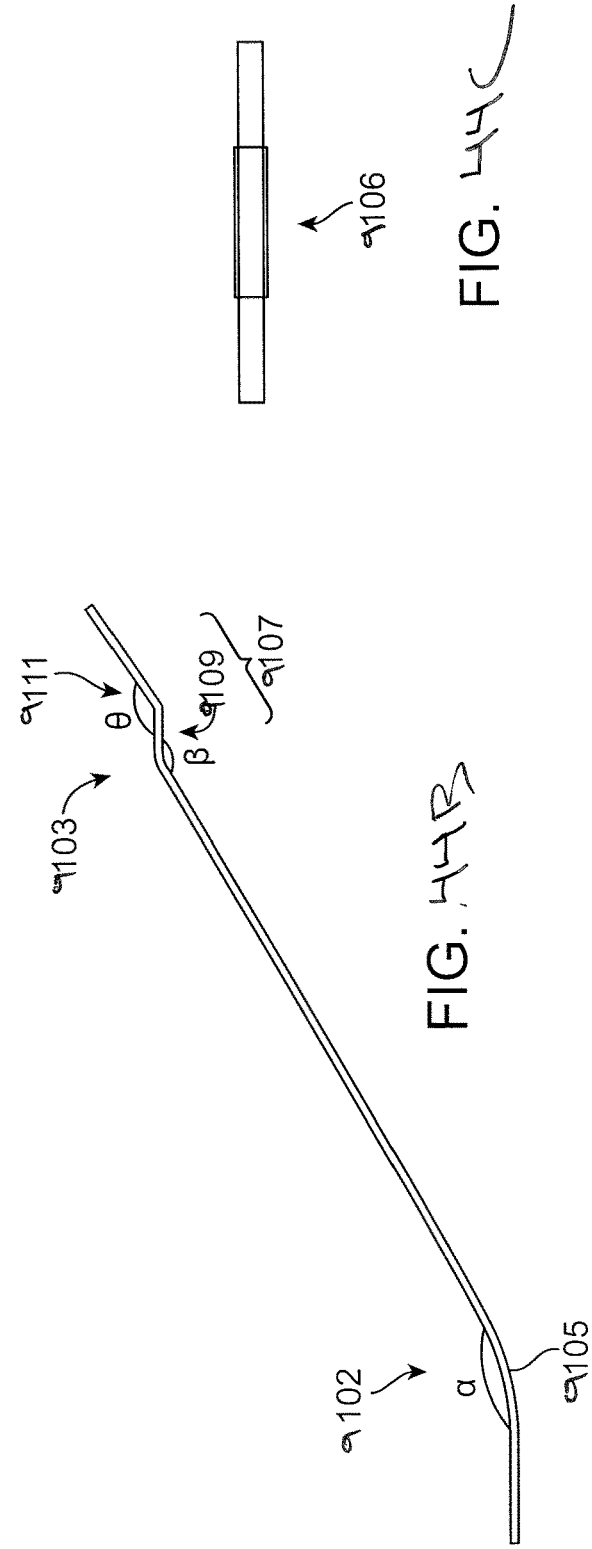
FIG. 44C
FIG. 44B

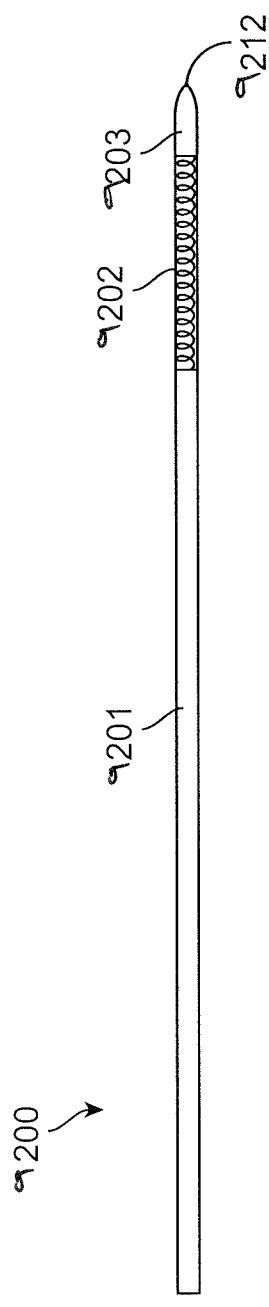
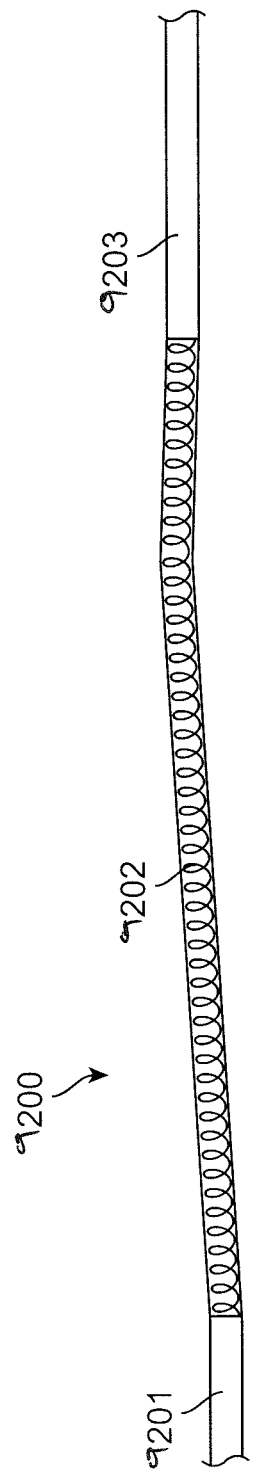

9991

9993

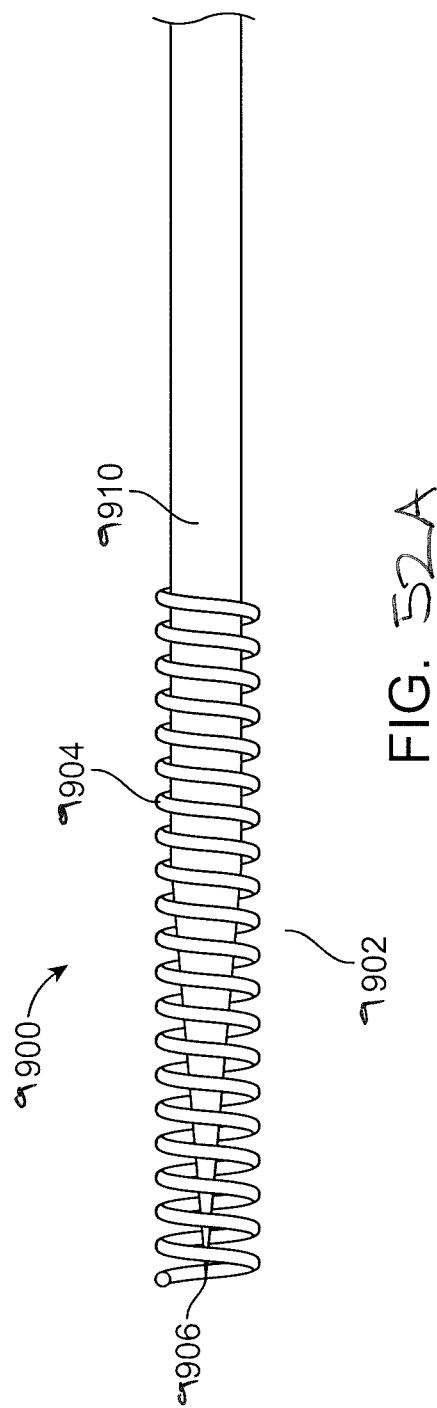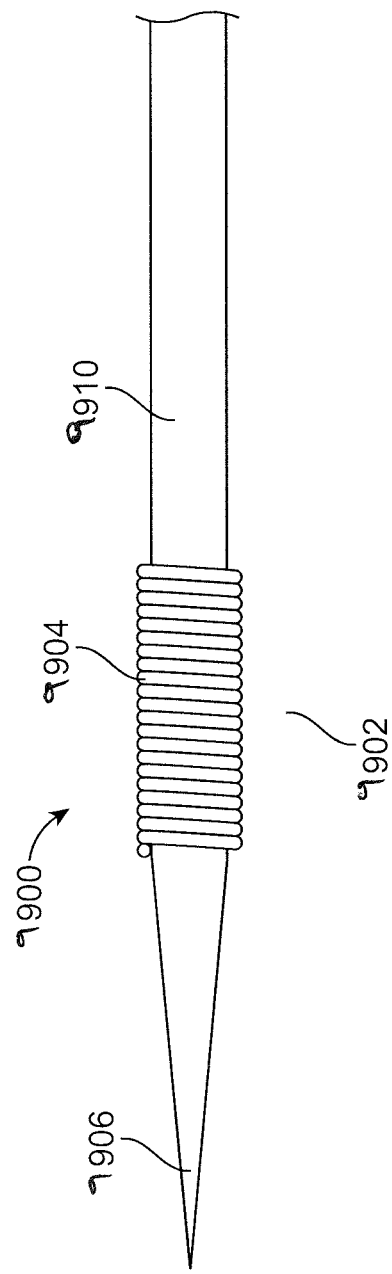
FIG. 52A
FIG. 52B

ATHERECTOMY CATHETER

CROSS REFERENCE TO RELATED APPLICATIONS

This patent application is a continuation in part of U.S. patent application Ser. No. 15/162,330, filed May 23, 2016, titled "ATHERECTOMY CATHETERS WITH LONGITUDINALLY DISPLACEABLE DRIVE SHAFTS," which is a continuation of U.S. patent application Ser. No. 13/175,232, filed Jul. 1, 2011, titled "ATHERECTOMY CATHETERS WITH LONGITUDINALLY DISPLACEABLE DRIVE SHAFTS," now U.S. Pat. No. 9,345,510, which claims priority to U.S. Provisional Patent Application No. 61/360,886, titled "ATHERECTOMY CATHETERS WITH LONGITUDINALLY DISPLACEABLE DRIVE SHAFT," filed on Jul. 1, 2010, U.S. Provisional Patent Application No. 61/468,396, titled "OCCLUSION CROSSING DEVICES, IMAGING, AND ATHERECTOMY DEVICES," filed on March 28, 2011, and U.S. Provisional Patent Application No. 61/492,693, titled "ATHERECTOMY CATHETERS WITH LONGITUDINALLY DISPLACEABLE DRIVE SHAFTS" and filed on Jun. 2, 2011, each of which is incorporated by reference herein in its entirety.

This patent application is also a continuation in part of U.S. patent application Ser. No. 13/654,357, filed Oct. 17, 2012, titled "ATHERECTOMY CATHETERS AND NON-CONTACT ACTUATION MECHANISM FOR CATHETERS," now U.S. Pat. No. 10,363,062, which claims priority to U.S. Provisional Patent Application 61/646,843, titled "ATHERECTOMY CATHETERS WITH IMAGING," filed on May 14, 2012, and U.S. Provisional Patent Application No. 61/548,179, titled "OCCLUSION-CROSSING DEVICES, IMAGING, AND ATHERECTOMY DEVICES," filed on Oct. 17, 2011, each of which is incorporated by reference herein in its entirety.

This patent application is also a continuation in part of U.S. patent application Ser. No. 14/424,266, filed Feb. 26, 2015, titled "RE-ENTRY STYLET FOR CATHETER," which is a U.S. National Phase Application Under 35 U.S.C. § 371 of International Application No. PCT/US2013/032196, filed Mar. 15, 2013, titled "RE-ENTRY STYLET FOR CATHETER," which claims priority to U.S. Provisional Patent Application 61/697,726, titled "RE-ENTRY STYLET FOR CATHETER," filed on Sep. 6, 2012, each of which is incorporated by reference herein in its entirety.

U.S. patent application Ser. No. 13/175,232 may be related to U.S. patent application Ser. No. No. 12/829,277, titled "ATHERECTOMY CATHETER WITH LATERALLY-DISPLACEABLE TIP," filed on Jul. 1, 2010, each of which is incorporated by reference herein in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

Described herein are atherectomy catheters with independently controlled imaging. These atherectomy catheters may include longitudinally actuated cutters, systems including such catheters and methods of using them.

Additionally described herein are atherectomy catheters including a pull shaft and pull-wire mechanism configured to deflect a distal end region of the catheter and expose a cutter. Also described herein are non-contact mechanisms for driving catheters, such as occlusion-crossing and atherectomy catheters. More specifically, described herein are non-contact magnetic drive systems for controlling motion (e.g., rotation of the cutting and/or imaging elements) of the catheter without contacting catheter, thereby maintaining sterility of the catheter even when using a non-sterile driver.

Additionally described herein are stylets, and more specifically to stylets used to cross occlusions and/or to re-enter a true lumen of a vessel.

BACKGROUND OF THE INVENTION

Peripheral artery disease (PAD) affects millions of people in the United States alone. PAD is a silent, dangerous disease that can have catastrophic consequences when left untreated. PAD is the leading cause of amputation in patients over 50 and is responsible for approximately 160,000 amputations in the United States each year.

Peripheral artery disease (PAD) is a progressive narrowing of the blood vessels most often caused by atherosclerosis, the collection of plaque or a fatty substance along the inner lining of the artery wall. Over time, this substance hardens and thickens, which may interfere with blood circulation to the arms, legs, stomach and kidneys. This narrowing forms an occlusion, completely or partially restricting flow through the artery. The most significant of these occlusions are called chronic total occlusions (CTO). Blood circulation to the brain and heart may be reduced by CTOs, increasing the risk for stroke and heart disease.

Interventional treatments for PAD may include endarterectomy and/or atherectomy. Endarterectomy is surgical removal of plaque from the blocked artery to restore or improve blood flow. Endovascular therapies such as atherectomy are typically minimally invasive techniques that open or widen arteries that have become narrowed or blocked. Other treatments may include angioplasty to open the artery. For example, a balloon angioplasty typically involves insertion of a catheter into a leg or arm artery and is positioned such that the balloon resides within the blockage. The balloon, connected to the catheter, is expanded to open the artery. Surgeons may then place a wire mesh tube, called a stent, at the area of blockage to keep the artery open.

A significant body of scientific and clinical evidence supports atherectomy as a viable primary or adjunctive therapy prior to stenting for the treatment of occlusive coronary artery disease. Atherectomy offers a simple mechanical advantage over alternative therapies. By removing the majority of plaque mass (debulking) it creates a larger initial lumen and dramatically increases the compliance of the arterial wall. As a result, stent deployment is greatly enhanced.

Additionally, there are advantages related to the arterial healing response. When circumferential radial forces are applied to the vasculature, as in the case of angioplasty or stenting, the plaque mass is displaced, forcing the vessel wall to stretch dramatically. This stretch injury is a known stimulus for the cellular in-growth that leads to restenosis. By removing the disease with minimal force applied to the vessel and reducing the plaque burden prior to stent placement, large gains in lumen size can be created with decreased vessel wall injury and limited elastic recoil which have shown to translate into better acute results and lower restenosis rates.

Traditional atherectomy devices have been plagued by a number of problems that have severely limited market adoption of these devices. These challenges include the following: (1) the need for large vessel access devices; (2) the presence of rigid distal assembles, which make device introduction and control challenging; (3) the need for a fixed and predictable cut length; (4) the need for predictable cut depth; (5) the desire for sufficient tissue collection and removal; and (6) the need for simplified user operation. Additional reasons for the lack of adoption are the cost, complexity and limited applicability of currently available devices. Many designs are unable to treat the wide range of disease states present in long complex lesions; luminal gain is often limited by the requirement of the physician to introduce multiple devices with increased crossing profiles; tissue collection is either unpredictable or considered unnecessary based on assumptions regarding small particle size and volumes; and optimal debulking is either not possible due to lack of intravascular visualization or requires very long procedure times. Based on these limitations current devices are likely to perform poorly in the coronary vasculature where safety and efficacy in de novo lesions, ostials, and bifurcations continue to pose great challenges.

Previously, atherectomy devices focused on macerating or emulsifying the atherosclerotic plaque such that it may be considered clinically insignificant and remain in the blood stream or aspirated proximally through small spaces in the catheter main body. The reliability of these devices to produce clinically insignificant embolization has been questioned when not aspirated through the catheter to an external reservoir. Aspiration requires a vacuum be applied to a lumen or annular space within the catheter to remove emulsified tissue. In early clinical evaluations of aspiration the presence of negative pressure at the distal working assembly cause the artery to collapse around the cutting element causing more aggressive treatment, dissections and/or perforations. In addition, the option for post procedural analysis of any removed disease is extremely limited or impossible. Atheromed, Pathway Medical and Cardio Vascular Systems, Inc. are examples of companies working on such product designs.

Other atherectomy devices include the directional atherectomy devices such as those developed by DVI and FoxHollow. These catheters use cupped cutters that cut and "turn" the tissue distal into a storage reservoir in the distal tip of the device. This approach preserves the "as cut" nature of the plaque but requires large distal collection elements. These large distal tip assemblies can limit the capabilities of the system to access small lesions and create additional trauma to the vessel.

Currently available atherectomy devices also do not include, and are poorly adapted for use with, real time image guidance. Physician practice is often to treat target lesion as if they contain concentric disease even though intravascular diagnostic devices have consistently shown significantly eccentric lesions. This circumferential treatment approach virtually ensures that native arterial wall and potentially healthy vessel will be cut from the vasculature.

The systems and devices described herein may overcome these hurdles and give physicians a safe, reliable, and simple cutting system that enables the precision required in eccentric lesions, various disease states, and tortuous anatomy.

Additionally, many minimally invasive techniques (e.g., atherectomy, angioplasty, etc.) require either rotational and/or longitudinal motion of components (e.g. for cutting, imaging, and/or packing of tissue). Such activation, however, generally requires use of a drive system connected to the catheter. Disposable drive systems, however, are expensive and impractical. On the other hand, reusable drive systems can be problematic for keeping the surgical field sterile. What is needed, therefore, is a reusable drive system that can easily be kept in the sterile field.

Further, such minimally invasive techniques (e.g., atherectomy, angioplasty, etc.) typically involve the placement of a guidewire through the occlusion. Using the guidewire, one or more interventional devices may be positioned to remove or displace the occlusion. Unfortunately, placement of the guidewire, while critical for effective treatment, may be difficult. In particular, when placing a guidewire across an occlusion, it may be difficult to pass the guidewire through the occlusion while avoiding damage to the artery. For example, it is often difficult to prevent the guidewire from traveling out of the true lumen and into the subintimal layers, such as the adventitia and surrounding tissues. This can cause damage to the vessel and, once out of the true lumen, it can be difficult to direct the guidewire back into the true lumen, thereby preventing effective treatment of the occlusion. A device or system that can assist in re-entry into the true lumen of a vessel is therefore also desired.

SUMMARY OF THE INVENTION

Described herein are atherectomy catheters, systems including them and methods of using them. Some of the distinguishing features that may be included as part of these devices, systems and methods are summarized below.

In particular, described herein are atherectomy catheters devices described including one or more cutters configured to cut tissue that are actuated by longitudinal motion of a drive shaft, e.g., in the proximal/distal axis of the device. The same drive shaft may be used to rotate the cutter, which may be a ring-type cutter at a rotational speed appropriate for cutting the tissue. For example, the cutter may rotate at between about 200 and 5000 RPM (e.g., about 500 RPM, about 600 rpm, about 700 RPM, about 1000 RPM, etc.). Any of these variations may also include imaging such as optical coherence tomography (OCT) imaging configured to image the vessels tissue, including penetrating some depth into the vessel to image the tissue surrounding the blood vessel (such as the intima, media and externa layers). Imaging may help navigate as well as remove atheromatous plaques.

In general the imaging may include an optical sensor, such as an optical fiber end region when OCT is used, which may also rotate around the circumference of the device. This sensor region may be located proximally or distally to the cutter. The imaging sensor may include a lens and/or window through which light is transmitted. In general, the imaging sensor may be rotated around the periphery of the device. In some variations the imaging elements include OCT imaging elements that are off-axis within the catheter, which may be rotated manually or automatically for a number of turns in a first direction before rotating for a number of turns in a second direction. A separate drive shaft from the cutting drive shaft may be used to drive rotation of the imaging sensor, or the same drive shaft may be used. In general, the imaging sensor rotates at a much slower rate than the cutter. For example, the imaging sensor may rotates at about 30 RPM (e.g., between about 2 and about 50 RPM, between about 10 and 40 PM, between about 15 and 40 RPM, etc.). As mentioned, the imaging sensor may rotate approximately 10 time (e.g., 5, 7, 8, 9, 10, 11, 12, 13, 14, 15, etc.) times around the circumference of the device clockwise before then switches direction to rotate counterclockwise for the same number of rotations, and switching direction again.

The cutter, which may be a rotating ring, may rotate in a single direction (e.g., clockwise, counterclockwise), or it may oscillate back and forth between clockwise and counterclockwise directions. The ring may have a sharp edge, a serrated edge, or the like.

In some variations, the catheter device also includes a handle having one or more controls for controlling the catheter. In addition, the devices or systems may also include one or more controls for controlling the rotation and/or oscillation of the annular cutting ring and/or the imaging system. The devices or systems may also include controls for an associate imaging (e.g., OCT) system. In some variations the device or system includes control logic for regulating the displacement and/or rotation and/or imaging. Proximal controls may include an automated advancement function to ensure proximal motion correlates to distal tracking in the vessel. In some variations, some or all of these controls may be on a handle, or may be on a separate controller.

Force limiting controls may also be used to ensure the input forces do not exceed what is required to effectively cut diseased tissue. This may reduce the chances of the device moving outside the perimeter of the lesion while activated thereby cutting into healthy arterial wall.

In some variations, the catheter systems described herein are compatible with 7F sheath access to the peripheral arteries, or 6F sheath sizes.

Any of these devices may also include one or more drive shafts (e.g., a cutter drive shaft and/or an imaging drive shaft) extending along the length of the catheter body. For example, the cutter drive shaft may comprise a cable drive shaft having a distal gear configured to drive rotation of the cutting ring. In some variations, the annular cutting ring comprises internal gear teeth configured to mate with a drive shaft to rotate the cutting ring.

The drive shaft may be directly connected to the annular cutting ring. For example, the drive shaft comprises a hollow tubular drive shaft. Similarly, the imaging drive shaft (in variations having a separate imaging drive shaft) may be directly connected to the optical head that rotates, or the rotation may be geared. The optical and cutting drive shafts may be coaxially arranged. For example, the cutting drive shaft may be surrounded by the imaging drive shaft; a lubricious fluid and/or intermediary layer may be positioned between the drive shafts. In some variations the drive shafts may be coaxially positioned relative to each other. Alternatively, in some variations, the drive shafts are parallel to each other within the lumen of the catheter.

In some variations the imaging element is driven off of the same drive shaft that moves the cutting element, but at a different rate; thus the imaging element may be geared down (or the cutting element may be geared up) to drive the imaging sensor and cutting element at different rates.

Any of the catheters described herein may include a guidewire lumen extending the length of the catheter. The lumen may be centered or off-centered, and one or more additional lumens may also be included.

In some variations, the annular cutting ring may form an outer surface of the catheter in both the closed and open configurations.

In some variations the distal tip region of the catheter is deflected off-axis from the proximal region of the catheter and cutter, to expose the rotating cutting edge of the cutter and allow it to cut tissue. For example, the catheter may be configured so that lateral movement of the cutter drive shaft causes the distal end of the catheter to displace (e.g., bend) away from the cutting ring, exposing it so that it may cut tissue. The distal end of the device may bend at an angle for the immediately adjacent proximal region of the catheter, and/or it may displace off-axis, as described in the U.S. Ser. No. 12/829,277, titled "ATHERECTOMY CATHETER WITH LATERALLY-DISPLACEABLE TIP," which was previously incorporated by reference. The distal tip region may also be moved back into line with the proximal region of the catheter, preventing further cutting. Other variations are also described herein, including variations in which lateral movement of the cutting element extends the cutting element radially from the side of the catheter, where it may engage with the wall of the vessel. Other variations include oscillating cutters.

Some variations of the atherectomy catheter devices may also include an internal tissue collection region configured to receive tissue cut by the annular cutting ring. For example, the tissue collection region may be located within the distal tip assembly. The tissue collection region may be located within the catheter body.

As mentioned, in any of these variations, the catheter may include an OCT imaging subassembly. For example, the OCT imaging subassembly may include a fiber optic extending the length of the catheter body. The OCT imaging assembly may comprise a side-facing OCT emitting element fixed proximal to the annular cutting ring. Alternatively, the OCT imaging assembly may include a side-facing OCT emitting element fixed distally to the annular cutting ring.

For example, described herein are atherectomy catheter devices configured to visualize and to cut tissue. Such devices may include: a distal tip; a cutter proximal to the distal tip, the cutter having a cutting edge that is configured to rotate; an imaging sensor proximal to the cutter and configured to rotate independently of the cutter; and a cutter drive shaft coupled to the cutter and configured to rotate the cutter wherein the cutter drive shaft is further configured to be longitudinally displaced proximally or distally to deflect the distal tip to expose the cutting edge of the cutter.

The device may also include a ramped slide surface between the distal tip and a region of the catheter proximal to the cutter, wherein the ramped slide surface is configured to guide deflection of the distal tip as the cutter drive shaft is moved longitudinally. The device may also include an imaging drive shaft coupled to the imaging sensor and configured to rotate the imaging sensor. The imaging drive shaft may be located coaxially to the cutting drive shaft. For example, in some variations the imaging drive shaft is positioned within the cutting drive shaft. In some variations the catheter does not include a separate drive shaft for the imaging and cutting elements, but a single drive shaft is used with gears to step up or step down the rate of rotation so that the cutter may be rotated more rapidly than the imaging drive shaft. Also, in general, the imaging drive shaft may be configured to alternately rotate the imaging sensor clockwise and counterclockwise, particularly in variations in which the imaging sensor element is an OCT imaging element having an off-axis optical fiber within the catheter.

Thus, as just indicated, in some variations the imaging sensor comprises an OCT imaging sensor, and in some variations the imaging sensor comprises a fiber optic extending off-axis along the longitudinal length of the catheter.

The cutter may be a ring cutter; for example, the cutter may be a complete or partial ring of metal having a cutting edge that is exposed only when the distal tip region is displaced. In general, the distal tip region may be displaced by sliding it at least slightly off-axis, and in some variations, also bending it away from the longitudinal axis of the catheter (relative to the region of the catheter just proximal to the distal tip region). Thus, in some variations, the slider region may be used to guide the deflection of the distal tip region.

The distal tip may be hollow, and in some variations may be clear. The distal tip region may be configured to collect tissue cut by the cuter. In some variations the distal tip region is configured to be removable (and/or replaceable). For example, the distal tip may be threaded or otherwise removably secured to the distal end of the catheter. The distal tip region may include a flush port to allow removal of the cut material collected therein.

In any of the variations described herein, the catheters may include a proximal handle having a first driver for driving rotation of the cutter and a second driver for driving rotation of the imaging sensor.

For example, described herein are proximal handles having a first driver for driving rotation of the cutter between 100 and 10,000 rpm, and a second driver for driving rotation of the imaging sensor at less than 100 rpm. As mentioned, the proximal handle may include a first driver for driving rotation of the cutter in a first direction and a second driver for alternately driving rotation of the imaging sensor in a first rotational direction and a second rotational direction.

Also described herein are atherectomy catheter devices configured to visualize and to cut tissue that include: a distal tip; a cutter proximal to the distal tip, the cutter having a cutting edge that is configured to rotate; an imaging sensor proximal to the cutter and configured to rotate independently of the cutter; a cutter drive shaft coupled to the cutter and configured to rotate the cutter wherein the cutter drive shaft is further configured to be longitudinally displaced proximally or distally to deflect the distal tip to expose the cutting edge of the cutter; and an imaging drive shaft coupled to the imaging sensor and configured to alternately rotate the imaging sensor clockwise and counterclockwise.

Some variations of the catheters described herein do not necessarily include imaging (e.g., OCT imaging or other imaging modalities), although OCT imaging may be incorporated into any of them. For example, described herein are atherectomy catheter devices having: a distal tip; a cutter proximal to the distal tip, the cutter having a cutting edge that is configured to rotate; and a cutter drive shaft coupled to the cutter and configured to rotate the cutter wherein the cutter drive shaft is further configured to be longitudinally displaced proximally or distally to deflect the distal tip to expose the cutting edge of the cutter. The device may also include a proximal handle having a control for controlling the longitudinal displacement of the cutter drive shaft.

Also described herein are atherectomy catheter devices including: a distal tip; a cutter proximal to the distal tip, the cutter having a cutting edge that is configured to rotate; a cutter drive shaft coupled to the cutter and configured to rotate the cutter; and a ramped slide surface between the distal tip and a region of the catheter proximal to the cutter, wherein the ramped slide surface guides deflection of the distal tip to expose the cutting edge of the cutter.

Another variation of an atherectomy catheter device as described herein for visualizing and cutting tissue may include: a distal tip; a cutter proximal to the distal tip, the cutter having a cutting edge that is configured to rotate; an imaging sensor proximal to the cutter and configured to rotate independently of the cutter; a cutter drive shaft coupled to the cutter and configured to rotate the cutter; and a ramped slide surface between the distal tip and a region of the catheter proximal to the cutter, wherein the ramped slide surface guides deflection of the distal tip to expose the cutting edge of the cutter.

Methods of operating an atherectomy device, and/or for performing an atherectomy are also described. For example, described herein is a method for operating an atherectomy device comprising deflecting the distal tip region of an atherectomy catheter by driving the distal tip region against a ramped slide surface to displace the distal tip region and expose a rotatable cutter; rotating the cutter at a first rate between 100 and 10,000 rpm; and rotating an imaging element located proximal to the cutter on the catheter at a rate that is less than 100 rpm while imaging. As mentioned, the imaging element (e.g., the end of the fiber optic in an OCT imaging modality) may be alternately rotated clockwise and then counterclockwise; in some variations the imaging element is rotated first clockwise a predetermined number of rotations (e.g., between 1 and 20, such as 9, 10, 11, 12, etc. rotations) then counterclockwise the same number of rotations.

Deflecting the distal tip may include moving a rotatable drive shaft within the catheter longitudinally to displace the distal tip.

Also described herein is a method of operating an atherectomy device, the method comprising: deflecting the distal tip of an atherectomy catheter by moving a drive shaft of the catheter longitudinally to drive a distal tip region of the catheter against a ramped slide surface and thereby to displace the distal tip region and expose a rotatable cutter; rotating the cutter at a first rate between 100 and 10,000 rpm; and rotating an imaging element located proximal to the cutter on the catheter alternately clockwise and counterclockwise at a rate that is less than 100 rpm.

Any of the atherectomy devices described herein may be used without imaging, and may therefore be adapted for use without an imaging sensor (e.g., mirror, fiber, etc.). Thus, in one variation an atherectomy device may be configured to allow axial pushing or pulling of a member (e.g., a torque shaft) to displace the distal tip region and expose the cutting member.

Also described herein are imaging catheters or imaging wires having an optical fiber (e.g., for use with an OCT imaging sensor) that is configured to wrap around a central wire or fiber which may be configured as a drive shaft. These imaging catheters may be used without (or as part of) an atherectomy device or system. The distal end of the fiber is coupled (e.g., glued, epoxied, etc.) to the rotatable distal end of the imaging wire, and the distal end and end of the imaging fiber may be rotated by rotating the central drive shaft. The portion of the imaging catheter proximal to the rotating distal tip region (which may be referred to as a torque shaft) does not rotate with the tip region, and may remain stationary relative to the distal tip. In operation, the optical fiber connected to the distal may wrap around the central wire/fiber, and may be configured to allow numerous (up to a few hundred) rotations in a first direction (e.g., clockwise) before having to rotate counterclockwise, and then cycling back through clockwise rotations again. In some variations the catheter may include a central lumen through which fluid (e.g., saline) may be flushed, with one or more flushing ports located distally to allow flushing to clear the imaging pathway.

Also described herein are variations of imaging catheters in which both the distal end of the catheter and the torque shaft region of the catheter rotates while the centrally located optical fiber twists. In this variation the distal end of the optical fiber is configured as the imaging sensor, and is fixed to the rotating imaging head. The more proximal end of the fiber is fixed relative to the rotating distal tip. As the distal tip rotates, the fiber is allowed to twist and rotate; although this would seem to damage the optical fiber, in practice the fiber may be rotated in this manner though hundreds of complete rotations without substantially degrading in signal transmission or structure.

Also described herein are atherectomy catheters configured to cut occlusive material from a vessel using a rotational cutter. The rotational cutter can be exposed through deflection of the distal tip by a pull shaft connected to a nosecone, such as through a pull-wire. The rotational cutter may have a circular (e.g., ring-shaped) profile.

In general, in one aspect, an atherectomy catheter includes a deflectable distal tip, a rotatable cutter proximal to the distal tip, a cutter drive shaft configured to rotate the rotatable cutter, and a pull shaft concentric with the drive shaft and coupled to the distal tip. The pull shaft is configured such that pulling the pull shaft deflects the distal tip, thereby exposing the rotatable cutter.

This and other embodiments can include one or more of the following features. The atherectomy catheter can include an optical fiber for OCT imaging coupled to the rotatable cutter. The drive shaft can be hollow, and an optical fiber for OCT imaging can extend within the drive shaft. The optical fiber can be attached to the rotatable cutter but be otherwise free to float within the drive shaft. The optical fiber can extend off-axis from the drive shaft. The pull shaft can be coupled to the distal tip through a pull-wire connected to both the distal tip and the pull shaft. The pull shaft and pull-wire can be movable with respect to the drive shaft. The atherectomy catheter can further include an outer shaft coupled to the distal tip through a hinge mechanism. The pull shaft can be concentric with the outer shaft and be located between the drive shaft and the outer shaft. The pull shaft can be configured to deflect the distal tip without impacting the directionality of the catheter.

In general, in one aspect, an atherectomy catheter includes a catheter body, a deflectable distal tip, a rotatable cutter, and a pull-wire. The deflectable distal tip is hinged to a distal region of the catheter body at a hinge. The rotatable cutter is proximal to the deflectable distal tip. The pull-wire is mounted to the deflectable distal tip and extends proximally lateral to the cutter and hinge. The pull-wire is configured to be pulled proximally to deflect the deflectable distal tip.

This and other embodiments can include one or more of the following features. The atherectomy catheter can further include an optical fiber for OCT imaging coupled to the rotatable cutter. The optical fiber can be attached to the rotatable cutter but be otherwise free to float within the catheter body. The atherectomy catheter can further include a pull shaft extending within the catheter body and coupled to the pull-wire, and the pull shaft can be configured to pull the pull-wire proximally to deflect the distal tip. The pull-wire and pull shaft can be movable with respect to an outer shaft of the catheter body. The pull shaft can be concentric with the outer shaft. The atherectomy catheter can further include a drive shaft configured to rotate the rotatable cutter. The drive shaft can be hollow, and an optical fiber for OCT imaging can extend within the drive shaft. The pull-wire can be configured to deflect the distal tip without impacting the directionality of the catheter. The deflection of the distal tip can expose the cutter.

The present invention also relates to non-contact drive systems for driving catheter systems. For example, the catheter may include a magnetic response element that is configured to mate with a magnetic drive element that can be non-sterile and mounted outside of the sterile operating field to drive the catheter. The response element and the drive elements may be configured to provide magnetic gears that control the forward and backwards (e.g., clockwise and counterclockwise) rotation of the catheter shaft(s) and/or translation of the catheter shaft(s).

In general, in one aspect, a system for driving non-contact actuation of a shaft of a catheter includes a catheter and a driver. The catheter includes a shaft extending from a proximal end of the catheter to a distal end of the catheter and a magnetic response element attached to a proximal end of the shaft. The driver has a magnetic response element and is configured to receive the proximal end of the catheter. The magnetic response element and the magnetic drive element are configured to magnetically engage such that activation of the driver results in actuation of the shaft.

This and other embodiments can include one or more of the following features. The cutter can include a rotatable cutter. The shaft can be a drive shaft connected to the rotatable cutter. Activation of the driver can result in rotation of the drive shaft and rotation of the rotatable cutter. Activation of the driver can result in translation of the driveshaft and the rotatable cutter. The rotatable cutter can include an OCT sensor attached thereto. The shaft can be an outer shaft of the catheter. Activation of the driver can results in longitudinal translation of the outer shaft. Activation of the driver can result in rotation of the outer shaft. The response element can include magnets arranged circumferentially around a bearing, and the bearing can be attached to the shaft. The magnets can be arranged around the circumference in alternating polarities. The driver can include a rotor having magnets arranged circumferentially around the rotor. The driver can include a channel configured to hold the catheter such that the response element and driver element can engage.

In general, in one aspect, a system for driving non-contact actuation of a shaft of a catheter includes a catheter and a driver. The catheter includes a shaft extending from a proximal end of the catheter to a distal end of the catheter. The driver is configured to receive the proximal end of the catheter and actuate the shaft with a drive mechanism. The system is configured such that a sterile covering can be interposed between the drive mechanism and the shaft without preventing the driver from actuating the shaft.

This and other embodiments can include one or more of the following features. The cutter can include a rotatable cutter. The shaft can be a drive shaft connected to the rotatable cutter. Activation of the driver can result in rotation of the drive shaft and rotation of the rotatable cutter. Activation of the driver can result in translation of the driveshaft and the rotatable cutter. The rotatable cutter can include an OCT sensor attached thereto. The shaft can be an outer shaft of the catheter. Activation of the driver can result in longitudinal translation of the outer shaft. Activation of the driver can results in rotation of the outer shaft. The response element can include magnets arranged circumferentially around a bearing, and the bearing can be attached to the shaft. The magnets can be arranged around the circumference in alternating polarities. The drier can include a rotor having magnets arranged circumferentially around the rotor. The driver can include a channel configured to hold the catheter such that the response element and driver element can engage.

In general, in one aspect, a method of driving actuation of a shaft of a catheter includes: placing a sterile covering between a catheter and a driver; magnetically engaging a response element of the catheter with a drive element of the driver through the sterile covering; and activating the drive element such that a shaft of the catheter connected to the response element is actuated.

This and other embodiments can include one or more of the following features. Activating the drive element can include rotating the drive element such that the shaft is rotated. Activating the drive element can include longitudinally translating the drive element such that the shaft is longitudinally translated.

In general, in one aspect, a method of driving actuation of a shaft of a catheter includes: placing a sterile covering between a catheter and a driver; engaging a shaft of the catheter with a drive element of the driver through the sterile covering; and activating the drive element such that the shaft is actuated without contacting the drive element.

This and other embodiments can include one or more of the following features. Activating the drive element can include rotating the drive element such that the shaft is rotated. Activating the drive element can include longitudinally translating the drive element such that the shaft is longitudinally translated.

In general, in one aspect, a non-contact driver device to drive a shaft within a catheter includes a housing, a channel in the housing for receiving an end region of a catheter, and a magnetic drive element without the housing. The channel can be configured to be covered with a sterile drape so that the catheter does not directly contact the surface of the channel. The magnetic drive element can include a plurality of magnets or magnetizable elements configured to create a magnetic field within the channel and drive a magnetic response element within a catheter held in the channel.

This and other embodiments can include one or more of the following features. The plurality of magnets or magnetizable elements can be configured to create a rotating magnetic field to rotate the magnetic response element. The plurality of magnets or magnetizable elements can be configured to translate longitudinally to move the magnetic response element longitudinally. The magnetic channel can be a crevice configured such that the end region of the catheter can be placed on top of the crevice. The driver can further include a rotor having magnets arranged circumferentially around the rotor. The magnetic drive element can be configured to create a dynamic magnetic field within the channel to drive rotation of the magnetic response element.

Also described herein are stylets, and more specifically stylets used to cross occlusions and/or to re-enter a true lumen of a vessel.

In general, in one embodiment, a stylet for re-entry into a vessel includes an elongate body including a proximal portion, a middle curved portion, a pointed distal end, and a longitudinal axis extending through the proximal portion, the middle curved portion, and the pointed distal end. The proximal portion and the middle curved portion have substantially circular cross-sections. The middle curved portion has a pre-shaped curve along the longitudinal axis configured to match a curve of an occlusion-crossing device. The pointed distal end has an s-curve along the longitudinal axis and a flattened portion along the longitudinal axis, the flattened portion having a substantially oblong cross-section.

This and other embodiments can include one or more of the following features. The s-curve can be within the flattened portion. At least one of the distal end or the middle curved portion can include nitinol. The proximal portion can include stainless steel. The pre-shaped curve can form an angle of 130 to 170 degrees. The angle can be approximately 150 degrees. The s-shaped curve can have two curves, the first curve can form a first angle of 120 to 160 degrees and the second curve can form an angle of 120 to 160 degrees. The s-shaped curve can have a first curve and a second curve, the second curve distal to the first curve, and the pre-shaped curve can be aligned in substantially the same direction as the second curve. The pointed distal end can include an anchor. The curved middle portion can be preset to mimic a set bend in an occlusion-crossing catheter.

In general, in one embodiment, a method of re-entering a true lumen during occlusion-crossing includes orienting a distal end of a catheter having a bend therein towards the true lumen of a vessel; introducing a stylet through a guidewire channel of the catheter until a curved middle portion of the stylet aligns with the bend in the catheter and a pointed distal end of the stylet extends out of a distal end of the catheter; advancing the stylet such that the pointed distal end pierces through a wall of the vessel; and directing the catheter over the stylet and into the true lumen of the vessel.

This and other embodiments can include one or more of the following features. The method can further include orienting the stylet within the catheter such that the pointed distal end of the stylet curves sharply towards the vessel wall before advancing the stylet. The method can further include reorienting the catheter within the true lumen after directing the catheter of the stylet. Reorienting the catheter can include reorienting without puncturing an opposite vessel wall. The method can further include determining an orientation of the stylet based upon an alignment of the curved middle portion with the bend in the catheter. The catheter can further include a proximal portion, the proximal portion and the curved middle portions can have substantially circular cross-sections, and the pointed distal end can have a flatted portion and can have a substantially oblong cross-section. The method can further include using image guidance to orient the catheter.

In general, in one embodiment, an assembly for re-entry into a vessel includes a catheter and a stylet. The catheter includes a pre-set curve. The stylet includes an elongate body having a proximal portion, a middle flexible portion, and a distal stiff portion. When the stylet is inserted into the catheter, the flexible portion is configured to conform to the pre-set curve and the distal stiff portion is configured to at least partially straighten the pre-set curve. The flexible portion has a length such that the flexible portion can align with the pre-set curve both while the distal stiff portion remains inside the catheter and while the distal stiff portion extends distally from a distal end of the catheter.

This and other embodiments can include one or more of the following features. The distal stiff portion can include a sharp pointed end. The middle flexible portion can include a flexible coil. The proximal portion can be stiffer than the middle flexible portion.

In general, in one embodiment, an assembly for re-entry stylet for re-entry into a vessel includes a catheter and a stylet. The catheter includes a pre-set curve. The stylet includes a flexible elongate body having a pointed distal end. The stylet further includes a stiff tube concentric with the flexible elongate body, the flexible elongate body axially movable relative to the stiff tube. When the stylet is inserted into the catheter, the flexible portion is configured to conform to the pre-set curve, and the flexible elongate body is configured to at least partially straighten the pre-set curve.

This and other embodiments can include one or more of the following features. The flexible elongate body can include a pre-set curve configured to match the pre-set curve of the catheter. The flexible elongate body can include a shape memory material.

In general, in one embodiment, a stylet for re-entry into a vessel includes an elongate body having a pointed distal tip. The stylet includes a coiled member attached to the pointed distal tip. The coiled member includes a relaxed configuration where the coiled member extends over the pointed distal portion and a compressed configuration wherein the coiled member is compressed to expose at least a portion of the pointed distal tip.

Methods of using the stylets to reenter a lumen, such as for occlusion crossing, are also described herein.

BRIEF DESCRIPTION OF THE DRAWINGS

FIGS. 2A-2B show the exemplary device of FIG. 1 in an inactive or closed configuration (with the distal tip covering or protecting the cutting edge of the cutter) and in an open configuration (with the distal tip deflected to expose the cutting edge of the cutter), respectively.

in FIG. 5B some elements have been removed to more clearly show the ramped slide surface between the distal tip and a region of the catheter proximal to the cutter. Pushing or pulling on the actuator (e.g., a drive shaft) proximally/distally may deflect the distal tip region out of the longitudinal axis relative to the rest of the catheter immediately proximal to the distal tip region.

in FIG. 7B some elements have been removed to ore clearly show the ramped slide surface.

FIGS. 8A and 8B show side and end views, respectively, of a more distal region of the catheter, partially cut away to illustrate two drive shafts, one for controlling rotation of the cutter, surrounding one for controlling rotation of the imaging sensor (e.g., OCT fiber).

FIG. 9A shows one variation of a handle for an atherectomy catheter as described herein; FIG. 9B shows a perspective view of an accessory device for holding the catheter and/or a guidewire.

FIGS. 19A and 19B show two variations of imaging guidewires and illustrate an alternative optical fiber management technique that may be used.

FIGS. 35A-35E show an exemplary atherectomy catheter having a pull-wire activation mechanism for deflection of the distal tip.

FIGS. 36A-36B show transparent and cross-sectional views of the atherectomy catheter of FIGS. 35A-35B;

FIG. 37A shows a handle used to control the pull shaft of the catheter of FIGS. 35A-36B. FIG. 37B is a cross section of the handle shown in FIG. 37A.

FIGS. 41A-41K illustrate an exemplary atherectomy catheter that can be used with the non-contact drive systems or pull-wire mechanisms described herein.

FIG. 43A is a side view of the distal end of an exemplary directional re-entry stylet.

FIG. 43B is a close-up of the distal tip of the directional re-entry stylet of FIG. 43A.

FIG. 44A is a schematic of a directional re-entry stylet such as the one shown in FIG. 43A.

FIG. 44B is a close-up of the distal tip shown in FIG. 44A.

FIG. 44C is a close-up of the junction shown in FIG. 44A.

FIG. 45A is a schematic of an exemplary aligning re-entry stylet having a central flexible section.

FIG. 45B is a close-up of the flexible section of the aligning re-entry stylet of FIG. 45A.

FIG. 46A shows the re-entry stylet is aligned within the device such that the angle of the pre-set curve is not changed by the stylet. FIG. 46B shows the exemplary CTO crossing device straightened using the re-entry stylet. FIG. 46C shows the exemplary CTO crossing device with the re-entry stylet extending from the distal end.

FIG. 49A shows the stylet placed such that both the outer tube and the inner elongate body are proximal of the pre-set curve. FIG. 49B shows the outer tube moved distal to the pre-set curve such that the pre-set curve is straightened. FIG. 49C shows the outer tube positioned proximal to the pre-set curve and the inner elongate body extended out the distal end of the catheter. FIG. 49D shows the outer tube moved distal to the pre-set curve such that the pre-set curve is straightened and the inner elongate body extended out the distal end of the catheter.

FIG. 52A shows a spring-loaded stylet in passive mode. FIG. 52B shows a spring-loaded stylet in active mode.

FIG. 54A shows the stylet pointing out of the catheter. FIG. 54B shows the stylet piercing through the vessel wall. FIG. 54C shows the catheter reentering the true lumen over the stylet. FIG. 54D shows the catheter reoriented within the true lumen.

FIG. 55A shows the stylet piercing the vessel wall. FIG. 55B shows the catheter reentering the true lumen over the stylet. FIG. 55C shows the catheter reoriented within the true lumen.

FIG. 56A shows the stylet within the catheter. FIG. 56B shows the stylet piercing the wall. FIG. 56C shows the catheter reentering the true lumen over the stylet. FIG. 56D shows the stylet straightening the catheter to reorient it within the true lumen.

DETAILED DESCRIPTION OF THE INVENTION

Figure 1:
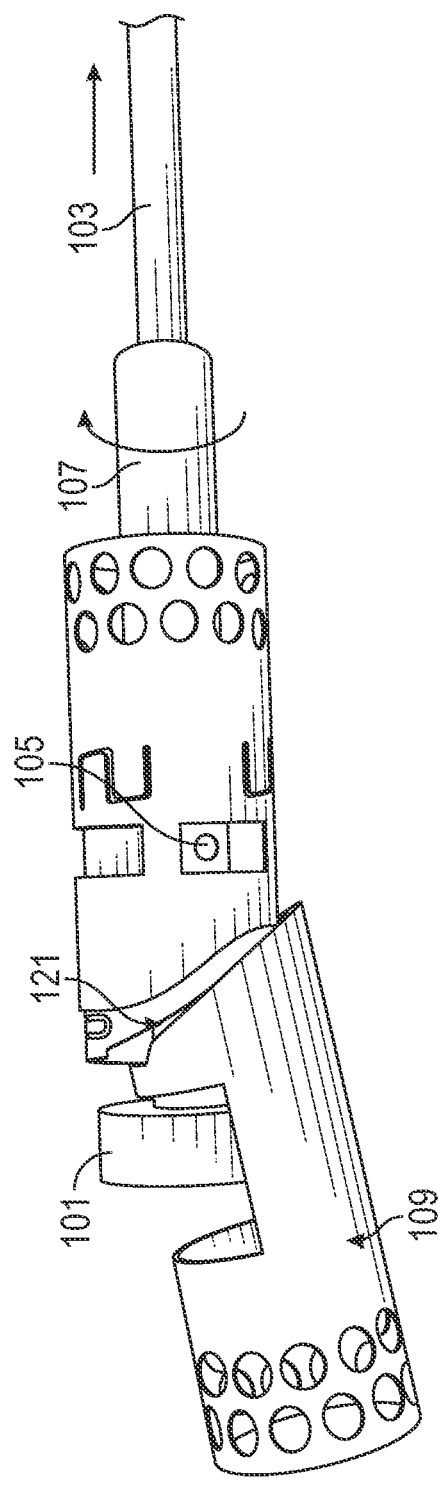
FIG. 1 shows one variation of a portion of an atherectomy catheter for both cutting and/or imaging within a vessel. This variation has a longitudinally displaceable distal tip region; the distal tip may be displaced by pushing or pulling (e.g. proximally/distally) an actuator within the catheter and thereby expose a cutting edge of the rotational cutter.

In general the atherectomy devices described herein include one or more cutters configured to cut tissue that are actuated by longitudinal motion of a drive shaft. By "actuation" the cutter may be exposed to the tissue so that it may cut. The cutting drive shaft may be rotatable as well and may also move longitudinally (e.g., forward and backwards along the long axis of the catheter). The longitudinal motion to expose the cutter may be controlled manually or automatically, and may cause deflection of the distal tip region out of the axis of the more proximal region of the catheter; in some variations it may move the catheter laterally out of the long axis of the catheter. Typically any of these catheters may also include an imaging system for imaging the walls (and into the walls) of the vessel, e.g., using an off-axis OCT imaging system that rotates at a much slower rate around the perimeter of the catheter than the cutting edge rotates for cutting. Thus, in some variations, the device an elongate catheter body, and a rotatable OCT imaging element having a fiber optic extending off-axis within the elongate catheter body. In some variations the catheter body also contains two drive shafts: an imaging drive shaft and a cutting drive shaft. The two drive shafts may be concentrically arranged, while the imaging drive shaft rotates at a much lower speed (and in alternating directions) compared to the cutting drive shaft.

In variations having two drive shafts, both drive shafts may be a flexible; the cutting drive shaft in particular may have sufficient column strength to push or pull to activate the rotating cutter by longitudinally moving (e.g., a slight longitudinal movement) proximally-to-distally along the longitudinal length of the catheter. In some variations the longitudinal movement of the cutting drive shaft deflects the distal tip away from (or back to) the long axis of the more proximal region of the catheter, exposing the rotating cutter and allowing it to cut. In other variations the longitudinal movement of the drive shaft pushes or drives the cutting element away from the long axis of the catheter, exposing the cutting edge to allow cutting. The driving movement does not need to be substantial (e.g., a few millimeters of movement may be sufficient). The catheter may also include a longitudinal lock to hold the catheter with the cutting element exposed.

Described herein are variations of atherectomy devices having longitudinal actuators.

For example, FIGS. 1-10 illustrate variations of atherectomy catheters including both a rotational cutter and imaging sensor. The devices shown in FIGS. 1-10 typically include one or all of the following features: rotating cutter located proximal to a deflectable distal tip, an imaging sensor, and at least one drive shaft configured to rotate the cutter; a separate drive shaft may also be used to rotate the imaging element. In some variation one or both drive shafts may also be used to actuate displacement of the distal tip and therefore expose the cutter. Other features are described below in the specific examples; it should be understood that these features may be generally used in combination with any of the other features described.

Cutter

Any appropriate cutter may be used. Typically the cutter is a ring or partial ring cutter that is rotated by connection with a cutting drive shaft. The cutting drive shaft rotates to drive rotation of the cutter. One or more edges of the ring may be configured to cut. For example, the cutter may include at least one cutting edge that is typically not exposed until the distal tip region is deflected out of the way. The cutting edge may be sharp, smooth, serrated, etc. In some variations the cutting edge is configured to face distally. The cutter may be made of any appropriate material, including a metal, ceramic, polymeric, or composite material, or the like.

When not exposed, a portion of the cuter may form a portion of the outer surface of the catheter; for example, a side wall of the cutter may form a portion of the outer surface of the catheter.

Distal Tip Region

The distal tip region is configured to deflect to expose the cutting surface of the cutter. The distal tip region may be hollow or otherwise configured to hold material cut by the atherectomy device. In some variations the distal tip region is clear or at least partially transparent, allowing one to see if material has been collected or remains in the tip region. The distal tip region may include a flush port or may otherwise be adapted to allow removal of cut material stored therein. For example, the distal end may be tapered but may be open. The distal tip region may be removable and/or replaceable. A reusable locking mechanism, such as threads, or the like, may be used to secure a distal tip region on the catheter.

In some variations the distal tip region is relatively stiff; in other variations the distal tip region is flexible, and may be formed of a soft or resilient material. For example, the distal tip region may be a mesh or woven material.

In general, the distal tip region is deflectable. Typically, the distal tip region is deflectable so that it is displaced away from the axis of the catheter, thereby exposing the cutter. The cutter therefore remains in the same radial position both in active and inactive configurations, while the distal tip region is deflected. For example, the distal tip region may be deflected off-axis of the long axis of the catheter; thus, the distal tip region may be dropped radially away from the longitudinal axis of the catheter. The distal tip may also or alternatively be angled away from the rest of the catheter (e.g., the region of the catheter proximal to the distal tip region).

Typically, the interface between the distal tip region and the rest of the catheter may be configured as a ramped slide surface. This slide surface is angled relative to a plane perpendicular through the long axis of the catheter, though the direction of the angle determine if the distal tip region is deflected by pushing or by pulling the actuator (e.g., the cutting drive shaft). The ramp ramped slide surface is configured to guide deflection of the distal tip as the cutter drive shaft is moved longitudinally.

Imaging Sensor

Any of the catheters described herein may include an imaging sensor. The imaging sensor may be, in some variations, configured to rotate independently of the rotating cutter to allow visualization of the vessel. An imaging sensor may rotate independently of the rest of the catheter, including the cutter. In some variations, the cutter may rotate at a much faster rate (10×-100× faster) than the imaging sensor. The imaging sensor may also rotate in more than one direction (e.g., first clockwise for some number of rotations, then counterclockwise for some number of rotations). In contrast, the cutter may be configured to rotate in a single direction.

In general, an imaging sensor captures images of the lumen, or into the wall of the lumen. The imaging sensor may provide real-time images from before, during and/or after cutting when used as part of an atherectomy device. In any of the variations described herein the imaging sensors may be OCT imaging sensors. An OCT imaging sensor may include an optical fiber, a mirror to direct the light into the tissue and back into the fiber for processing. The sensor may therefore include an optical fiber. This fiber may be held off-axis within the catheter. The distal end (e.g., imaging sensor end) of the optical fiber may be secured to allow rotation of the distal end of the fiber, while the region between the proximal end (which may be fixed) and the distal end (which may be fixed to a rotating head) is allowed to rotate somewhat freely within the catheter body, and therefore to wind and unwind around within the catheter body as the imaging sensor end is rotated. As mentioned, the distal end of the optical fiber may form an imaging sensor that may include a mirror to allow imaging of the inside of a vessel as the imaging sensor is rotated. The unrestrained optical fiber may be held in a channel, passage, tube, or other structure that constrains its ability to kink or knot up on itself as it is rotated. In some variations the optical fiber may be configured to wrap around a wire, shaft, tube, or the like. In some variations, the optical fiber does not wrap around anything, but twists on itself. In general, systems including optical fibers may limit the number of rotations clockwise and counterclockwise, and may alternate between clockwise and counterclockwise rotation to allow continuous imaging when desired.

Drive Shafts

As mentioned, the devices may include a drive shaft for controlling rotation of the cutter, and (in some variations) a separate drive shaft for controlling rotation of the imaging sensor. For example, a cutting drive shaft may be connected to the rotatable cutter and may also be coupled to a drive (e.g., motor) in proximal end of the catheter such as the handle to drive rotation of the cutter. A separate imaging drive shaft may be coupled to the imaging sensor for driving rotation of the imaging sensor. In some variations a drive shaft, such as the cutting drive shaft, may also be used to actuate deflection of the distal tip region.

An alternate variation of the devices described herein may include a single drive shaft that rotates from which rotation of both the cutter and the imaging sensor may be achieved. For example, the distal end may include gears for stepping down (or up) the rotation rate of the drive shaft to drive rotation of either the cutter or imaging element. In addition, in some variations a separate actuator may be used to control deflection of the distal tip region. For example, the distal tip region may be deflected by a tendon or other member (e.g., a member having a high column strength) extending the length of the catheter.

EXAMPLES

Figure 3A:
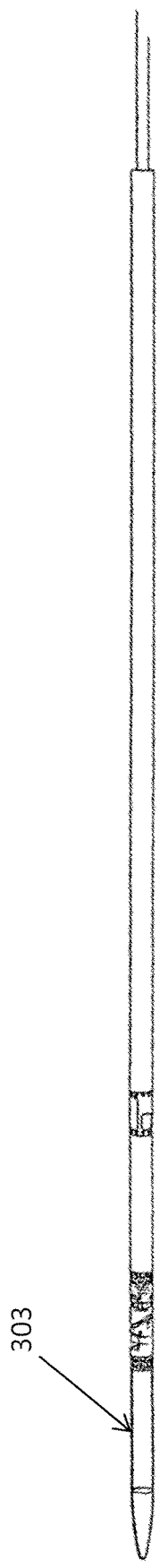
FIG. 3A shows another view of the distal portion of a catheter such as the one shown in FIGS. 1-2B. This example shows the distal tip region which is absent in FIGS. 1 and 2A-2B.
Figure 3B:
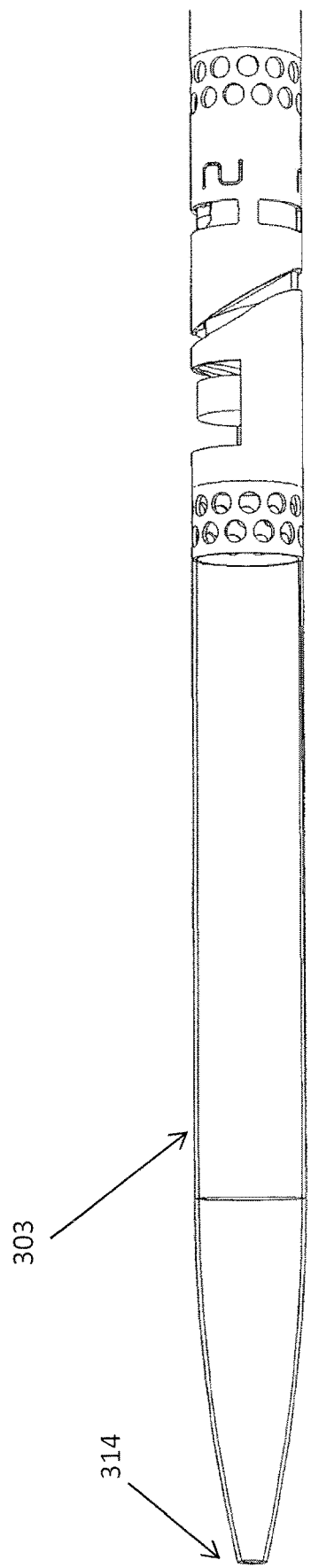
FIG. 3B shows an enlarged view of the distal end region of FIG. 3A.

FIGS. 3A and 3B show one variation of an atherectomy catheter that includes both a rotating cutter and a rotating imaging sensor. In this variation the cutter and imaging sensor may be rotated separately, and the distal tip region may be displaced to expose the cutting edge of the cutter, allowing material to be removed. OCT images may be collected continuously (in a 360 degree view) before, during, or after cutting. In this variation the cutter is positioned distally to the imaging sensor. The distal tip region may be displaced by applying pulling (or in some variations pushing) force to the drive shaft of the cutter, which displaces the distal tip region. Moving the drive shaft laterally (e.g., proximally or distally) to displace the distal tip does not otherwise effect the operation of the cutter, which may continue to rotate. This may allow the distal tip region to help control the thickness of slices cut from the tissue by controlling the amount that the cutting edge is exposed.

Referring now to FIG. 1, FIG. 1 shows a portion of one variation of an atherectomy catheter configured for both cutting and/or imaging. The portion illustrated in FIG. 1 is the hinge region between the distal tip region (not shown) and the more proximal elongate region of the atherectomy catheter. FIG. 1 shows a rotatable cutter 101 coupled to a cutting drive shaft 103. The drive shaft may be rotated to move the cutter. The device also includes an imaging sensor 105 that is coupled to an imaging drive shaft 107. The imaging drive shaft may be rotated to rotate the imaging sensor, and may be rotated independently of the cutter and cutter drive shaft. In this example, the imaging drive shaft coaxially surrounds the cutter drive shaft.

The distal tip region 109 (which may include a distal tip region chamber for holding material removed by the device as shown in FIG. 3A and 3B), is shown deflected downwards and slightly off-axis, exposing the rotating cutter 101. In this example, the distal tip region may be deflected by pulling proximally on the cutter drive shaft 103, as indicated by the right-pointing arrow above the cutter drive shaft. Pulling the cutter drive shaft forces the distal tip region against the angled face of the ramped slide surface 121 formed between the proximal end of the catheter and the distal end region. This ramped slide surface may be configured so that the distal tip region first drops "down," e.g., displaces longitudinally but remains substantially parallel to the elongate body of the catheter. In some variations, with the application of continued pulling (or in some variations pushing) the distal tip region bends at an angle away from parallel with the rest of the catheter, as shown.

FIGS. 2A and 2B illustrate the same region of the device of FIG. 1 in both a non-cutting configuration and a cutting configuration, respectively. In the non-cutting configuration, the catheter extends along a single longitudinal axis (which may be curved, as the catheter is flexible), and the cutting edge of the cutter is not exposed to the tissue. The cutter may be rotated, but rotation will not typically cut tissue until the distal tip region is moved out of the way, as shown in FIG. 2B. In FIG. 2B, the distal tip region 109 is shown deflected away from the cutting edge 203. Typically, once the distal tip region 109 is deflected to expose the cutting edge, no additional force is necessary on the cutting drive shaft (or other actuator) to keep the cutting edge exposed.

Returning now to FIG. 3A, the distal end region (including a chamber for holding cut tissue 303) of an atherectomy catheter including the cutter, hinge region and imaging sensor shown in FIGS. 1-2B are shown. FIG. 3B shows an enlarged view of the distal end of the device of FIG. 3A. In this example, the distal end region 303 may be configured as hollow and may be used to store material cut by the atherectomy device. As the device is advanced with the cutter exposed, material cut may be pushed against the inside surface of the rotating cutter and may then be deflected back into the hollow distal tip region. The distal tip region may also include an opening 314. A proximal handle or handles to control the catheter (including the imaging sensor and/or cutter) is not shown in FIGS. 3A or 3B, but is described below.

Figure 4A:
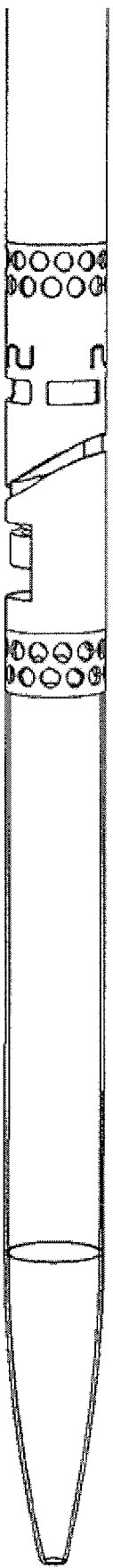
FIGS. 4A-4C show different rotational views of the distal region of an atherectomy catheter configured for both visualization and/or cutting.
Figure 4B:
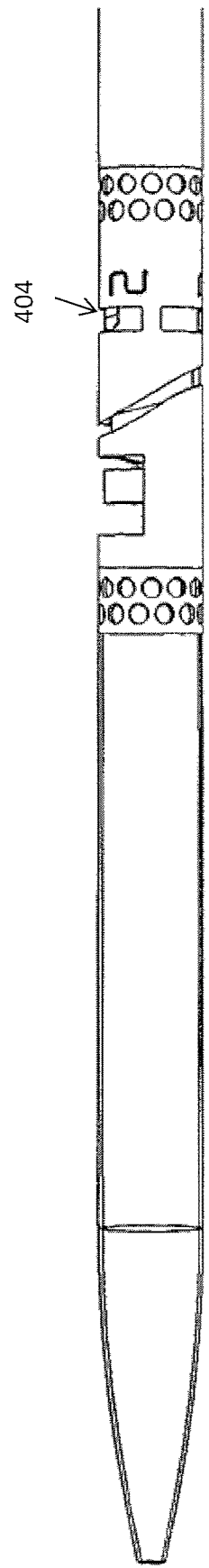
Figure 4C:
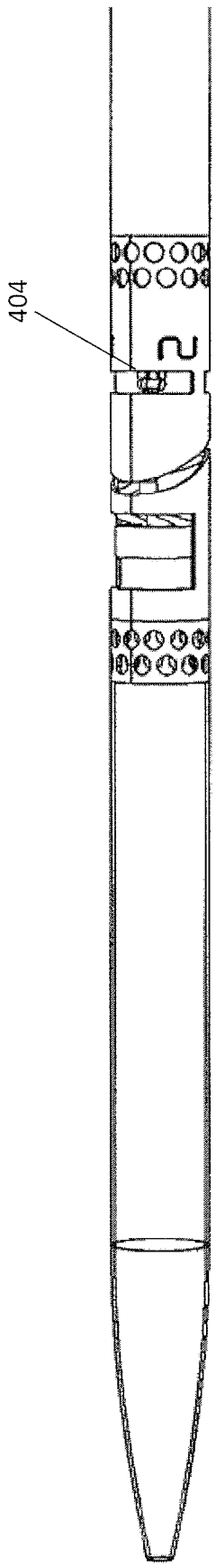

FIGS. 4A-4C illustrate a distal end region of this variation of the device, from different views than those shown in FIGS. 3A and 3B. For example, In FIG. 4C, the imaging element 404 is configured as an OCT imaging sensor element as previously described. In this embodiment, the imaging sensor include the distal end of the optical fiber that is fixed to a rotatable chassis including a mirror for directing the optical signal out from the catheter and into the walls of the vessel. In some variations the imaging element is directed out at 90 degrees from the catheter (looking laterally); in other variations the imaging element is configured to look forward or slightly forward, or backwards. The imaging sensor may also be configured to rotate completely around the perimeter of the catheter, as illustrated in FIGS. 1-4C. The imaging sensor may be configured so that the end of the optical fiber is secured fixed (e.g., epoxied) into position on a rotatable chassis (not visible in FIGS. 3A-4C. A surrounding housing, which may form part of the outer catheter wall, may include one or more windows or viewports through which imaging may occur. These viewports may be separated into discrete regions, and the separators may also act as fiduciary markers, particularly when arranged in a non-rotationally symmetric configuration. For example, the viewports may be formed by holes in the outer catheter shaft separated by 90°, 90° and 180°. Thus, as the imaging sensor is rotated, the view may be periodically interrupted by separators at 0°, 90°, 270° and again back at 0°/360°. Such separations may therefore be used to indicate the orientation of the catheter within the body.

As mentioned, the catheter may be configured so that the imaging sensor is sequentially rotated both clockwise and counterclockwise. For example, the imaging sensor may be configured so that after a number of rotations clockwise, the imaging sensor is then rotated counterclockwise for the same number of rotations, and this cycle may be repeated. In variations in which the imaging element is an off-axis optical fiber, the fiber may therefore wind and unwind around the inside of the catheter (e.g., around the drive shaft or shafts, in some variations).

Figure 4D:
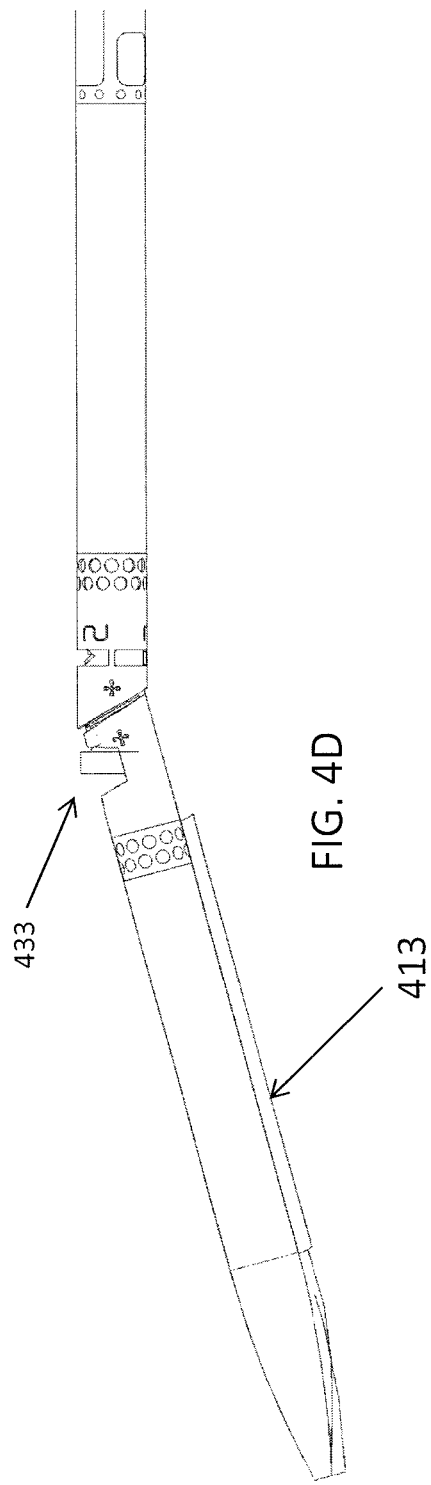
FIGS. 4D and 4E show the catheter of FIGS. 4A-4C with the cutter exposed by deflecting the distal tip region; this variation also include a guidewire channel (e.g., guidewire exchange channel) that may be included in any of these catheter variations.
Figure 4E:
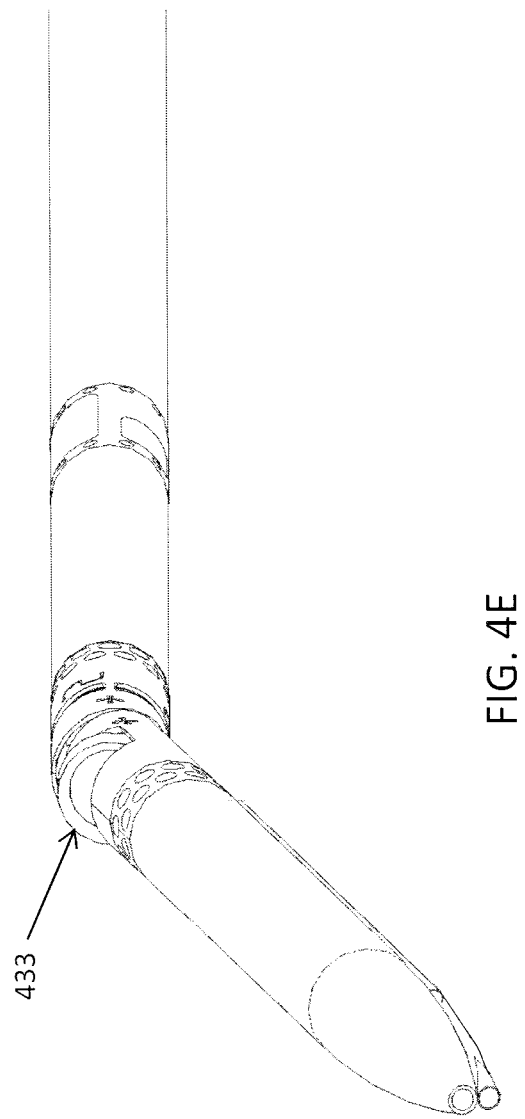
Figure 4F:
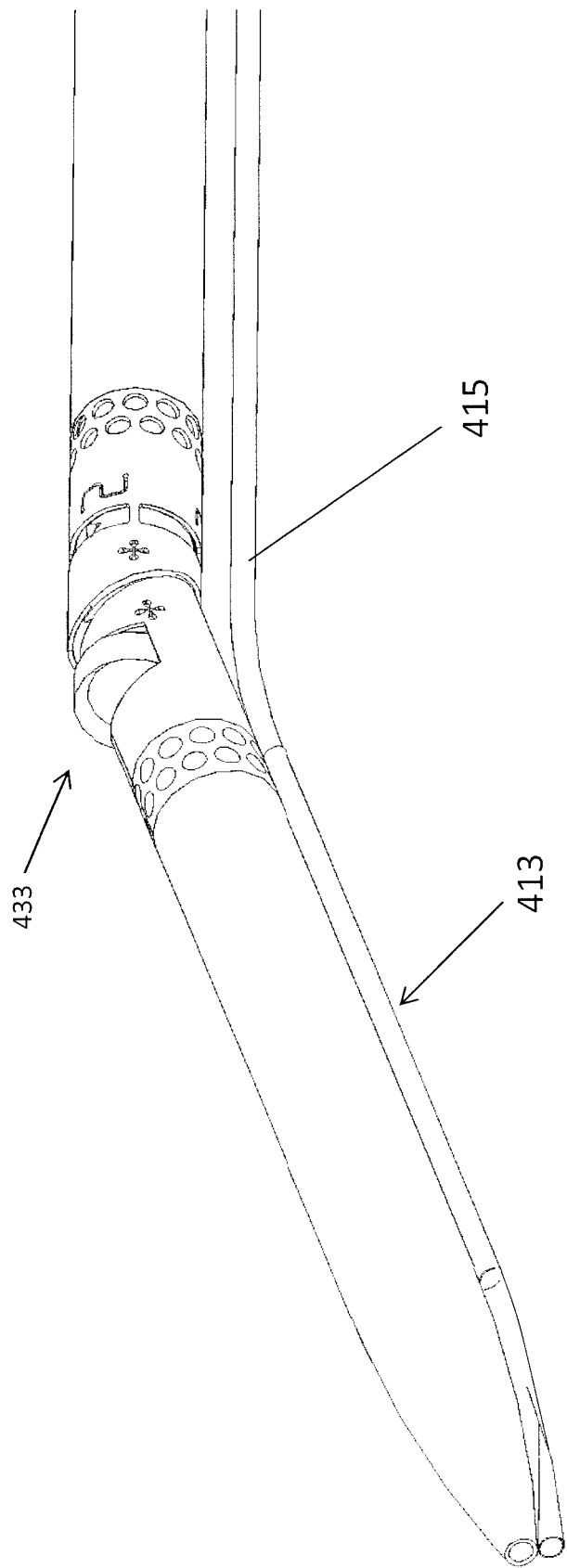
FIG. 4F shows a variation in which a guidewire is present within the guidewire channel.

FIGS. 4D-4F show side perspective views of the atherectomy device variation shown in FIGS. 4A-4C in which the distal tip region has been displaced as discussed above. In these variations the catheter is also shown with a guidewire attachment region 413 into which a guidewire 415 may be threaded, as illustrated in FIG., 4F. Thus, the catheters described herein may be used with a guidewire 415 that has been placed within the body, including across an occluded region. The guidewire attachment region may be a rapid exchange type connection.

FIG. 4E shows a proximally-looking view of the catheter, showing the cutting region exposed by displacing the distal tip down and bending away from the long axis of the catheter. The side of the cutting opening formed 433 may be regulated by how much the drive shaft (e.g., the cutter drive shaft) is pushed or pulled distally/proximally, and therefore how much the distal tip is displaced. The catheter may be configured to lock the proximal/distal position of the drive shaft and therefore maintain a selected cut opening size.

Figure 5A:
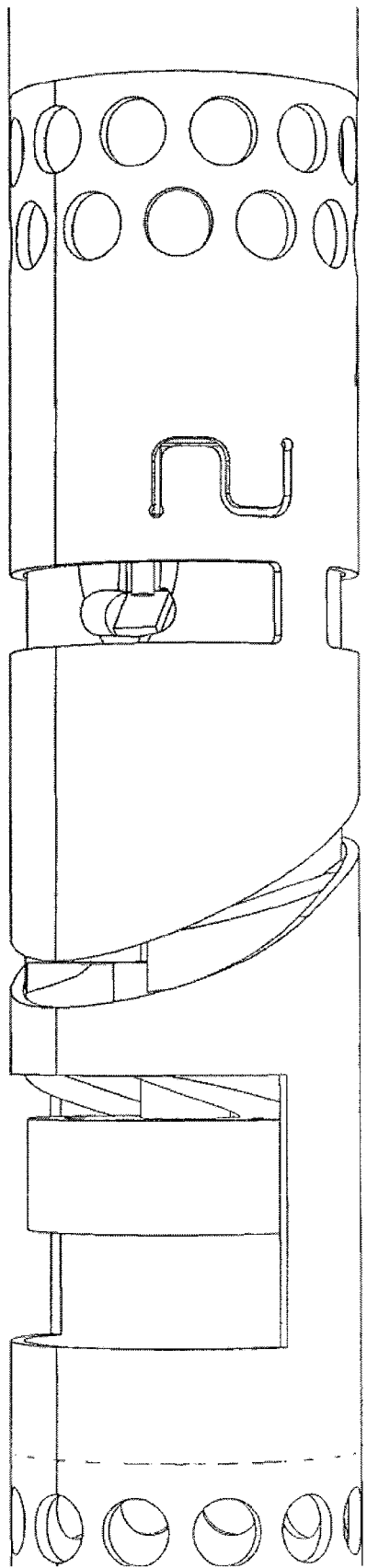
FIGS. 5A and 5B show another view of the hinged region of the catheter shown in FIGS. 4A-4C.
Figure 5B:
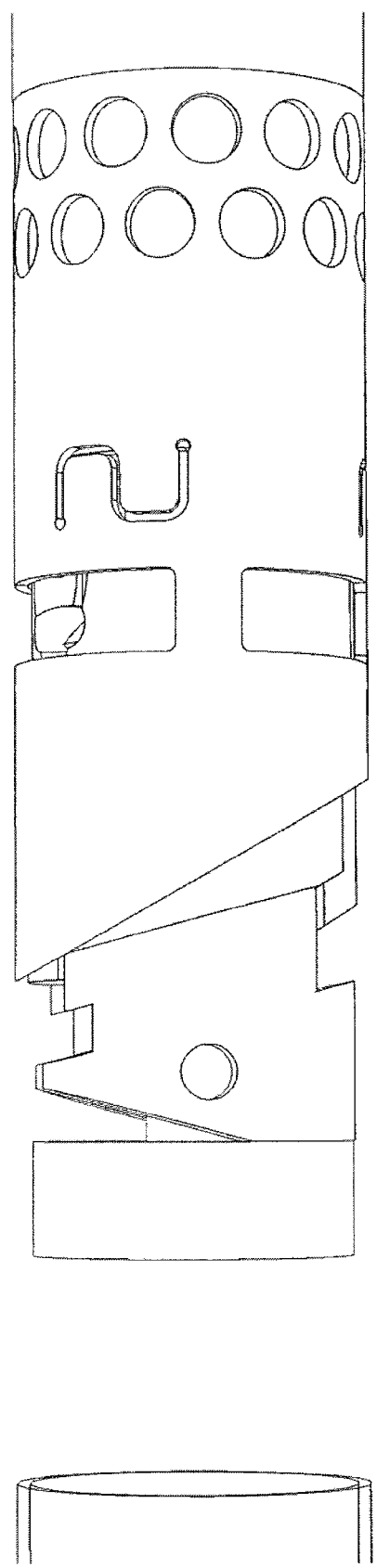
Figure 6A:
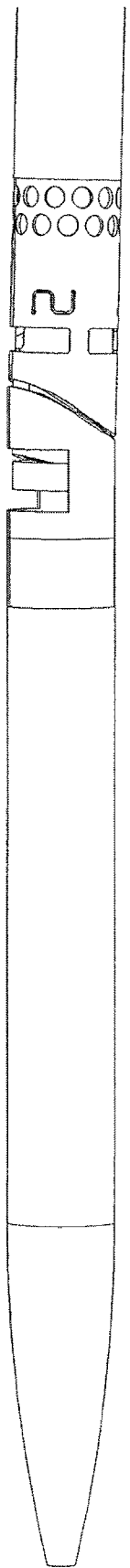
FIGS. 6A and 6B illustrate another variation of a catheter device in which the ramped slide surface extends in the opposite direction from the device shown in FIGS. 5A and 5B.
Figure 6B:
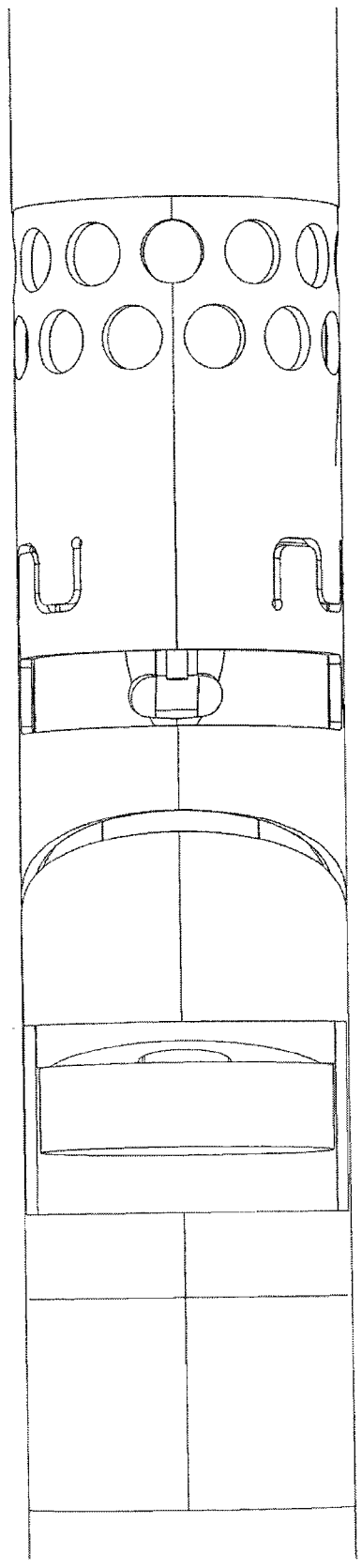
Figure 7A:
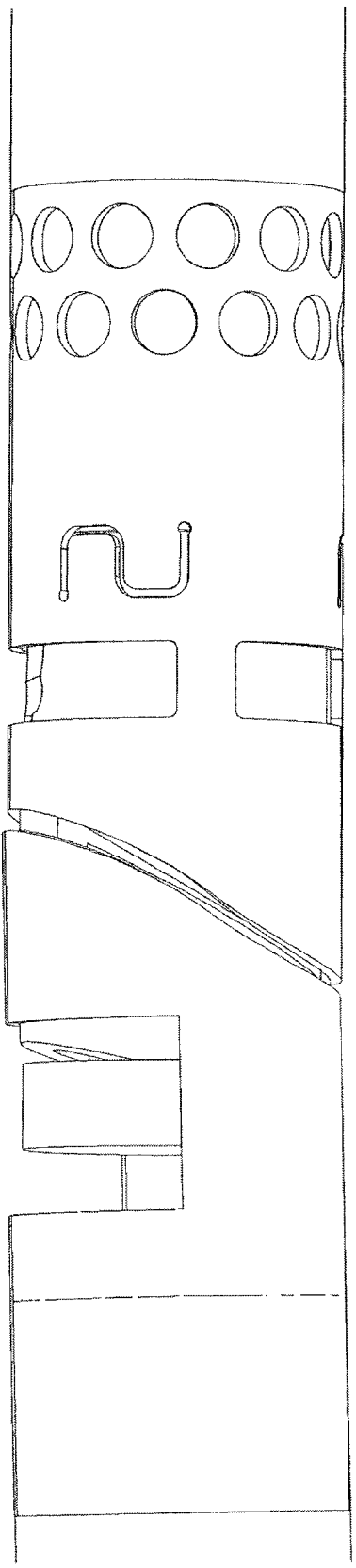
FIGS. 7A and 7B show another view of the hinged region of the catheter shown in FIGS. 6A and 6B.
Figure 7B:
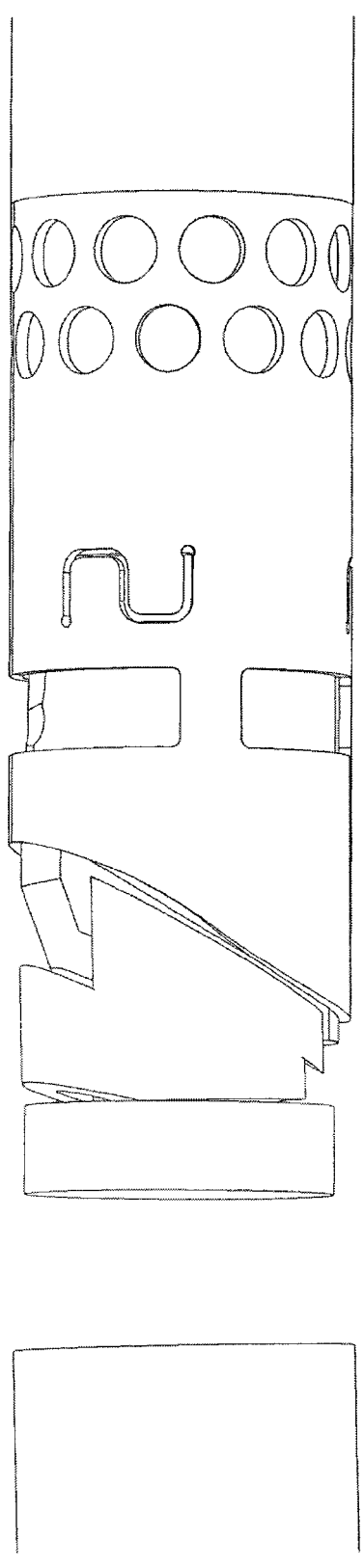

FIGS. 5A and 5B show a slightly enlarged view of a hinge or pivoting region of an implant such as those illustrated above, showing the cutter, imaging sensor and the ramped slide surface. As used herein, a ramped slide surface may be a cam surface, and may include any surface or interface between the two regions of the catheter in which longitudinal force (e.g. pushing or pulling) from one end of the implant results in radial displacement of the distal tip region, exposing the cutting edge of the cutter.

As mentioned, an atherectomy catheter such as the one shown in FIGS. 1-4F above may be configured so that the distal tip region is displaced either by pushing or by pulling an actuator. In many of these examples the actuator is a drive shaft, though other actuators may be used, including the imaging drive shaft, and/or a dedicated actuator, which may be a cable, shaft, or the like. FIGS. 1-4F illustrate a variation in which the distal tip region is displaced (revealing the cutting edge) by pushing the cutting drive shaft distally, and replacing the distal tip region (protecting the cutting edge) by pulling proximally on the cutting drive shaft. Other variations, such as those described in FIGS. 6A-7B are configured to displace the distal end and form a cutting opening by pulling an actuator (e.g., the drive shaft) proximally and restoring it to an original position by pushing the actuator distally.

As may be seen by comparison, for example, of FIGS. 7A and 7B to FIGS. 5A and 5B, altering the actuator direction in this manner may be achieved by changing the direction of the ramped slide surface, and in some variations, the addition of structures to translate the actuator force into displacement. For example, in FIGS. 6A-7B, the ramped slide surface is angled in an opposite orientation from that shown in FIGS. 4A-5B.

In general, in the atherectomy device variations illustrated in FIGS. 1-7B, the imaging sensor and the rotating cutter are driven separately, using separate drive shafts. Other variations, in which the imaging senor and cutter are rotated together are also contemplated and described below. In some variations, the rotation of the imaging sensor is dependent upon (e.g., based on) the rotation of the cutter.

FIGS. 8A and 8B show partial views of the more proximal region of an atherectomy catheter, showing the arrangement of the outer imaging drive shaft 801 surrounding an inner cutter drive shaft 803; the two drive shafts may be rotated independently. In some variations the inner drive shaft may be separated from the outer drive shaft at least along a portion of its length by a lubricant or lubricious material. A lubricant may be or may include water. FIG. 8B shows an end view of the proximal end, looking down the shaft; the fiber optic 804 may wrap in the space 811 between the inner drive shaft 803 for the cutter and the outer drive shaft 801 for the imaging sensor. The distal end of the optical fiber 804 is glued to a rotating chassis (not visible) along with the mirror 809 (the outer drive shaft 801 has been made partially transparent in this view. Thus, in this variation the distal end of the optical fiber is secured to the rotatable chassis and the proximal end of the optical fiber (not shown) is secured to the handle, while the intermediate region between the two ends is allowed to wrap within the catheter.

Any of the variations described herein may also include a rinse or flush port that is located near the imaging sensor to allow fluid (e.g., saline) to be flushed from the catheter to clear debris or red blood cells (which may otherwise occlude or degrade the field of view). For example, fluid may be pressurized and released from the region of the catheter near the imaging sensor to rinse the imaging sensor. This rinse may occur continuously or when controlled by the user. For example, fluid from between the two drive shafts may be pressurized to flush the imaging sensor. The rotatable imaging chassis may be configured with one or more flush ports for this purpose; the proximal end region of the catheter may include a port for applying and/or pressurizing fluid.

Figure 10:
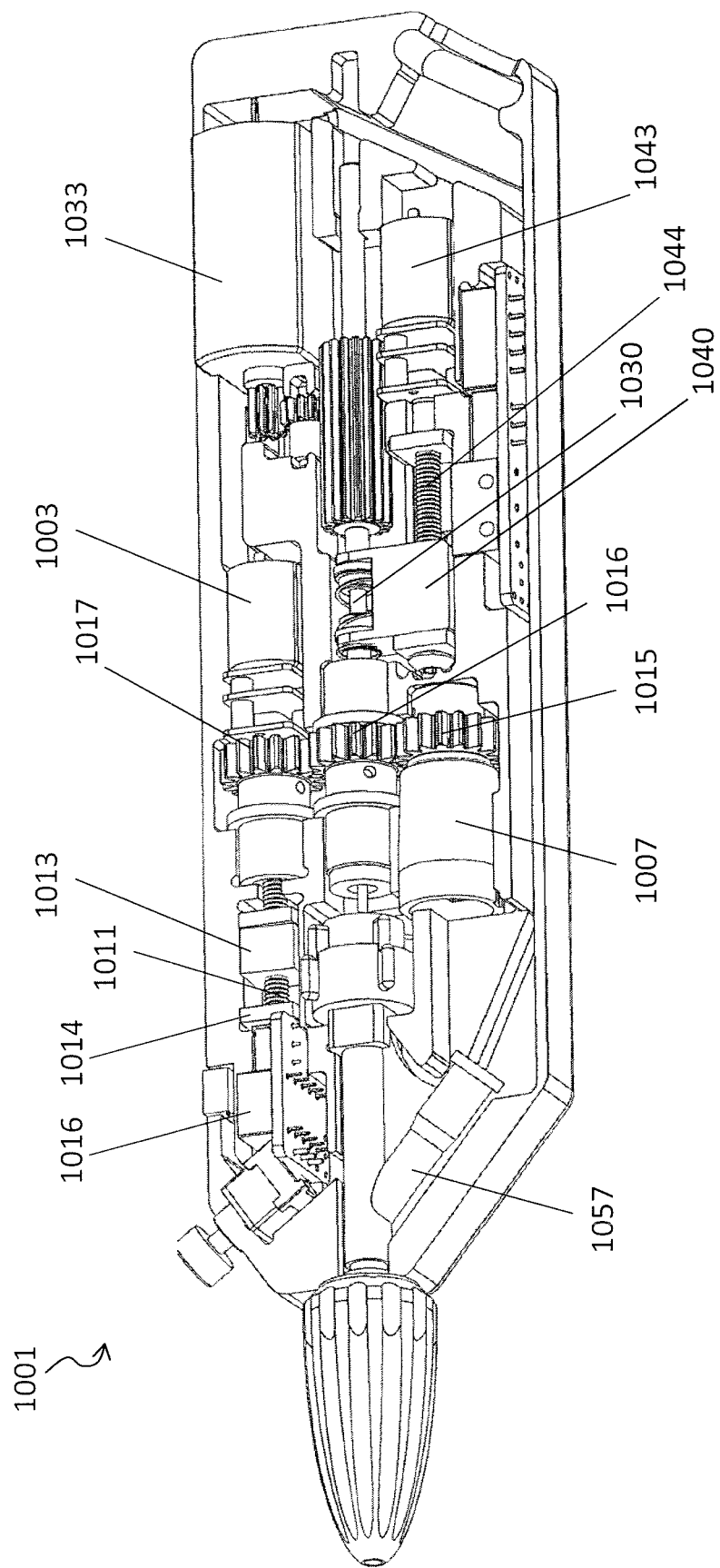
FIG. 10 shows a side perspective view of the handle shown in FIG. 9A, in which the outer covering has been removed to illustrate some of the internal features, including two separate driver (e.g., motors) for rotating the cutter and imaging sensor, respectively.
Figure 11:
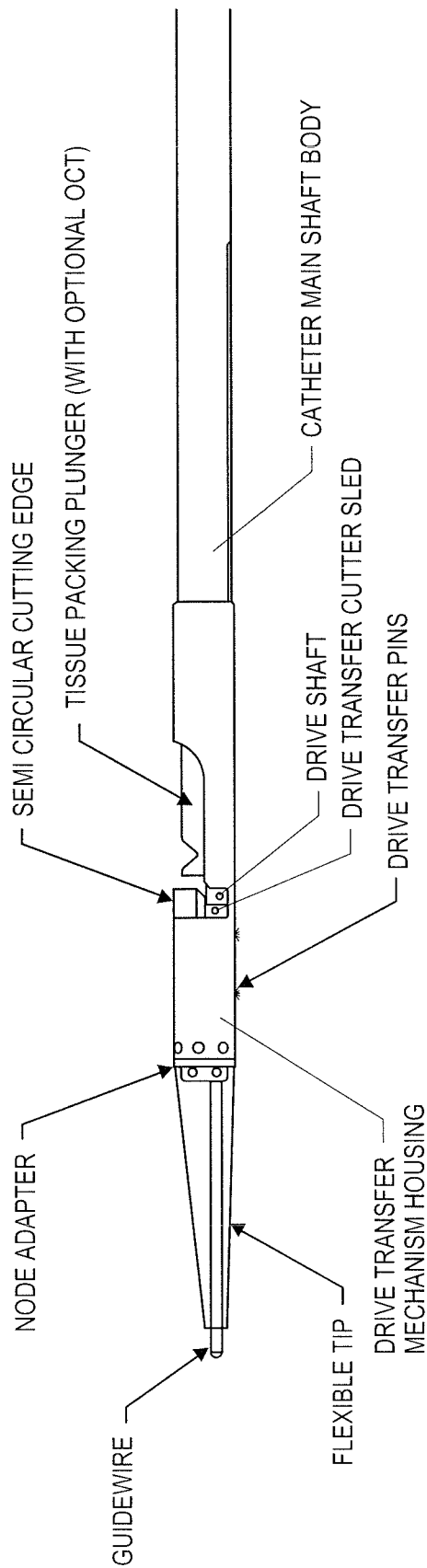
FIGS. 11-14B illustrate one variation of an atherectomy catheter having a cutting element.
Figure 12A:
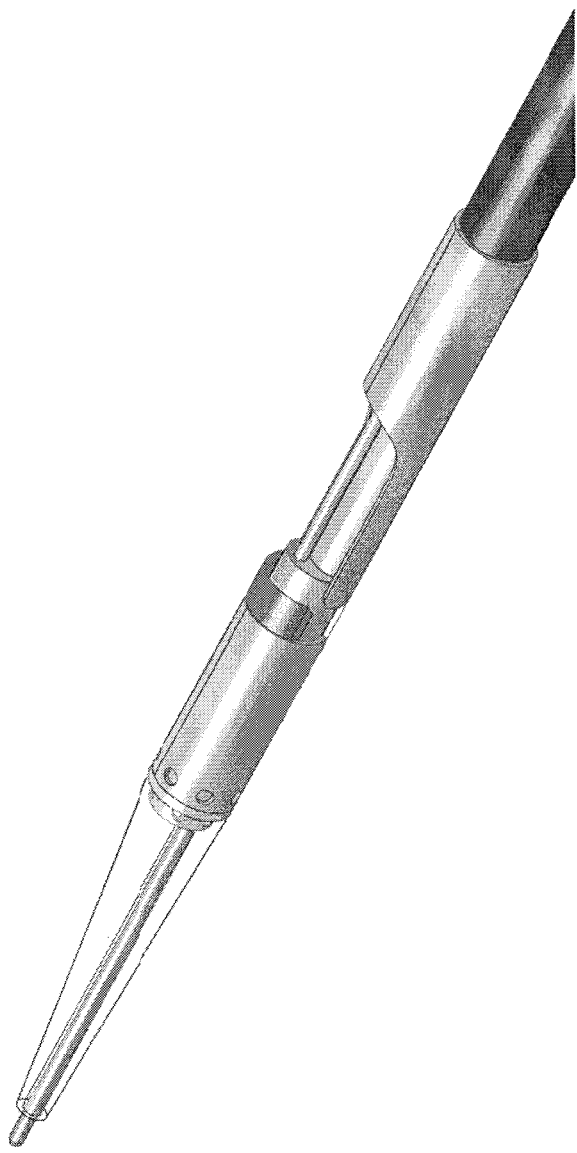
Figure 12B:
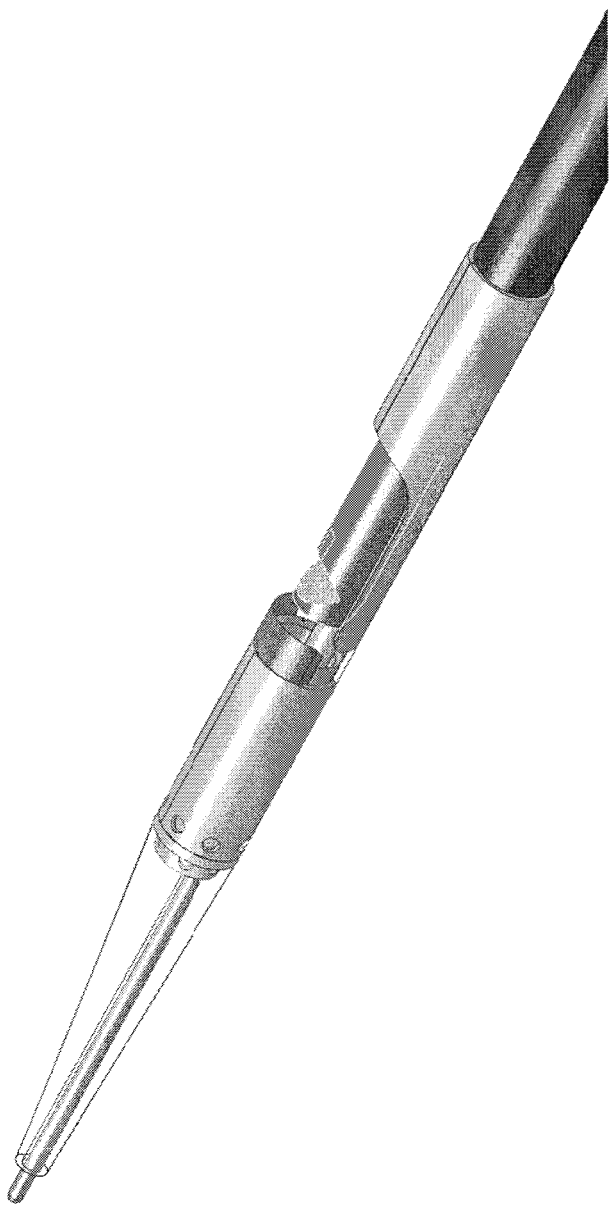
Figure 13:
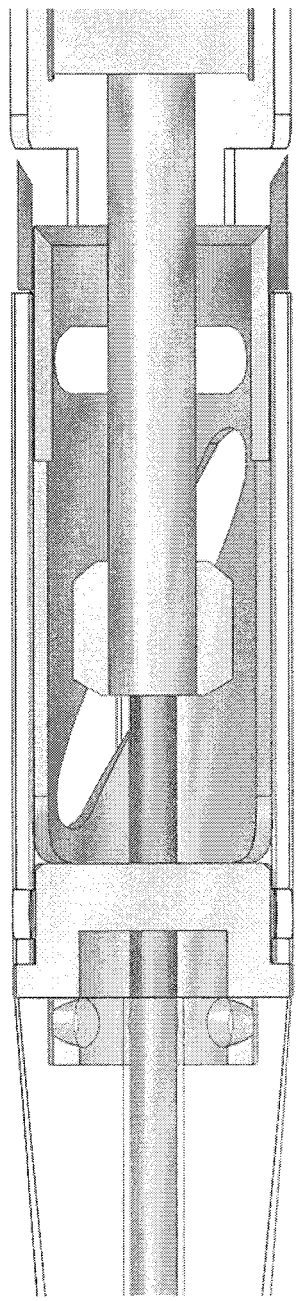
Figure 14A:
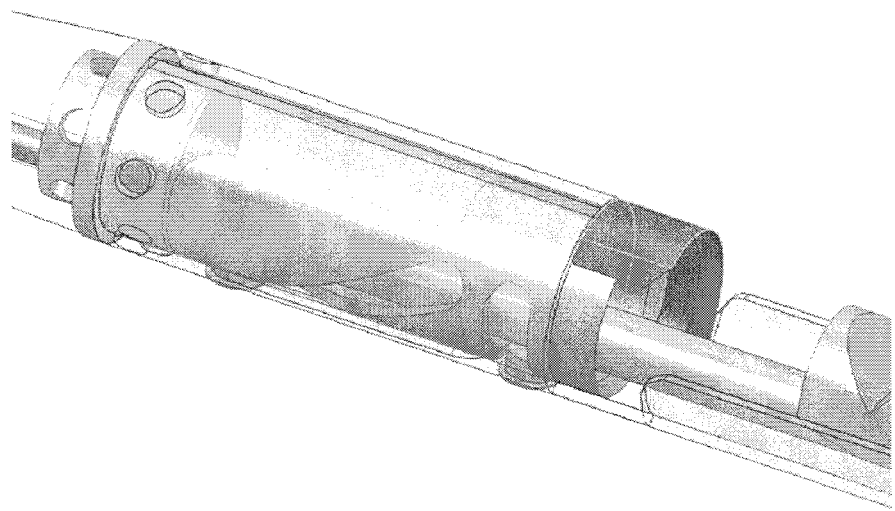
Figure 14B:
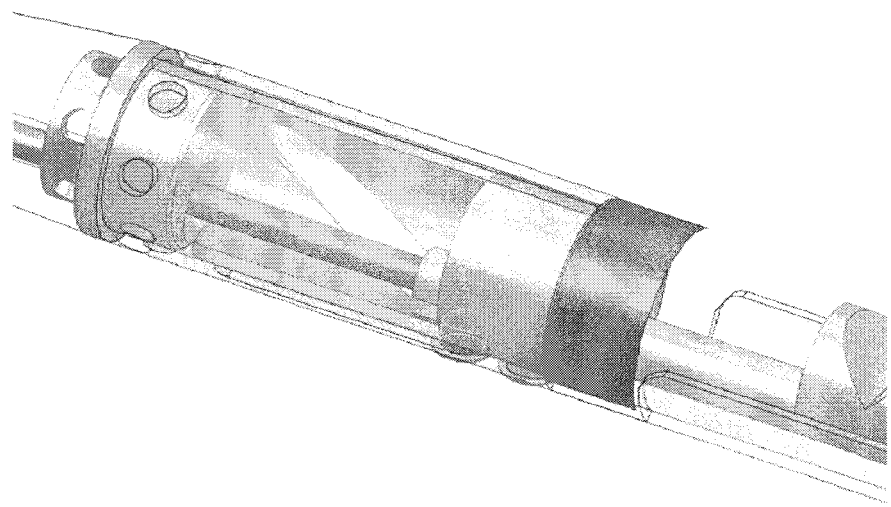
Figure 15B:
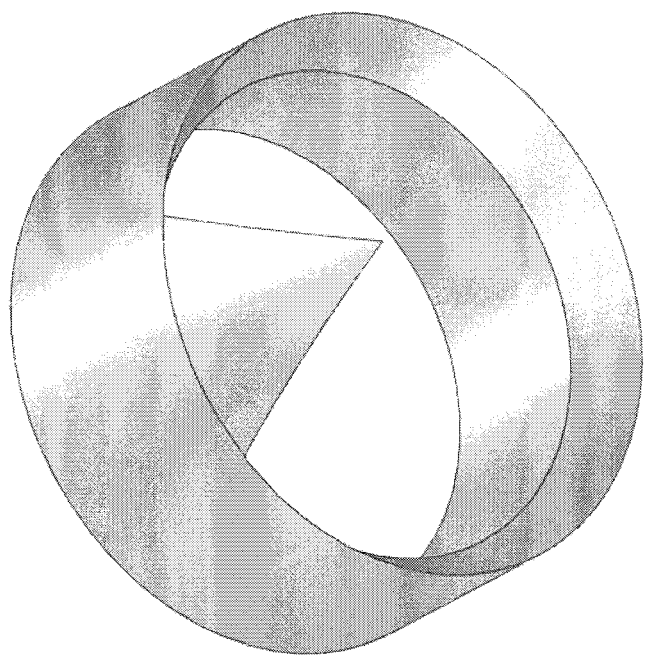
FIGS. 15A-15D illustrates exemplary cutters.
Figure 15A:
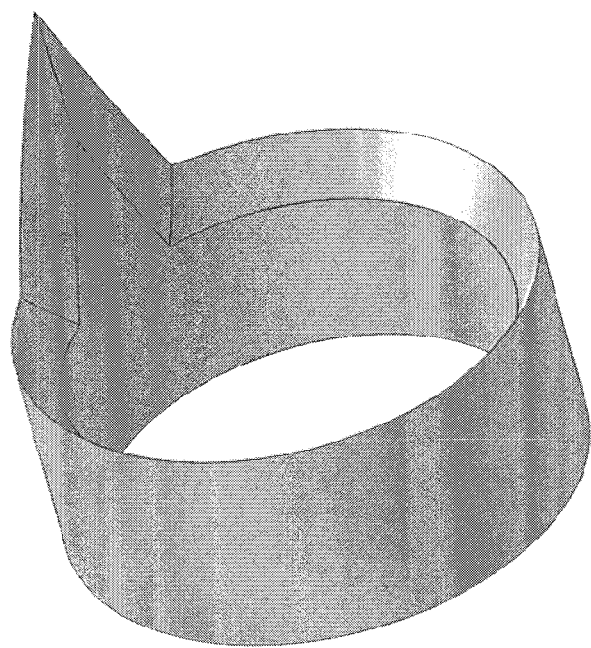
Figure 15D:
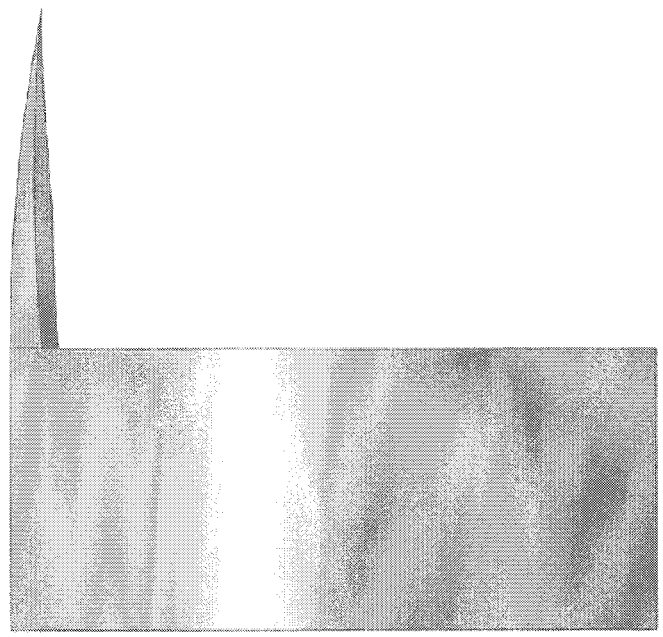
Figure 15C:
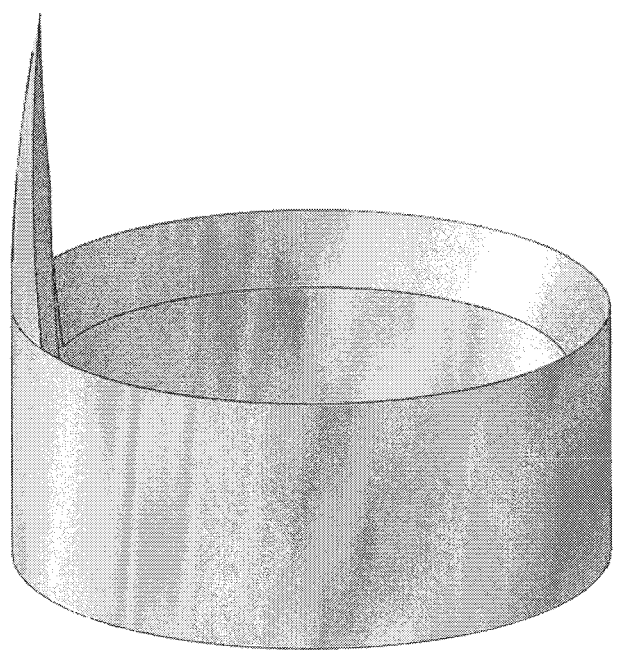

FIGS. 9A and 10 show one variation of a handle 901 for controlling the catheters described herein. FIG. 9A shows a system including an atherectomy catheter 900 connected to a handle 901; a second handle 904 is also shown attached. This second handle (shown in greater detail in FIG. 9B) may be used to help provide additional control of the atherectomy catheter. In some variations, the handle may be configured to be re-used with different atherectomy catheters. For example, the proximal end of the catheter may include connectors or adapters to mate with connectors in the handle to enable the various drive shafts to be controlled. In some variations, the handle is integrally connected to the proximal end of the catheter.

The handle shown in FIG. 9A is configured to separately control the cutting drive shaft and the imaging drive shaft. One or more controls 903 may be included to activate the cuter and/or the imaging. Alternatively, the handle may communicate with a controller (e.g., part of a visualization station) which may directly or remotely control the activation of the cutter and/or imaging sensor. Internal detail for the handle is shown in greater detail in FIG. 10, in which an outer cover from the handle of FIG. 9A has been removed. In FIG. 10, two separate drivers for the imaging and cutting drive shaft s are included within the handle. The handle also houses gearing that allows the imaging drive shaft to change direction (between clockwise and counterclockwise) in an automatic, continuous manner.

Also described herein, and shown in FIG. 9A and 9B, is a torque or control handle 904, which may be slid and locked into position on the elongate length of the catheter. This control handle may be locked onto the body of the catheter and may provide a grip to enhance comfort and control of the device, particularly when a substantial region of the length of the device remains outside of the body. In this example the control handle includes a control 905 (e.g., button, slider, etc.) for releasing and locking the handle onto various positions along the length of the catheter. The control handle may also include a separate control (e.g., button, etc.) for activating one or more functions otherwise controlled by the handle, such as starting/stopping rotating of the cutter and/or imaging sensor, etc. Thus, in some variations the control handle may be in communication (including wired or wirelessly) with the proximal handle including the rotational actuators.

The handle 1001 shown in FIG. 10 is one variation of a handle for a catheter having a separate drive shaft for the cutter (cutter drive shaft 1030) and the imaging sensor (imaging drive shaft). In this example, the inner drive shaft 1030 controls the cutter, which is rotated by a motor 1033. This inner drive shaft may also be pushed distally and pulled proximally to deflect the distal tip; thus the gears for rotating the drive shaft allow a portion of the controller 1040 to shift axially distally or proximally. A second actuator (motor 1043) may be used to drive this lateral motion. Thus rotation of the actuator is translated into axial/distal motion along the threaded screw 1044 on which the controller 1040 rides.

The side view of the handle shown in FIG. 10 includes a housing that has been made transparent (e.g., or for which an outer cover has been removed) to visualize the internal components of the handle 1001. In this example, the catheter extends from the distal end. The device may also include cords such as power and optic/imaging cords (not shown) coupled to the handle. The optical fiber (not visible) may be held within a channel 1057 and directed to the optical outputs for image processing. In the variations shown, the optical fiber may be secured in handle and held (e.g., affixed) relative to the handle, as previously mentioned. Thus, the proximal end does not typically rotate, but is fixed relative to the handle. The handle body may be covered by a housing which may be configured to conform to a hand or may be configured to lock into a holder (e.g., for connection to a positioning arm, a bed or gurney, etc.

The imaging drive sub-system within the handle 1001 may include a motor 1003 and drive gears 1015, 1016, 1017 that can drive the imaging drive shaft to rotate the imaging sensor on the rotatable chassis at the distal end of the device allowing OCT imaging into the walls of the vessel, as described above. In some variations the imaging drive sub-system is controlled or regulated by a toggling/directional control subsystem for switching the direction of rotation of the drive shaft between the clockwise and counterclockwise direction for a predetermined number of turns (e.g., between about 4 and about 100, e.g., between 8 and 20, about 10, etc.). In FIG. 10, one variation of a directional control is a mechanical directional control, which mechanically switches the direction of rotation between clockwise and counterclockwise when the predetermined number of rotations has been completed. In this example, the directional control includes a threaded track (or screw) 1011 which rotates to drive a nut 1013 in linear motion; rotation of the threaded track by the motor 1003 results in linear motion of the nut along the rotating (but longitudinally fixed) threaded track 1011. As the motor rotates in a first rotational direction (e.g., clockwise), the nut 1013 moves linearly in a first linear direction (e.g., forward) until it hits one arm of a U-shaped toggle switch 1016, driving the U-shaped toggle switch in the first linear direction and flipping a switch to change the direction of the motor 1003 to a second rotational direction (e.g., counterclockwise), and causing the nut to move linearly in a second linear direction (e.g., backward) until it hits the opposite side of the U-shape toggle switch 1016, triggering the switch to again change the direction of the motor back to the first rotational direction (e.g., clockwise). This process may be repeated continuously as the motor is rotated. The motor may be configured to rotate in either direction at a constant speed. The system may also include additional elements (e.g., signal conditioners, electrical control elements, etc.) to regulate the motor as it switches direction.

The number of threads and/or length of the threaded track (screw) 1011 may determine the number of rotations that are made by the system between changes in rotational direction. For example the number of rotations may be adjusted by changing the width of the U-shaped toggle 1014 (e.g., the spacing between the arms); lengthening the arms (or increasing the pitch of the screw) would increase the number of rotational turns between changes in direction (n). The toggle may therefore slide from side-to-side in order to switch the direction of the motor.

In some variations the motor is rotated in a constant direction and the switch between clockwise and counterclockwise are achieved by switching between gearing systems, engaging and disengaging an additional gear or gears that mechanically change the direction that the driveshaft is driven.

As mentioned above, the catheters described herein typically an elongate, flexible catheter length extending from the handle. The catheter typically includes an outer sheath surrounding an inner guidewire lumen (not shown). The various drive shafts extend along the length of the catheter to drive the cutter and/or imaging sensor at the distal end of the device in rotation. In some variations the imaging drive shaft is a tubular shaft and may surround the cutter drive shaft. The cutter drive shaft may be a solid shaft which extends through the length of the catheter.

In the exemplary device shown in FIG. 10, the imaging drive sub-system includes the motor 1003 and three gears 1017, 1016, 1015 that engage each other to drive the drive shaft in rotation. For example, the motor 1003 rotates a first gear 1017 which is engaged with a second gear 1016 (shown in this example as a 1:1 gearing, although any other gear ratio may be used, as appropriate). A third gear 1015 engages with the second gear 1016; the third gear may drive or regulate an encoder 1007 for encoding the rotational motion. This encoded information may in turn be used by the drive system, providing feedback to the drive system, or may be provided to the imaging system as discussed briefly below.

In operation, the user may turn on a switch (e.g., on the handle and/or the torque/control handle) to start operation of the overall system, including the rotation of the imaging system and/or cutter. In some variations the user may control the rate or speed of operation by controlling these rates of rotation, as mentioned above.

In any of the variations shown herein, the distal end of the catheter may include one or more fiduciary marks to aid in visualizing the catheter or to help determine the catheter orientation relative to the patient. For example, the catheter may include one or more electodense regions or markers that can be readily visualized using fluoroscopy to help orient the device within the body, including the rotational orientation. Any of the systems described herein may also include a control system for receiving and displaying the images received from the imaging sensor. The control system (e.g., see U.S. patent application Ser. No. 12/829,267 and U.S. patent application Ser. No. 12/790,703, the entireties of which are incorporated by reference herein) may connect to the handle and control or modify the rotation rate, rotation direction, cutting speed, contrast, display, data storage, data analysis, etc. of the atherectomy device.

Additional Examples

FIGS. 11-14B illustrate one variation of an atherectomy catheter having a cutting element (shown in this example as a semi-circular cutting element) that is actuated by longitudinal displacement of a drive mechanism. The drive mechanism may be a shaft, as mentioned above.

The variation illustrated in FIGS. 11-14B are configured as pull-to-cut atherectomy catheters, in which tissue may be collected in the distal nose region. Alternatively, in some variations the device may be configured as push-to-cut catheters. A tissue packing plunger may also be used to secure tissue within the collection region, and/or to cover the cutting element when not in use. It should be noted that either collection in the distal or proximal regions of the catheter may be used in pushing or pulling configurations, as the tissue may be channeled or deflected into the collection region of the device.

FIGS. 15A-15D illustrate variations of cutting elements that may be used. Because the cutter is driven in an oscillatory motion, the cutter edge can be configured for optimal cutting efficiency and is not limited to circular edges with continuously rotating cutters.

Figure 16:
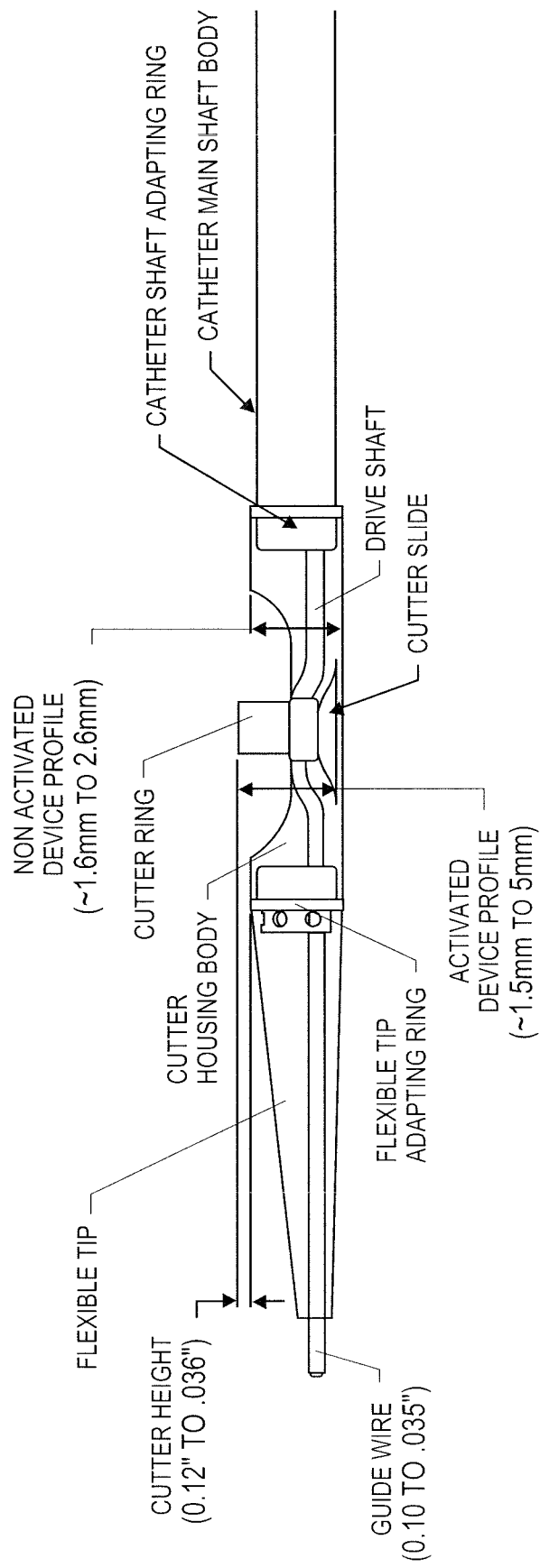
FIGS. 16-18 illustrate another variation of an atherectomy catheter having a cutting element.
Figure 17A:
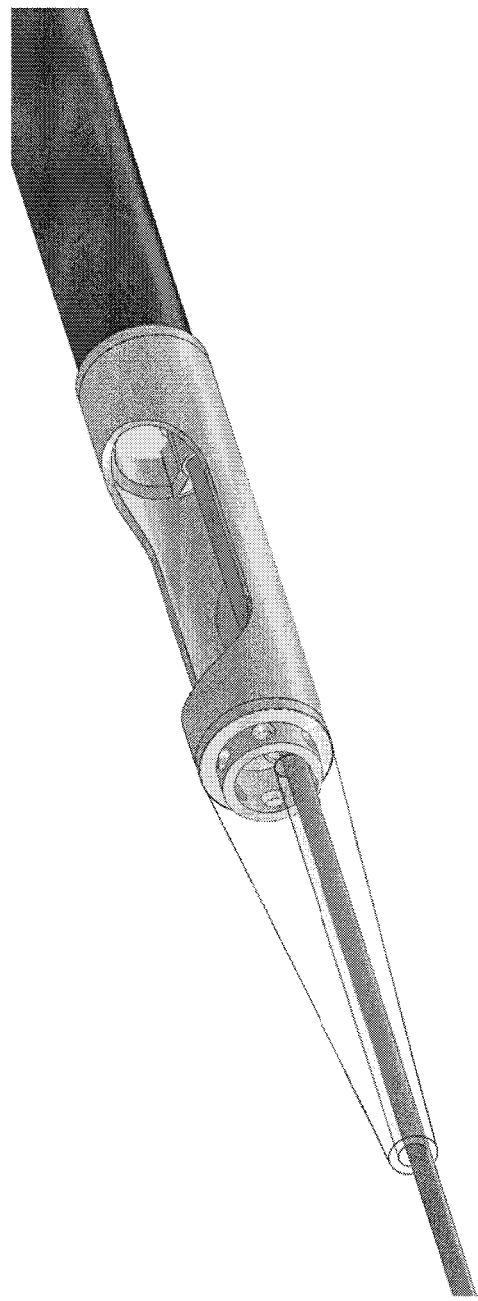
Figure 17B:
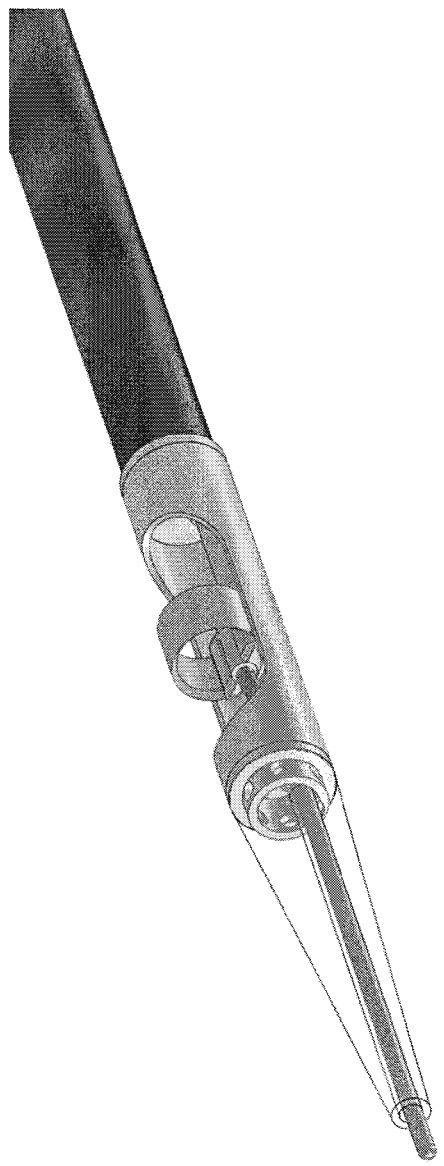
Figure 17C:
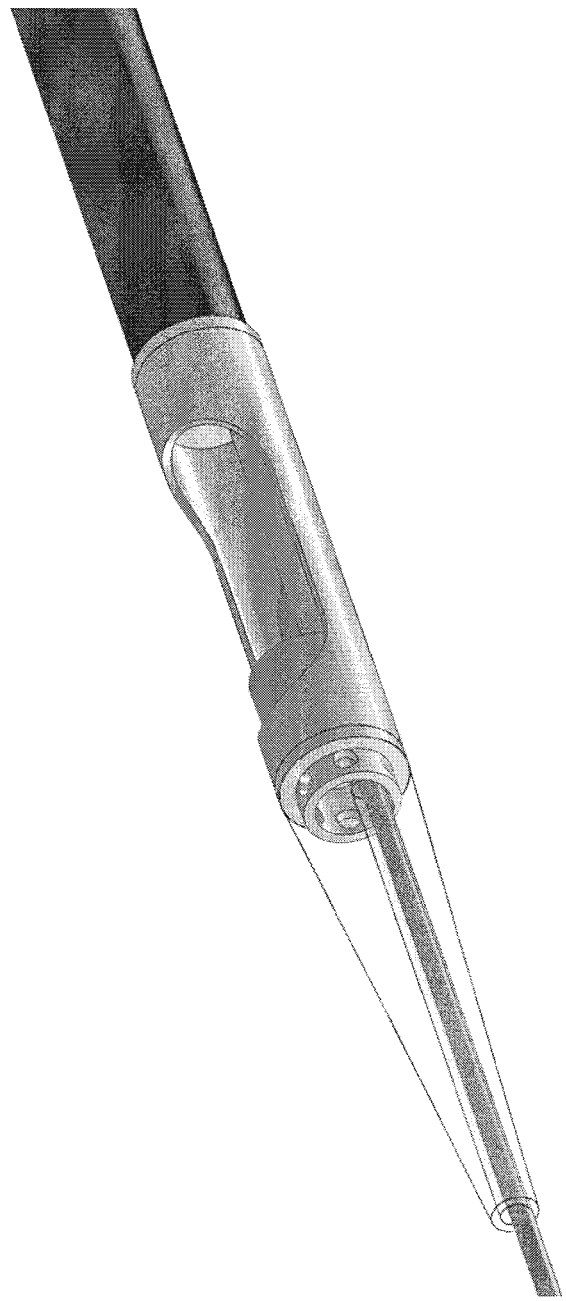
Figure 18:
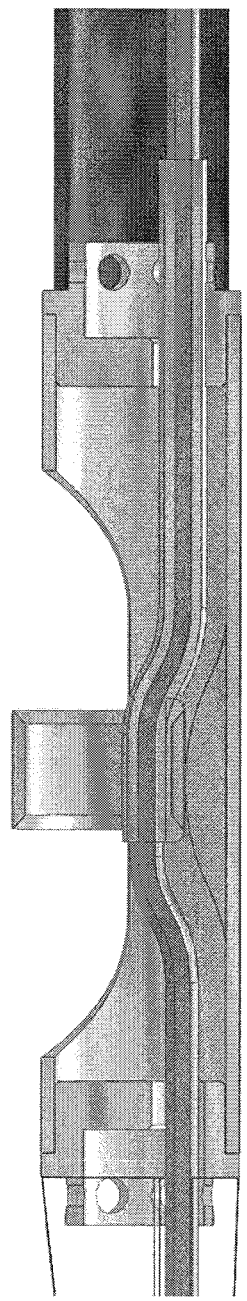

FIGS. 16-18 and illustrate another variation of an atherectomy device having a longitudinally actuated cutter. This variation is configured to cut as the blade slides both back and forth across the opening. In some variations tissue is not collected within the catheter, but is collected downstream in the vessel by a second or auxiliary device.

In any of these variations, the catheter device may also include on-board and real time image guidance capabilities. This may include an imaging element, or energy emitting assembly, positioned at the distal portion of the device such that local images of the vessel may guide device usage. One specific configuration of an OCT system that may be used for this distal imaging element is described, for example, in U.S. Pat. No. 9,788,790, previously incorporated by reference. The distal energy emitter(s) may be positioned in multiple locations in fixed positions or embodied in a mating assembly that may translate in an eccentric lumen or in the hollow lumen of the driveshaft. The emitter may send and receive relevant light or sound signals at 90 degrees from the catheter axis or at angles up to approximately 50 degrees to visualize distal or proximal wall features from a fixed position.

Furthermore, the data collected at the distal end of the catheter, after transmitted and appropriately processed, may drive an automated means of tip actuation and cutter position. Increased amounts of disease detected by the software may automatically increase tip axially offset consequently increasing cut depth and apposition force. Cutter speeds, gear ratios and torque inputs may be adjusted according to input from the imaging system.

As mentioned briefly above, in some variations any of the atherectomy catheters may be configured for use, and used, without a rotating imaging system (e.g., OCT imaging system). Alternatively, in some variations, such as those shown in FIGS. 21A and 21B, the imaging sensor is controlled on-axis.

Figure 21A:
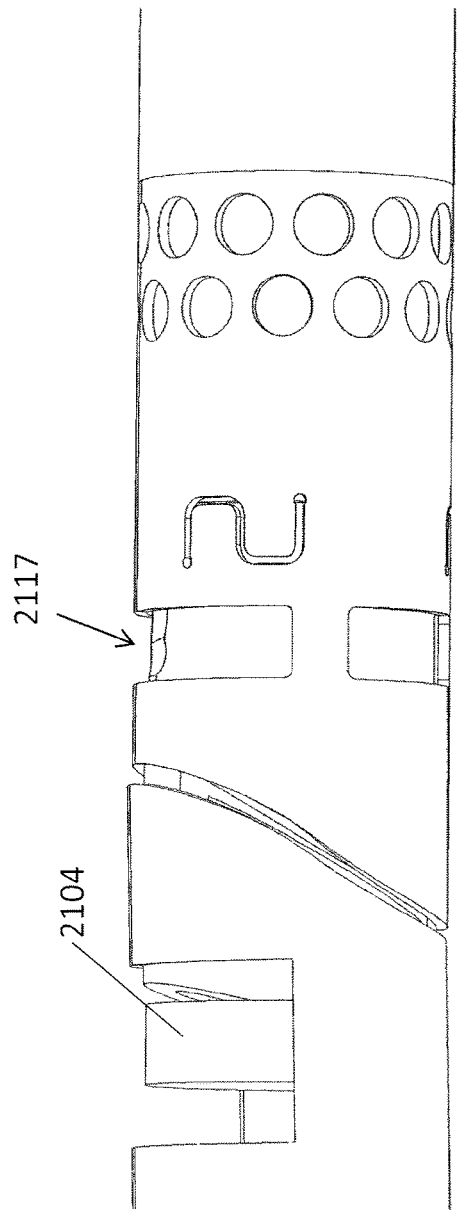
FIG. 21A shows another variation of a distal end portion of an atherectomy catheter including an imaging sensor.
Figure 21B:
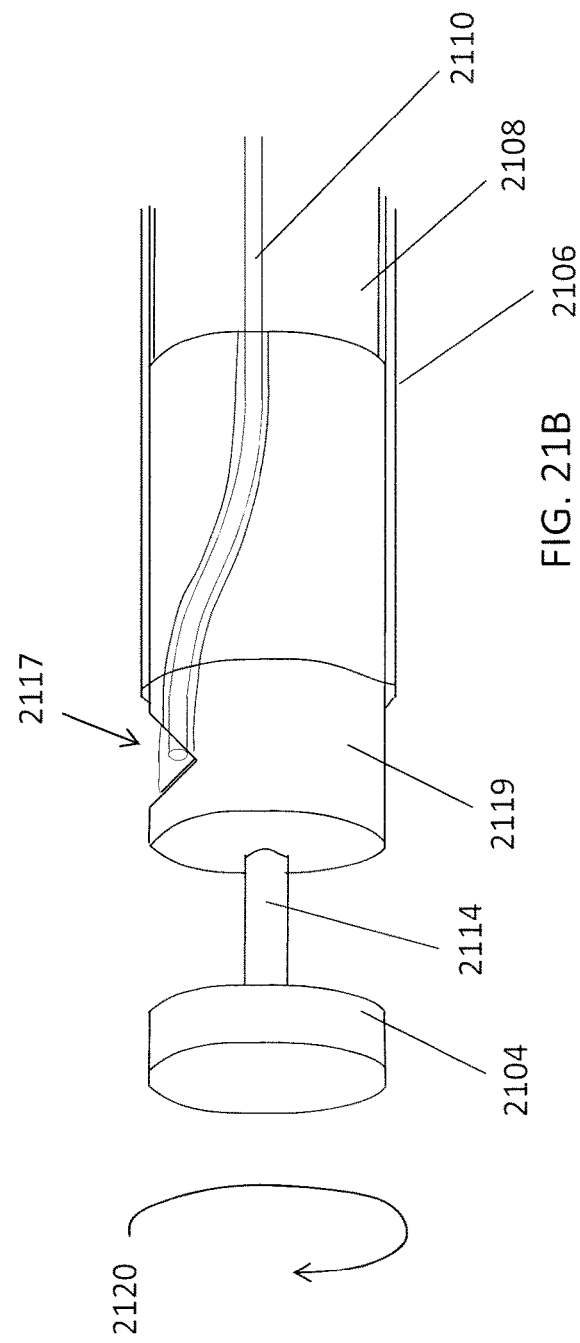
FIG. 21B shows another configuration of an imaging sensor and cutter in which the cutter and imaging sensor rotate together and fiber optic of the imaging sensor is centrally located; the fiber optic management is similar to the variation shown in FIG. 20.

FIGS. 21A-B illustrate an additional variation of the atherectomy catheter similar to those described above in FIGS. 1-7B, in which the imaging sensor is rotated with the cutter. In this variation, the second drive shaft (imaging drive shaft) is not included, and the imaging sensor may be affixed to a rotating chassis that is also rotated by the same drive shaft driving the cutter. In some variations the imaging sensor is rotated at the same rate as the cutter; in other variation (not illustrated in FIGS. 21A-B) there is a gearing between the drive shaft for the cutter and the rotatable imaging chassis so that the rate of rotation of the imaging sensor is geared to step down from the rate of the cutter rotation.

For example, FIG. 21A shows a portion of an atherectomy device having an imaging sensor that is rotated by the cutter drive shaft just proximal to the distal end of the catheter. This region includes the cutter 2104 and imaging sensor 2117. In this variation, the imaging sensor includes a mirror so that the fiber optic is configured to "look" at the walls of the vessel in which the atherectomy device is positioned. The device typically operates as described above; the distal tip region (not shown) may be displaced to expose the cutter 2104, and cut may be rotated to cut the tissue. Tissue that is cut may be stored in the distal tip region.

FIG. 21B shows one variation of the cutter and imaging catheter in which the two are coupled together so that rotation of the cutter also rotates the imaging catheter. A cutter drive shaft 2108 drives rotation of both the cutter 2014, via a cutter shaft 2114, spacing it from the imaging sensor 2117. The imaging sensor 2117 is affixed a rotatable chassis 2119. In this variation, the optical fiber 2110 is secured within a channel within the chassis to position the optical fiber in the central lumen region of the catheter (e.g., within the drive shaft 2108). During rotation, the chassis 2119 rotates with the cutter, rotating the distal end of the optical fiber, and allowing imaging during rotation; the optical fiber within the center of the catheter is allowed to freely rotate, although it may be constrained within a channel in the lumen of the drive shaft by the diameter of this channel. As it rotates in a first direction (e.g., clockwise), the optical fiber may be twisted upon itself. Although this would seem counterintuitive, the centered fiber may robustly handle hundreds of rotations without damage. After a predetermined number of rotations (e.g., 200, 300, 400, 500, 600, 700, 800, 900, 1000, 1500, etc.), the drive shaft may switch the direction of rotation and my continuously toggle back and forth between these directions as previously described. Thus, the cutter may also change direction.

Imaging Catheters

Also described herein are imaging catheters that do not necessarily including cutting elements as described above. For example, in some variations an imaging catheter may include an elongate body having a distal end that includes an imaging sensor (e.g., an OCT imaging sensor) including fiber optic element that is attached to the distal and extends (loose or unattached) within the elongate body of the catheter until it is secured in a proximal end of the device. In some variations just the distal tip of the imaging catheter is configured to rotate with the imaging sensor; in some variations the entire imaging catheter outer body may rotate, including the imaging sensor. In general, the imaging catheters described herein allow the optical fiber to be wound, wrapped or coiled as the imaging sensor is rotated. Thus, the distal and proximal ends may be fixed; for example, the distal end may be fixed to a rotatable chassis that may rotate relative to the handle, while the proximal end of the fiber is fixed relative to the rotating distal tip, and the intermediate portion is allowed to wrap and/or twist while in rotation. As a result, the imaging sensors are configured to rotate for a finite number of rotations in a first (e.g., clockwise) direction, followed by rotation in the opposite (e.g., counterclockwise) direction, and this clockwise/counterclockwise rotation may be repeated.

As mentioned above, the devices described herein may be rotated through a surprising number of rotations without damaging the fiber optic properties; in some variations in which the optical fiber is allowed to twist around itself (rather than wrapping around a shaft, wire, or the like) the fiber may be rotated for hundreds or rotations (e.g., 100, 200, 300, 400, 500, 600, etc.). The optical fiber may be held within a channel or passage having a fixed diameter to prevent the twisting fiber from kinking. In some variations, the optical fiber may be coated or clad with a material to provide support or strength; for example, the optical fiber may be coated with an elastomeric material, or a stiffer material.

Figure 20:
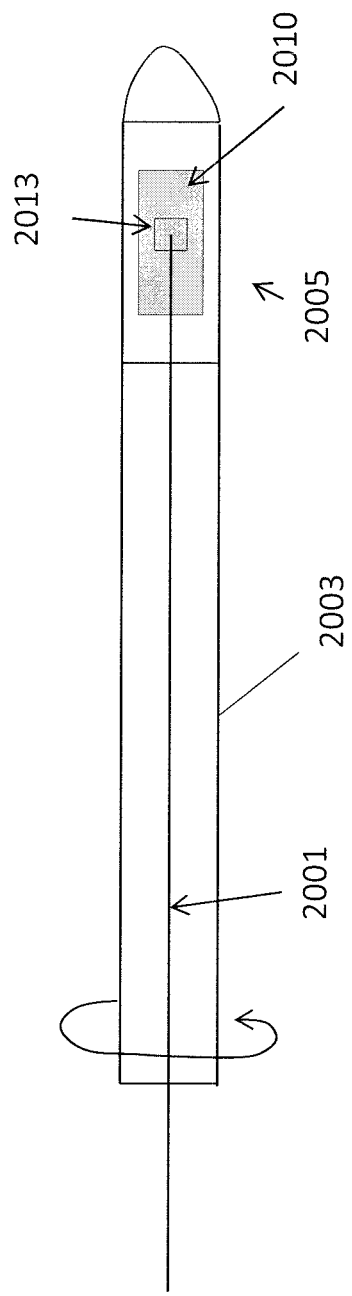
FIG. 20 illustrates another variation of an imaging guidewire.

For example, FIGS. 19A-20 illustrate two variations of imaging catheters in which the optical fiber is allowed to coil or wind up as the device is operated, e.g., as the imaging sensor is rotated at the distal end of the catheter. In both variations the imaging sensor is configured as an OCT imaging sensor formed of an optical fiber that affixed (e.g., embedded in an epoxy) so as to image within or through the lumen of a vessel. The imaging sensor in these examples may include a mirror for directing the imaging light out of the catheter and into the walls of the lumen; thus the imaging sensor may be configured to image to the side (e.g., approximately 90° off the long axis of the catheter), forward, backward, or some variation in between. The distal end of the optical fiber forming the imaging sensor is typically secured to a rotating element, at or near the tip. The proximal end of the optical fiber may also be fixed, and does not rotate relative to the distal end of the device. The portion of the fiber extending between the proximal and distal ends is typically free to rotate and, in some variations, wind or unwind within a lumen and/or around a wire or shaft within the catheter.

The imaging catheter 1900 shown in FIG. 19A includes an outer sheath (torque shaft 1907) that remains stationary while distal end region (imaging window 1903) rotates; the distal end of the optical fiber 1903 is affixed to the rotating imaging window 1903, which may be configured as a rotatable chassis. This chassis may be rotated by turning the central wire that is configured as a drive shaft 1905. As the drive shaft is rotated and rotates the imaging window 1915, the imaging sensor sweeps a beam of light 1912 around the perimeter. The drive shaft (wire) may be any appropriate material, including braided, solid, or hollow materials; in some variations the drive shaft is Nitinol. The distal tip region 1913 may be configured to prevent damage to tissue. For example, the distal tip region may be soft and rounded (atraumatic). Thus, in this variation the drive shaft 1095 rotates (spinning the distal end region 1915) while the torque shaft 1907 remains stationary, allowing the fiber optic to wrap around the torque shaft. In one exemplary variation the outer diameter of the shaft is approximately 0.0335 inches, the length is approximately 57 inches, and the diameter of the drive shaft (wire) is approximately 0.011 inches.

In operation, this imaging catheter may be used as an OCT imaging catheter, and allowed to rotate the drive shaft (and thus the imaging sensor) alternately clockwise, then counterclockwise some number of rotations. The number of rotations clockwise/counterclockwise may be predetermined, or it may be based on some estimate of tension in the optical fiber.

FIG. 19B shows a variation of an imaging catheter similar to the variation shown in FIG. 19A, however the rotating imaging window region 1915 includes a one or more openings 1909 to allow "flushing" of the imaging sensor. Flushing may help clear the imaging sensor from blood and other debris that may otherwise prevent clear imaging. In some variations the imaging sensor is flushed by applying pressurized fluid (e.g., saline, etc.) through the catheter body as described above.

Another variation of an imaging catheter is shown in FIG. 20. In this example, the imaging catheter includes an outer torque shaft 2003 that rotates, while the fiber optic 2001 twists on itself within the lumen of the catheter. In this variation the distal end of the optical fiber is secured to the imaging window region 2005 of the catheter. This distal tip region 2005 rotates as the torque shaft 2003 rotates, rotating the distal end region of the optical fiber. In any of the variations described herein, the distal end of the optical fiber may be secured by epoxy or other appropriate means (e.g., to a rotatable chassis, catheter tip, etc.); for example, the end of the fiber optic may be encapsulated in an epoxy at the distal end of the device by a material 2010 having an appropriate index of refraction (e.g., see U.S. patent application Ser. No. 12/790,703, titled "OPTICAL COHERENCE TOMOGRAPHY FOR BIOLOGICAL IMAGING" and filed on May 28, 2010). Thus, the end of the fiber optic may be formed as part of a beam-tuning region 2013 for emitting/receiving the beam into/from the tissue and forming the OCT image from the tip 1005 region of the catheter. In one exemplary variation, the catheter (torque shaft) has an outer diameter of approximately 0.0375 inches (0.0340 inches in another example) and a length of approximately 54 inches (55 inches in another example), however, any appropriate dimensions may be used.

In some embodiments, an atherectomy catheter having a displaceable distal tip may include a lateral and/or external actuation element configured as a tendon, wire, rod, fiber, member, or the like that is generally attached to the distal tip of the catheter (though it may be hinged) and movable relative to the proximal portion of the catheter so that it can be moved (pushed or pulled) to actuate or displace the distal tip and expose the cutter of the atherectomy device. In some variations, this may be referred to as a pull-wire activation mechanism. The proximal end of the pull-wire may be attached to a pull shaft that extends all or partially down the length of the catheter from near the distal cutter toward the proximal handle. In some embodiments, the pull-wire extends proximally down the length of the catheter.

For example, in one embodiment, an atherectomy device includes a pull-wire activation mechanism. As should be apparent, a "pull-wire" lateral actuation element may be a tendon, wire, rod, member, or the like, and is not limited to wires. Although the actuation element may be referred to herein as a pull-wire, it should be understood that other structures may be used.

One example of an atherectomy device 81400 with an internal pull shaft 81402 and pull-wire 81524 is illustrated in FIGS. 35A-36B. The pull-wire is laterally displaced on the body of the catheter and spans the hinged region between the distal tip (nosecone region) and the rest of the catheter body. The atherectomy catheter 81400 can include a catheter body 81404, a cutter 81406 at a distal end of the catheter body 81404, and an end region or nosecone 81408 at a distal end of the catheter body 81404. The nosecone 81408 can be hollow for storing cut tissue that may be later removed and examined and can further include a cutting window 81430 through which a cutting edge 81412 of the cutter 81406 can be exposed. The nosecone 81408 can be attached to the catheter body 81404 through a deflection mechanism, such as a hinge mechanism 81410, to allow the nosecone 81408 to deflect away from the longitudinal axis of the catheter body. In use, this deflection can expose the cutting edge 81412 through the cutting window 81430 and/or radially push the cutter 81406 into a wall of the vessel in which the atherectomy catheter 81400 is inserted. The atherectomy catheter 81400 can further include a stop 81892 (see FIG. 39) to prevent the nosecone from deflecting too far when in the open position.

As shown in FIG. 36B, the atherectomy catheter 81400 can include an imaging element, such as an optical fiber 81514 for OCT, e.g., common path OCT, attached proximal to the cutting edge 81412 of the cutter 81406. The optical fiber 81514 can run through the center of the elongate body, such as through a drive shaft 81516 connected to the cutter 81406, to provide the signal for OCT. The optical fiber 81514 can be attached at the distal end of the catheter, such as in an opening 81518 in the cutter 81406. The optical fiber 81514 can otherwise be free to float within the catheter body 81404. In another embodiment, the optical fiber is attached to a drive shaft within the catheter body. In another embodiment, the optical fiber is off-axis from the drive shaft. A reflective element, such as a mirror 81520, can further be located within the opening 81518 in the cutter 81406 to radially direct light from the optical fiber 81514 into the tissue. The distal end of the optical fiber 81514 can be located less than 3 mm from the cutting edge 81412, such as just adjacent to the cutting edge 81412. By having the imaging element close to the cutting edge, the resulting image closely aligns with the portion of the vessel being cut, providing an advantageous view for the physician during an atherectomy procedure.

The catheter body 81404 of the atherectomy catheter 81400 can include an outer shaft 81522 that can be configured to be turned, such as turned manually or through a driver, such as the magnetic driver described above, to position the distal cutter 81406 and/or the imaging element toward the desired location. A pull shaft 81402 can extend within the outer shaft, and may be concentric with the outer shaft 81522 and inner drive shaft 81516. Using a pull shaft 81402 that is concentric with the shaft system can advantageously circumvent any whip or irregular catheter body rotation that may otherwise be introduced by an off-center component running through the length of the device, i.e. can open and close the nosecone without impacting the directionality of the catheter. A pull-wire can 81524 be attached at one end to the distal end of the pull shaft 81402 and at the other end to a central portion of the nosecone 81408. The pull-wire can run along the outer surface of the catheter. The pull shaft 81402 can be configured to be translated back and forth (proximally and/or distally), such as manually or with a driver, e.g. the magnetic driver above. Such translation of the pull shaft 81402 can pull or push on the pull-wire 81524, thereby causing the nosecone 81408 to deflect away from the central axis in one mode and return to the neutral (undeflected) position in another mode. The nosecone 81408 is thus actuated in and out of the plane of the rest of the catheter to expose or protect the rotating cutter 81406. In one example, this deflection may occur via rotation about the hinge mechanism 81410. For example, the hinge mechanism 81410 can be a pivoting and/or sliding joint that allows deflection of the nosecone 81408 as force is applied by the pull shaft 81402. Deflecting the nosecone 8408 exposes the rotating cutter 81406. This is illustrated in FIG. 35C (showing the catheter in the closed configuration) and FIG. 35D (showing the catheter with the distal tip deflected).

In some variations, the pull shaft can be connected to the nosecone 81408 at a region distal to a joint between the nosecone 81408 and the catheter body 81404, and may act as a hinge (e.g. a living hinge) to pull and bend (or push and extend) the distal tip region.

As noted above, the catheter body 81404 of the atherectomy catheter 81400 can include a drive shaft 81516 extending concentric with the pull shaft 81402, such as extending within the pull shaft 81402. The drive shaft 81516 can be attached to the cutter 81406 (which can be positioned between the catheter body 81404 and the nosecone 81408) and can be configured to rotate the cutter 81406. Rotation of the cutter 81406 can provide cutting due to the rotational motion of the cutting edge 81412 and can provide the rotation necessary to image the inner diameter wall components of a vessel with the imaging element. The drive shaft 81516 can be rotated at up to 2,000 rpm, such as approximately 1,000 rpm in a single direction, though rotation in both directions and at different speeds is possible.

Having a separate outer shaft, pull shaft, and drive shaft can advantageously separate the rotational motion of the cutting element from the translational motion required to activate/deactivate the deflection mechanism. This separation can avoid placing tension or compression on the drive shaft during the axial translation that is used to deflect/undeflect the nosecone, which can cause distortion in the resulting image. This separation can further simplify the distal mechanism design relative to having all elements (pull and drive) combined in one drive system, enabling the device to be scaled down to reduced sizes for small vessels, such as coronary arteries.

In some embodiments, a monorail guidewire lumen 81844 is located on the distal portion and/or nosecone 81408 of the device. Positioning the guidewire in a monorail lumen 81844 provides more room in the catheter body 81404 for the optical fiber and pull shaft elements. Further, positioning the guidewire lumen 81844 opposite the cutting window 81430 provides an additional element that is visible via OCT for directing the cutter toward a lesion of interest, as discussed further below. When the monorail guidewire lumen is used, the guidewire can extend along the outside of the catheter body, such as be free floating until it reaches the guidewire lumen (as shown and discussed with respect to FIGS. 41H-K below).

Referring to FIGS. 37A and 37B, a handle 81600 can be used to control the activation of the pull shaft. The pull shaft can be attached to the pull shaft "plug" 81626 in the handle 81600. An extension from this plug 81626 can be accessed by the user and translated proximally/distally along the length of the handle either manually or through a driver, such as the magnetic driver described above. This proximal and distal movement of the pull shaft can result in the nosecone deflecting/undeflecting. The translation plug 81626 in the handle 81626 can be separate from a mechanism that moves the cutting/imaging element to move the cutter to pack tissue into the nosecone. Thus, the pull shaft plug 81626 enables manipulation of the nosecone deflection angle independently from the drive system that controls cutting and imaging. A rotation mechanism, such as a knob 81628 can be used to rotate the outer shaft (again either manually or with a driver such as the magnetic driver described above) to direct the cutter to the proper location.

Figure 38B:
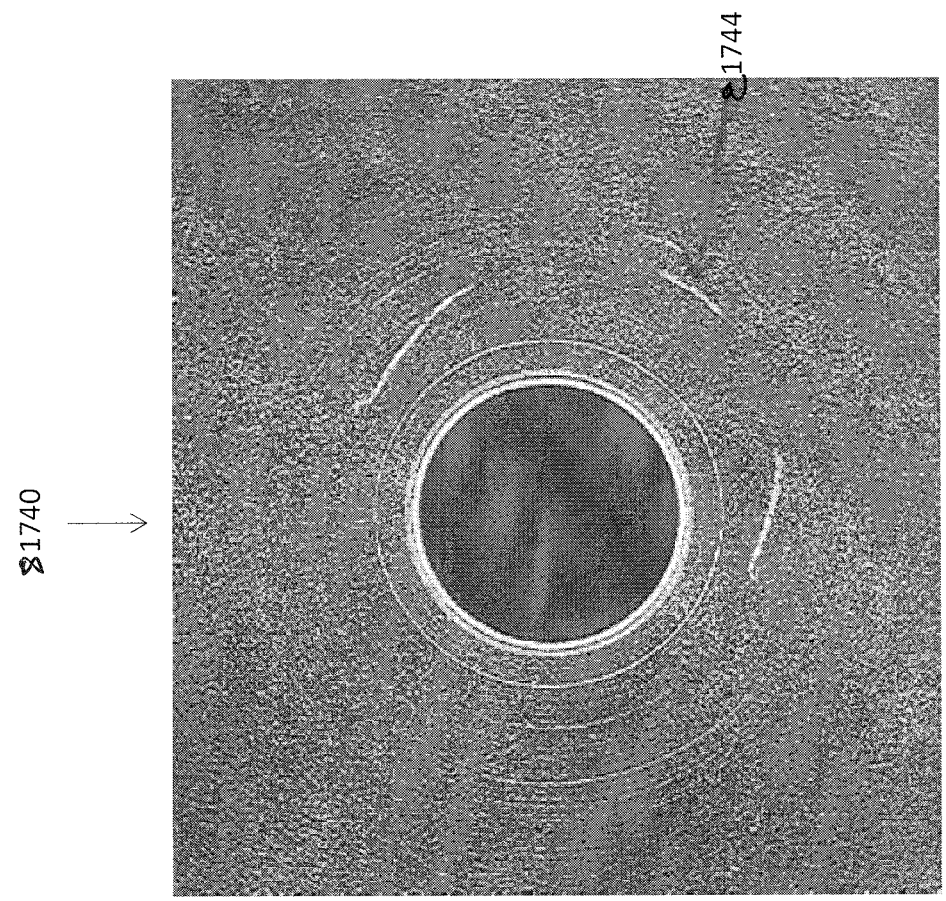
FIG. 38B shows an OCT image produced from the atherectomy catheter of FIGS. 35A-36B with the nosecone opened (cutter activated) as indicated by the bright reflection from the off-centered housing.
Figure 38A:
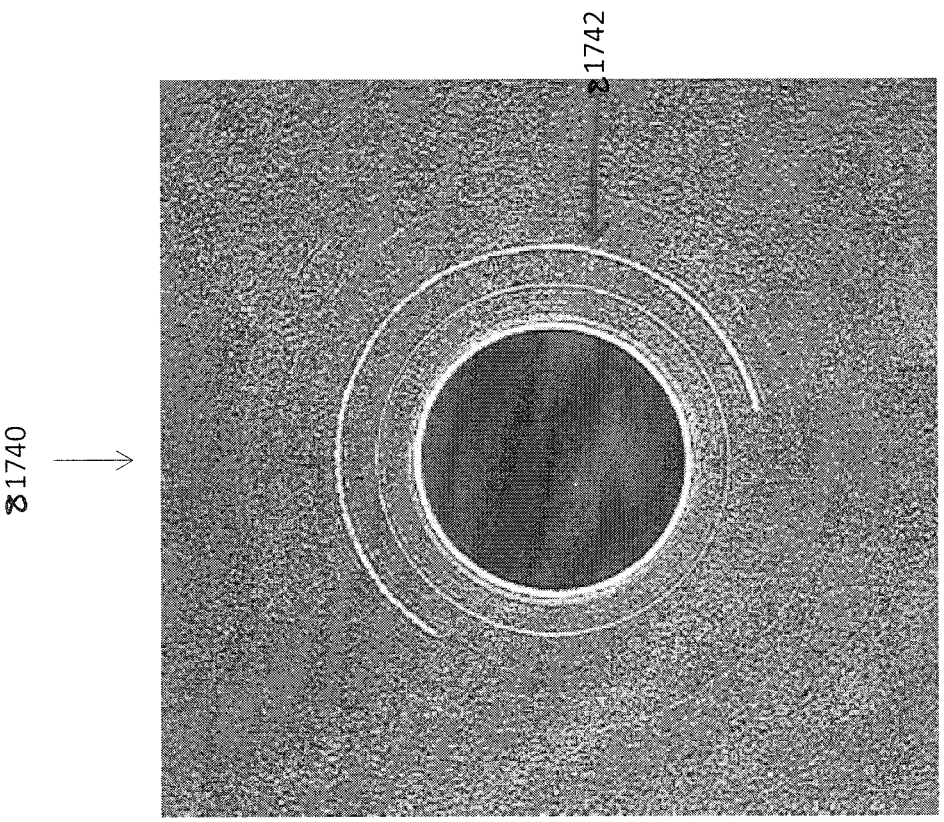
FIG. 38A shows an OCT image produced from the atherectomy catheter of FIGS. 35A-36B with the nosecone closed (cutter packed) as indicated by the bright reflection from the housing.

In this example, the imaging sensor of the OCT imaging sub-system is coupled just proximal to the rotating cutter. Thus, the catheter may image with the distal tip either in-line with the rest of the catheter or deflected (exposing the cutter), or in some variations, the imaging system may provide a somewhat restricted view when the distal tip is deflected and cutting is engaged. This may occur when the distal tip and/or pull shaft may occlude part of the OCT imaging sensor as it rotates around the distal tip, and may be beneficial as providing direct feedback to the operator that the cutter is engaged. For example, referring to FIGS. 38A and 38B, rotation of the imaging element on of the atherectomy catheter 81400 can result in an image of the interior of the vessel in which the atherectomy catheter is inserted. Referring to FIG. 38A, when the nosecone is closed, a mark 81742 may display on the OCT image 81740. The mark 81742 will correspond to the portion of the housing that extends around the nosecone, i.e. to the portion that is not occupied by the cutting window. Because this mark 81742 will always be opposite to the location of the cutter, the mark 81742 can be used to steer the atherectomy cutter to the desired location via rotation of the outer shaft toward the desired location. Referring to FIG. 38B, when the nosecone is open, the OCT image 81750 a similar but shorter mark 81744 may display that corresponds to the housing. This mark 81744 can again be used to steer the atherectomy cutter to the desired location. Further, the length of this mark 81744 may be used to indicate how far the nosecone is deflected away from the main catheter axis, providing a real-time tool to gauge cut depth.

Figure 39:
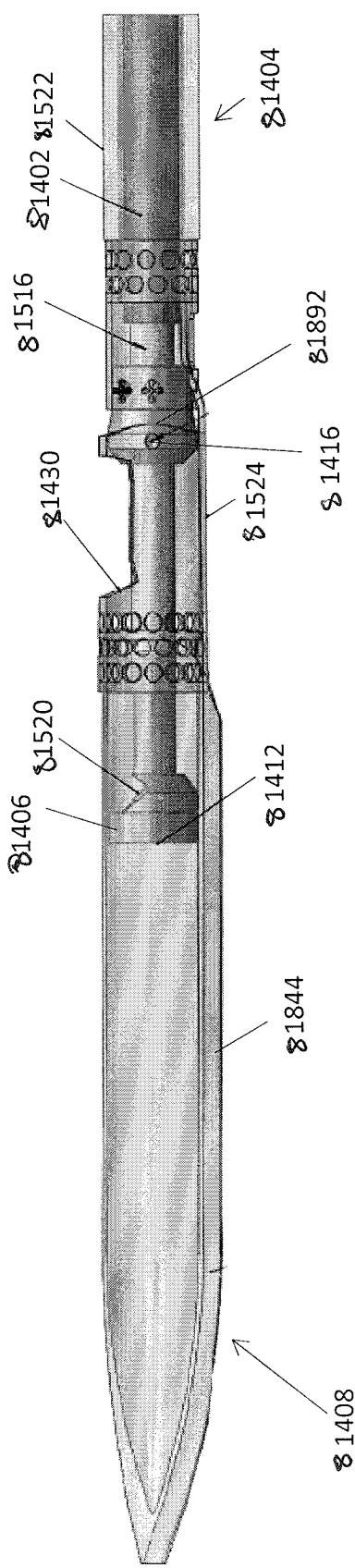
FIG. 39 shows an atherectomy catheter having a pull-wire activation mechanism and a driveshaft and cutter extendable into the nosecone.

In some embodiments, referring to FIG. 39, one or more of the shafts of the atherectomy catheter 81400 can be translated axially to pack dissected tissue into the nosecone 81408. Thus, as shown in FIG. 39, the drive shaft 81516 can be configured to be translated axially (manually or through a driver such as the magnetic driver described above), thereby translating the cutter 81406 axially, such that the distal surface of the cutter can be used to advance and pack the cut tissue into the nosecone 81408. If the drive shaft 81516, and thus the cutter 81406 and imaging element, has been pushed into the nosecone 81408, then the monorail guidewire lumen 81844 can be used as a marker to assess the location of the cutter.

Figure 40:
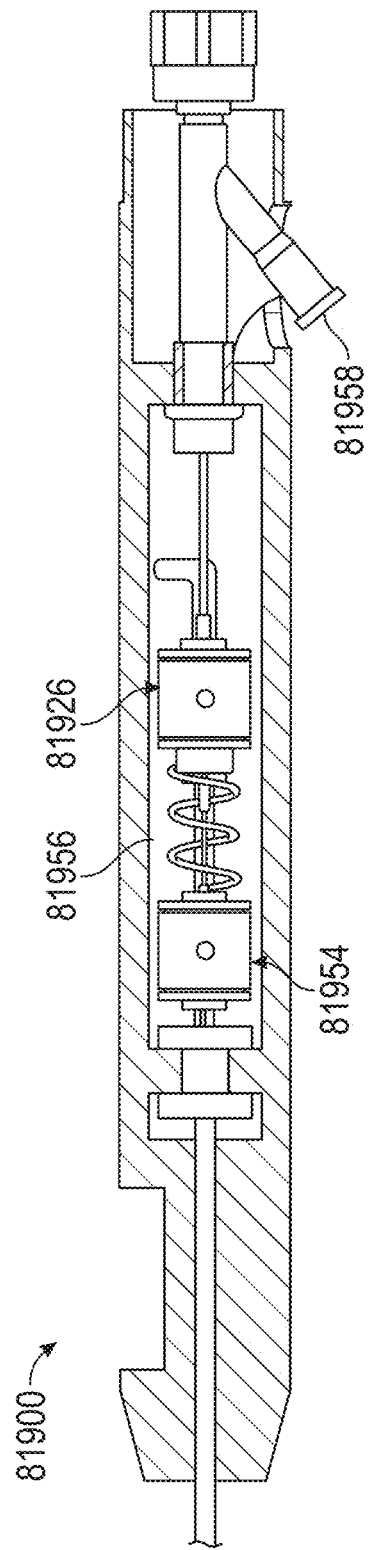
FIG. 40 shows a handle used to control the pull shaft of the catheter of FIG. 39 to open and close the nosecone as well as a slider to move the driveshaft forward to pack tissue into the nosecone.
Figure 41C:
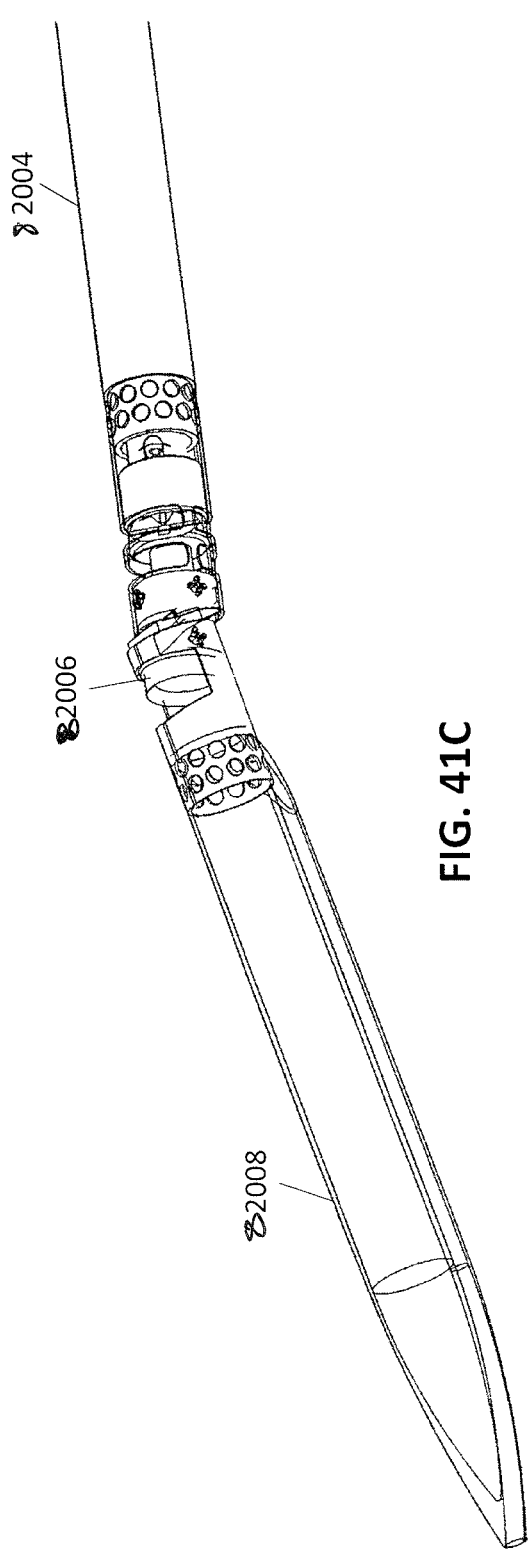
Figure 41D:
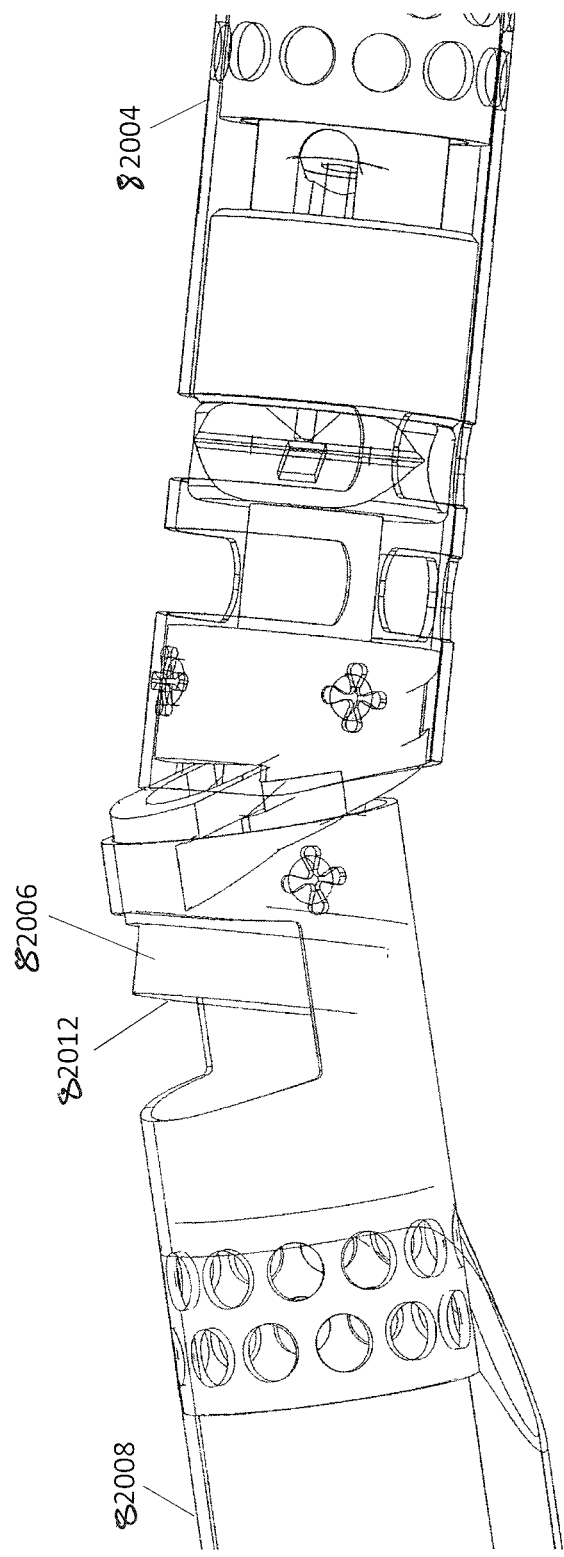
Figure 41G:
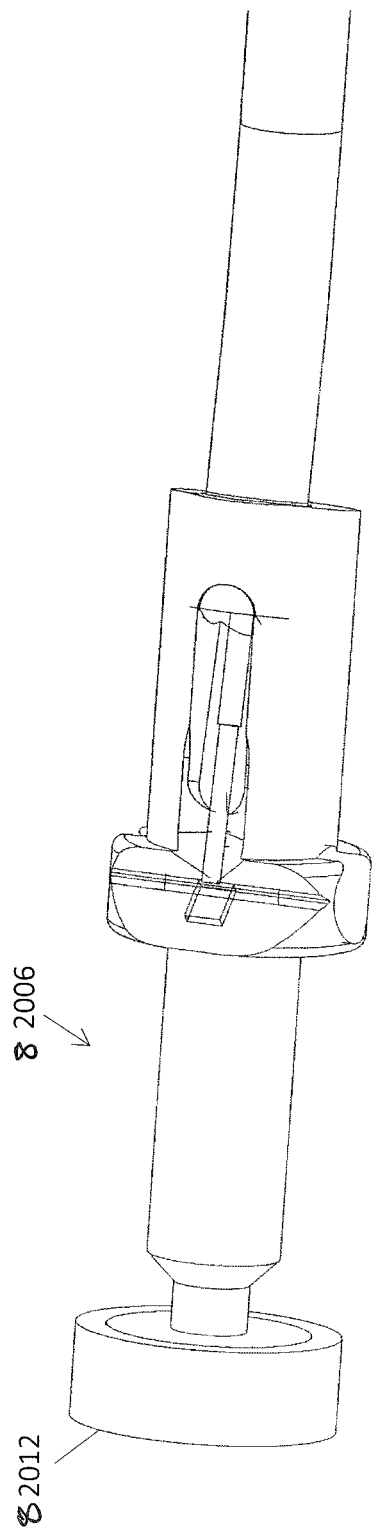
Figure 41J:
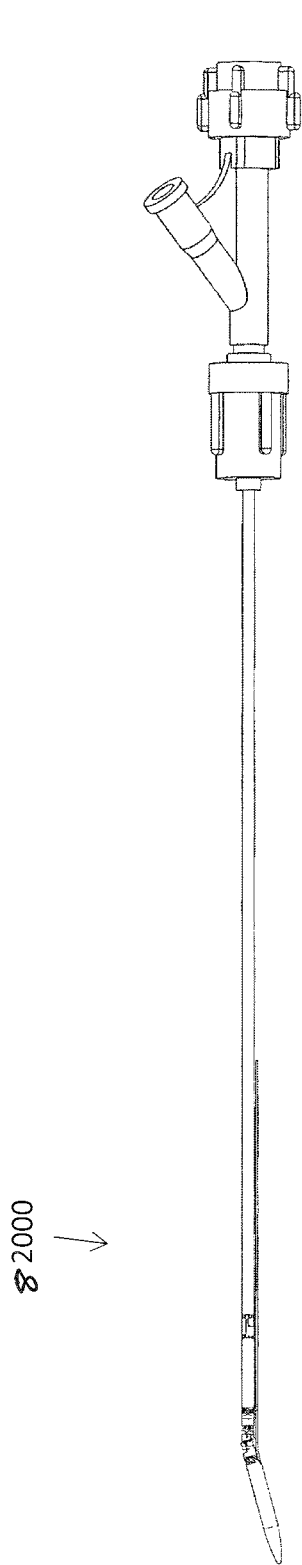
Figure 41K:
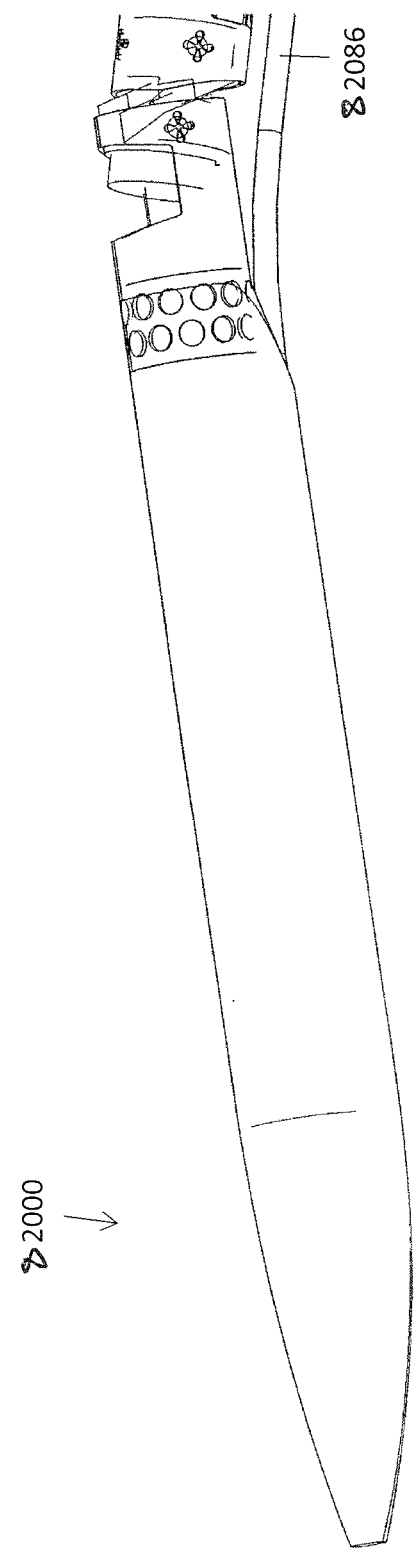

Referring to FIG. 40, a handle 81900 can be configured to enable independent control of the drive shaft and pull shaft translation. This handle 81900 is comparable to that shown in handle 81600 with the addition of a "cutter barrel" 81954 that enables user interaction with the drive shaft that controls the cutter/imaging element location. This cutter barrel 81954 may be translated proximally/distally to open/pack the cutter and imaging element. That is, in use, the cutter barrel 81954 can be pulled proximally to pull the cutter back, and then the pull shaft barrel 81926 can be pulled proximally to drop the nosecone and expose the cutter (pulling the cutter barrel proximally before pulling the pull shaft barrel 81926 proximally ensures proper positioning of the cutter when the nosecone is dropped down). To close the nosecone, the opposite can be done—push the pull shaft barrel 81926 distally to close the nosecone and the push the cutter barrel 81954 forward to pack tissue. A spring 81956 between the pull shaft barrel 81926 and the cutter barrel 81954 can ensure that the cutter is pulled all the way back when the nosecone is opened and keep the cutter pulled back.

The catheter 81400 can further include a flush port close to the cutter. The handle 81600 or the handle 81900 may contain a flush entry port 81658, 81958 that enables the delivery of saline and/or contrast to the distal imaging element location. Flushing at the distal location may be utilized to displace blood to provide a clear OCT image.

FIGS. 41A-41K illustrate another atherectomy catheter 82000. The nosecone 82008 is deflectable from the catheter body 82004 to expose a rotating cutting edge 82012 of a cutter 82012. The cutter 82006 and imaging chassis, to which the end of the optical fiber forming the OCT imaging sensor are coupled, together to rotate. A drive shaft 82016 rotates both the sensor and cutter. In FIGS. 30-41 the system is configured so that lateral (proximal-to-distal) movement of the drive shaft 82016 causes displacement of the nosecone 82008, exposing or protecting the rotating ring cutter 82006.

The optical fiber of the atherectomy catheter 82000 may be held within the central lumen region of the drive shaft 82016 (which is itself within the center of the catheter). In these variations, the optical fiber may be allowed to twist upon itself as the distal tip rotates. The distal end of the optical fiber may be fixedly mounted to the rotating cutter 82006. The end of the fiber may therefore be extended up through the optical fiber chassis or housing to a region near the perimeter of the chassis where it can be directed to a mirror element 82020 to direct the beam out of the catheter and into the surrounding tissue (e.g. vessel). An appropriate epoxy or resin may be used to hold the end of the fiber in place.

For example, when rotating the drive shaft to rotate the cutter 82006 and/or OCT imaging sensor, the drive shaft 82016 may be driven only in one direction. In other embodiments, the shaft 82006 can be rotated approximately 300-500 times clockwise, then the direction of rotation may be reversed, and the cycle (clockwise, counterclockwise) repeated. Thus, an optical fiber within the lumen of the drive shaft may twist 300-500 times then reverse. The fiber may twist in the hollow shaft, which may allow more turns than variations in which wrapping around the drive shaft is used (as illustrated and discussed above). Surprisingly this twisting and untwisting within the lumen may be performed repeatedly without substantially adversely affecting performance of the OCT system and fiber optic. Although the optical fiber is in the center of the catheter (e.g., the center of the drive shaft), it is still off-axis at the distal end of the catheter, where the imaging element is displaced a bit from the edge of the device, as illustrated.

The catheter 82000 can be configured such that movement of the driveshaft 82016 (rotation or lateral movement) and/or movement of the outer shaft (rotation or lateral movement) can be conducted using the magnetic drive system described above.

Figure 35A:
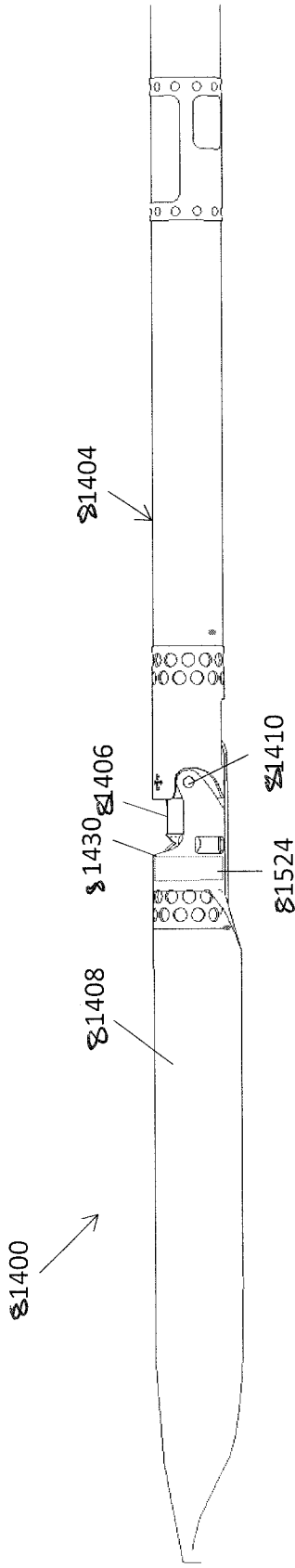
Figure 35B:
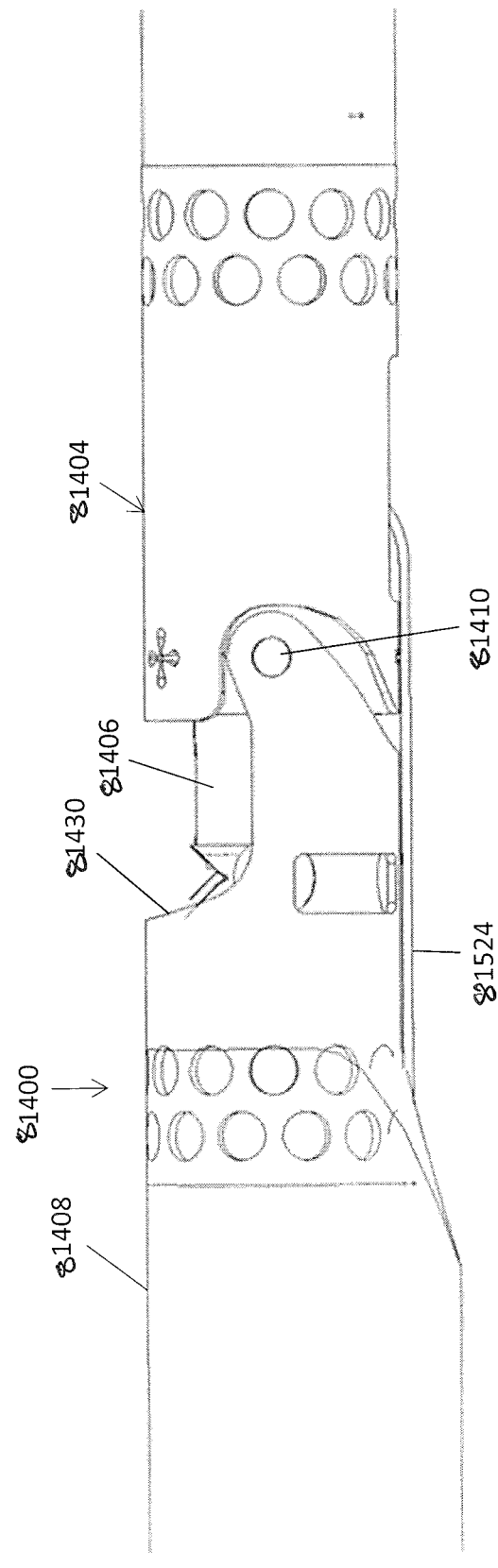
Figure 35E:
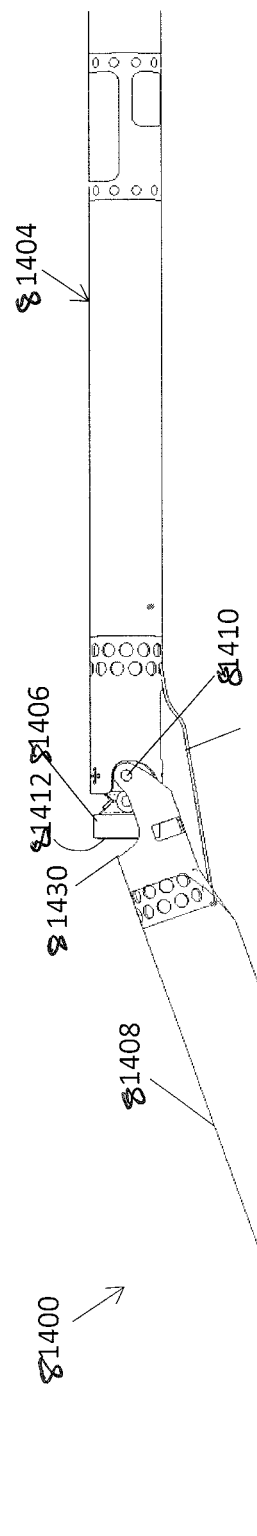

As described above with respect to the atherectomy device 81400 of FIG. 35, the atherectomy device 82000 can include a monorail guidewire channel in the nosecone. An exemplary guidewire 82086 is shown in FIGS. 41G-K extending alongside the catheter.

Further, in some embodiments, the catheter 82000 can be fitted with a pull shaft and/or pull-wire to deflect the nosecone 82008.

A similar atherectomy device is described, for example, in U.S. Pat. No. 9,345,510, filed Jul. 1, 2011, and titled "ATHERECTOMY CATHETERS WITH LONGITUDINALLY DISPLACEABLE SHAFTS," which is incorporated by reference herein.

Figures 42A, 42B:
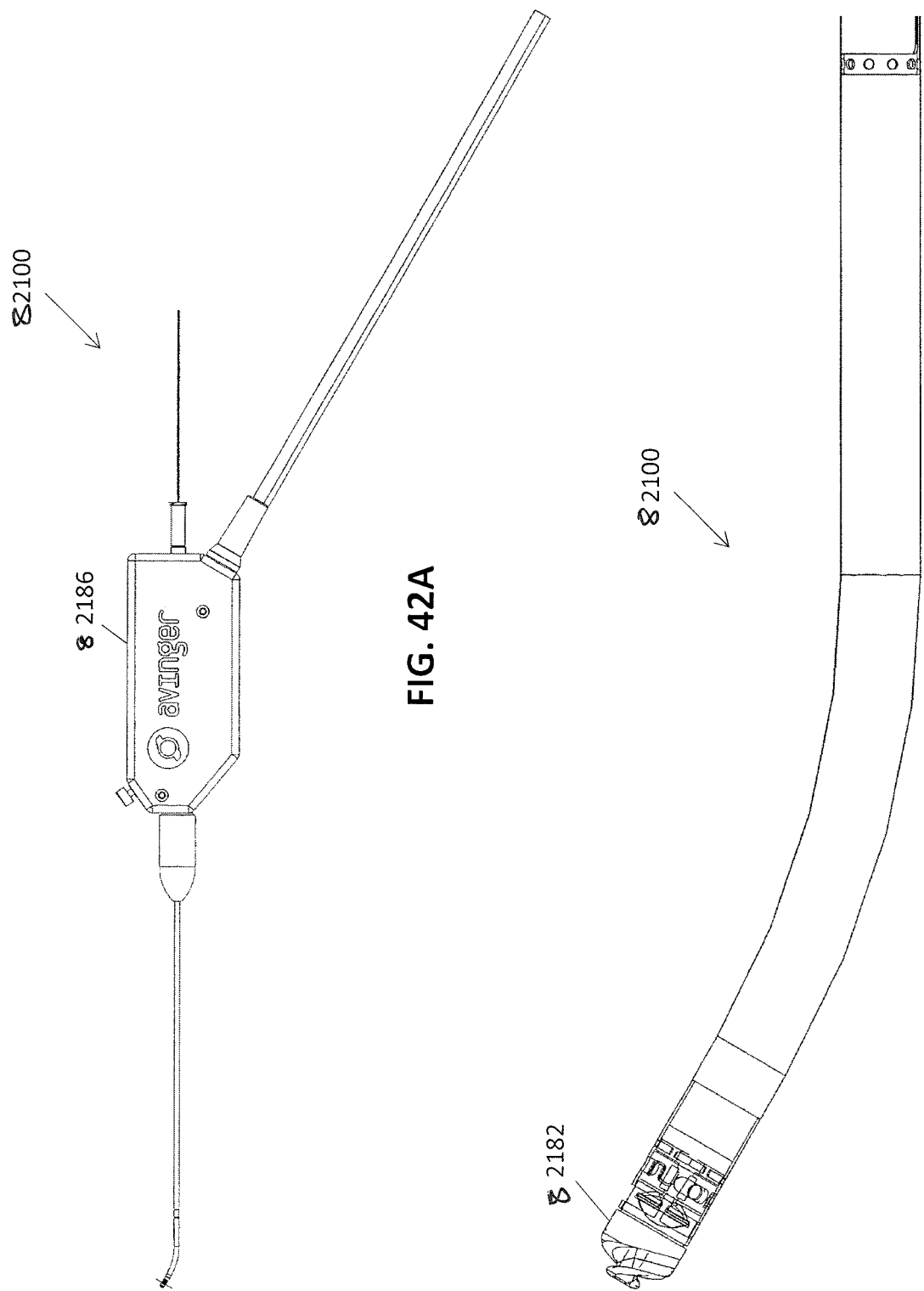
FIGS. 42A-42I illustrate an exemplary guide wire placement catheter that could be used with the non-contact drive systems or pull-wire mechanisms described herein.
Figure 42C:
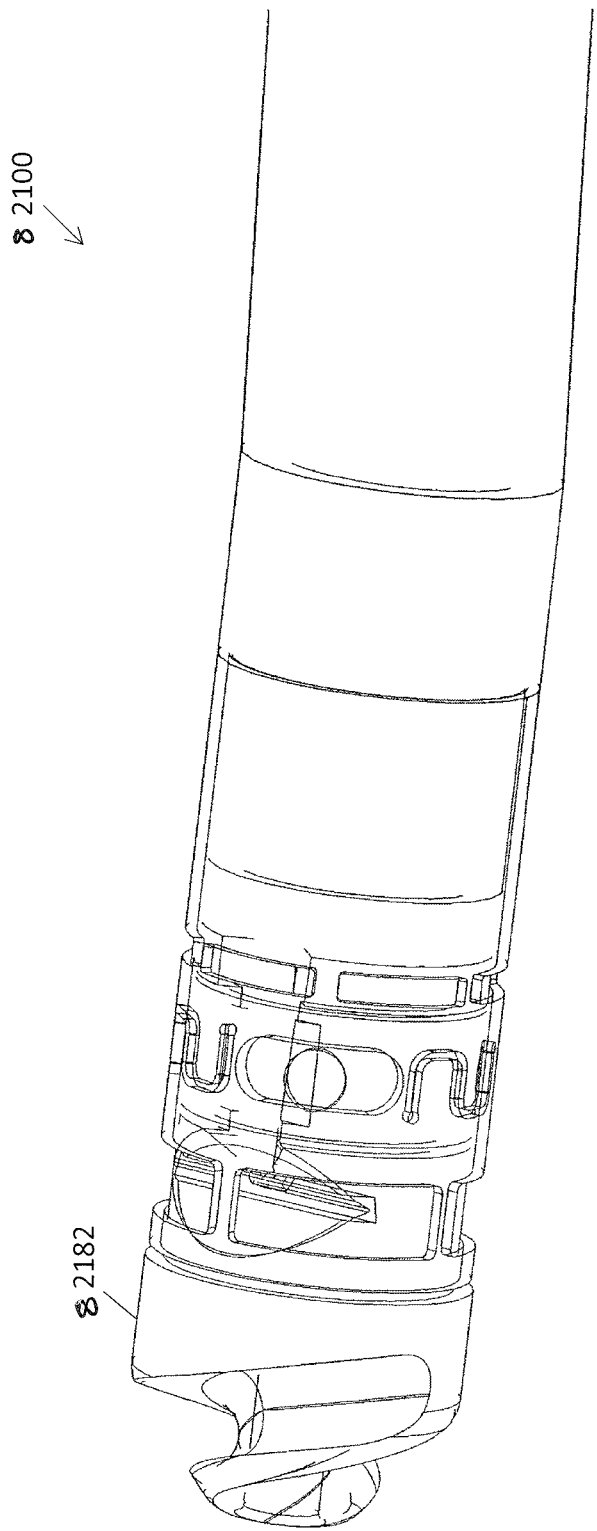
Figure 42D:
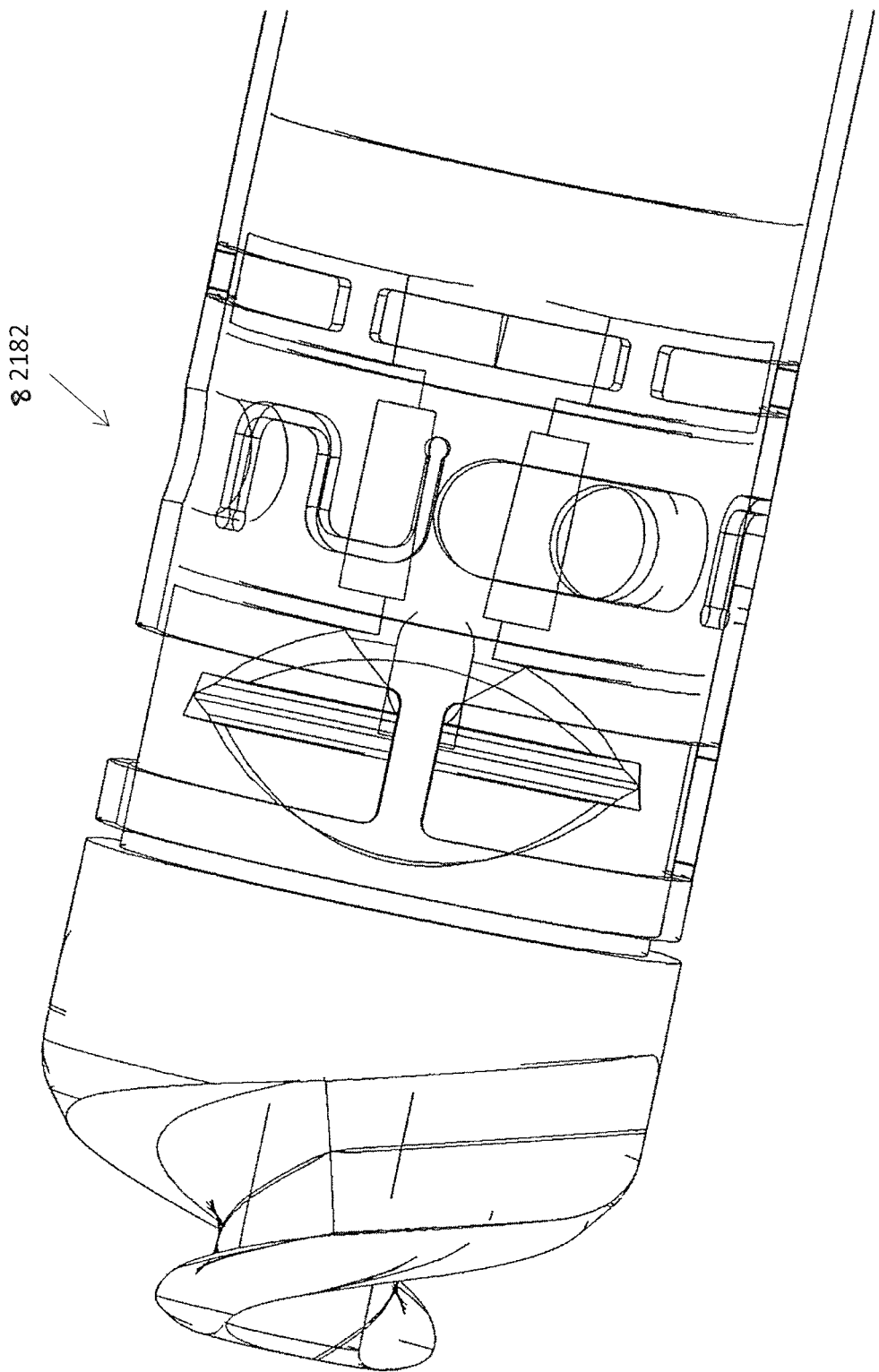
Figure 42E:
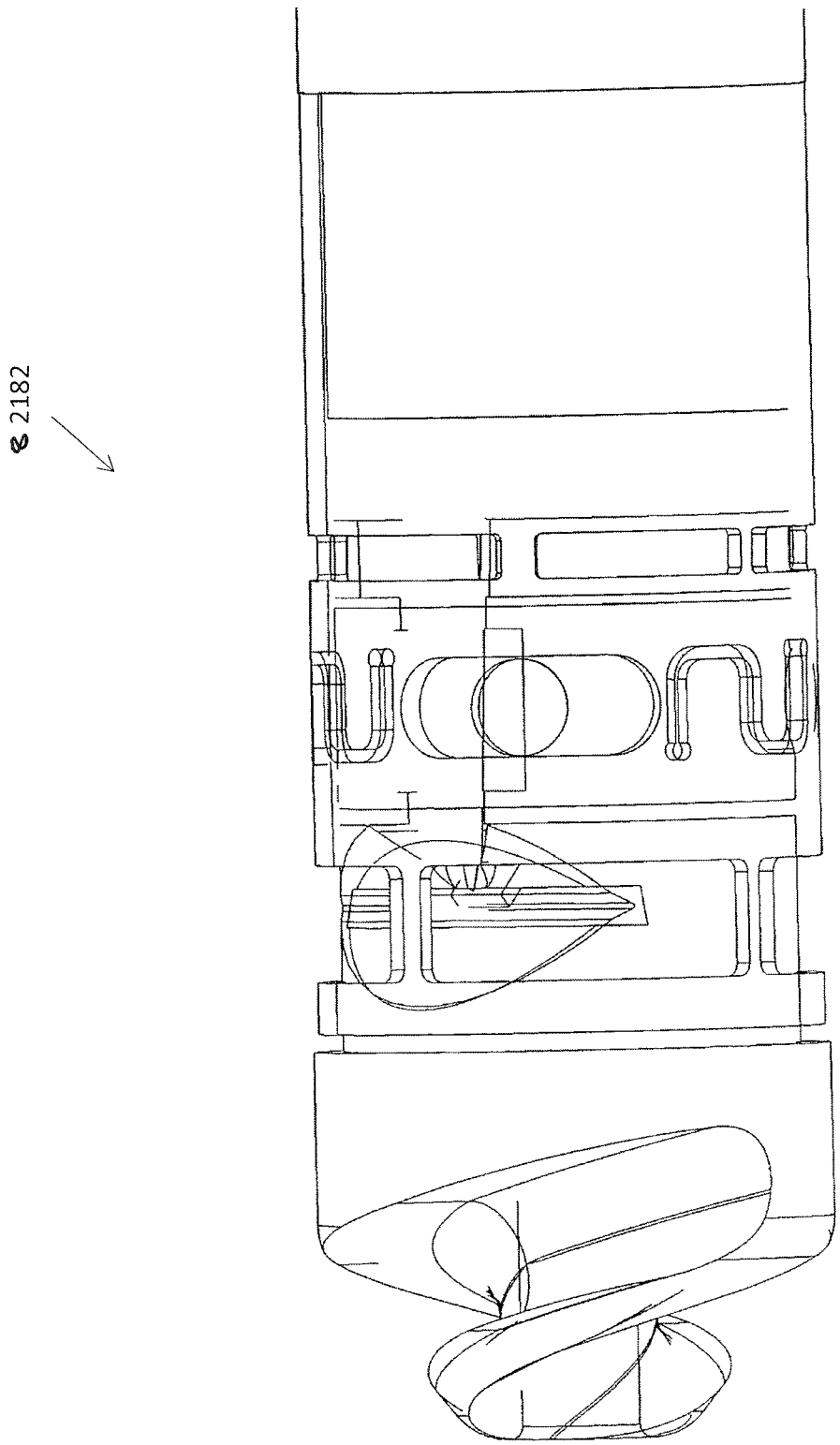
Figure 42F:
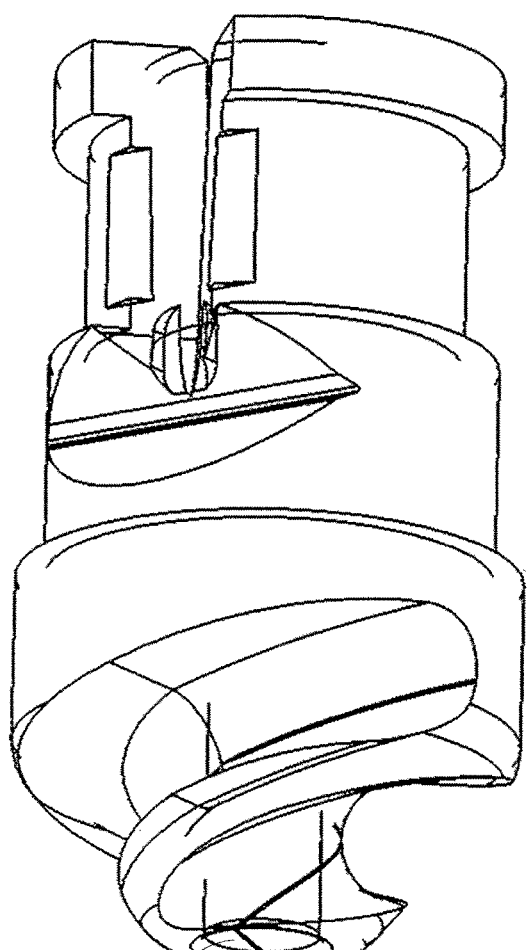
Figure 42G:
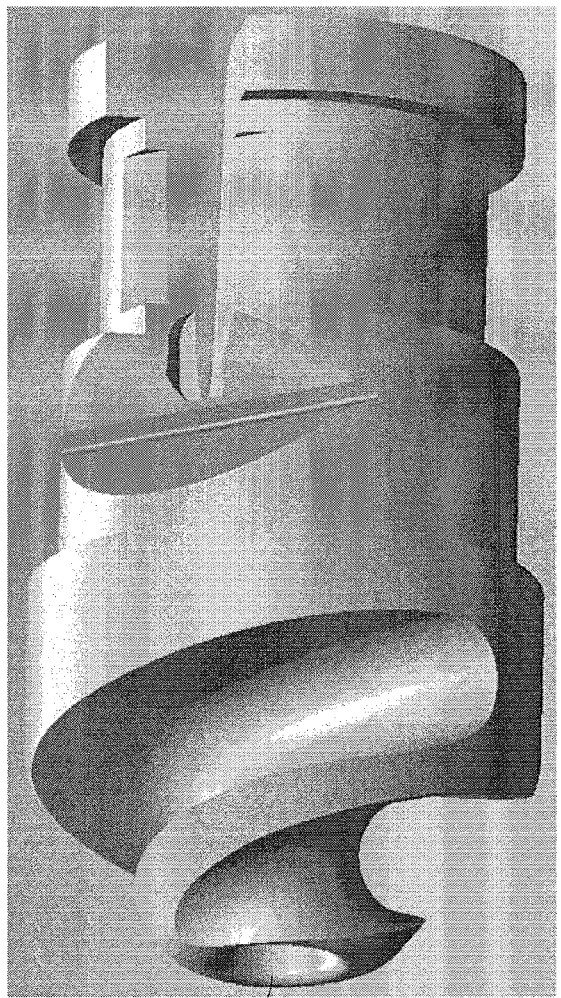

For example, FIGS. 42A-I illustrate another variation of a catheter 82100 that could be used with the magnetic drive system and/or pull-wire mechanism described above. The catheter 82100 is configured as a guidewire placement catheter that includes a rotatable distal tip 82182 and a central lumen 82184 through which a guidewire may be passed, as well as a rotating OCT imaging sensor which includes a fiber optic cable. Devices such as this may be used to cross and position a guidewire through a chronic total occlusion (CTO) without damaging the blood vessel, as would otherwise occur if the guidewire were forced through a CTO. Such devices may be referred to as "CTO crossing devices having imaging" or "CTO imaging and crossing devices." FIG. 42A shows a side view of one variation of a CTO imaging and crossing device for placing a guidewire across a CTO. In this example, the proximal end includes a handle 82186 or controller (shown here as a housing that includes sensor and gearing elements to control operation of the device). FIG. 42B shows an enlarged view of the distal end of the device of FIG. 42A, as do FIGS. 42C-42E. In these figures, the rotatable distal tip 82182 includes a helical cut-out region for engaging (and passing through) CTO material. FIGS. 42F and 42G show just the tip region (rotatable distal tip) of this device. The outer edges of the tip are smooth and curved, to prevent damage to vessel walls. In this example, the tip also includes a mount for the OCT imaging optical fiber, which may form the OCT imaging sensor. Thus, the distal end of the OCT imaging optical fiber may be fixed (e.g., glued, epoxied, etc.) to the rotatable distal tip.

Figure 42I:
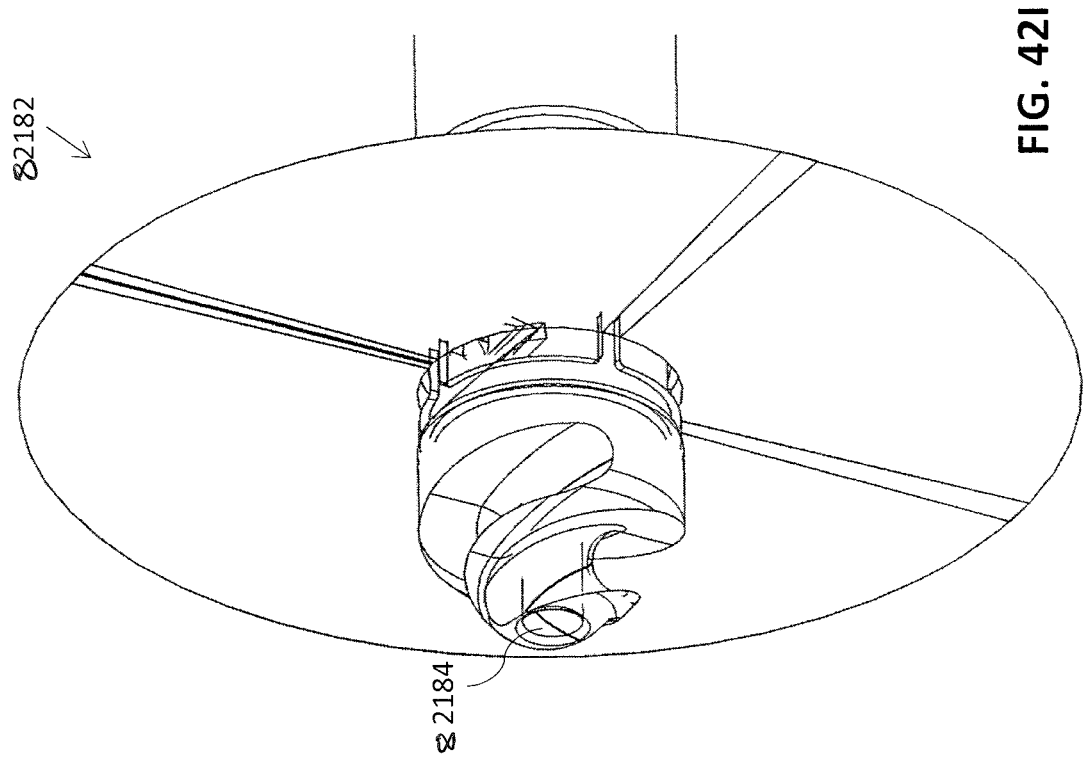
Figure 42H:
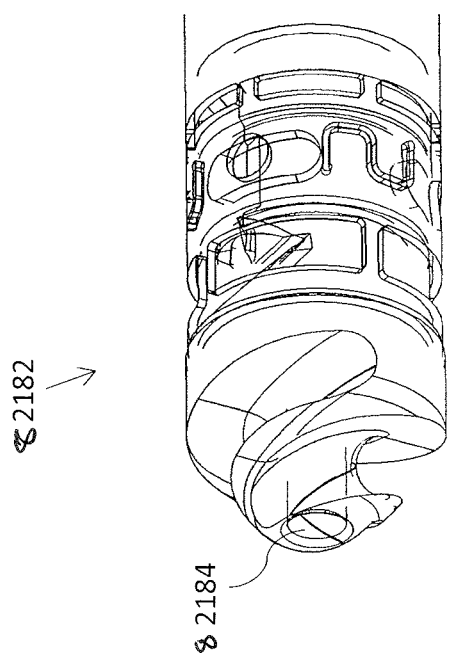

FIG. 42H shows an enlarged view of the distal end of the tip. FIG. 42I shows the same view as FIG. 42H, only with a circular disk indicating the area to be imaged by the rotating OCT sensor (fiber end) as the tip is rotated. Thus, this system may provide a 360° view of the region around the distal tip (e.g., the walls of the vessel, including into the vessel wall). The OCT image may penetrate some depth into the vessel, and therefore allow resolution of different structures at and within the vessel wall. In this example, the viewing field is interrupted by three regions that are blocked from imaging; these regions are arranged to allow fiducial markings around the perimeter; the entire catheter tip region may be rotated to change the position of these occluded regions.

Activation of the distal tip 82182 can be controlled by a driver, such as the magnetic driver described above. Further, the catheter 82100 could be fitted with a pull-wire mechanism similar to that described above, for example if there were a housing on the distal end of the catheter to protect the rotating distal tip when not in use.

A similar occlusion-crossing device is described in U.S. Pat. No. 8,644,913, filed Mar. 28, 2012, and titled "OCCLUSION-CROSSING DEVICES, IMAGING, AND ATHERECTOMY DEVICES", which is incorporated by reference herein.

In some embodiments, the catheters described herein can be used with a non-contact catheter drive system.

The non-contact catheter drive systems described herein include a magnetic driver having one or more drive elements that can be kept separate from the catheter to interact magnetically with a response element that is part of or attached to the catheter. The magnetic driver magnetically engages the catheter response element to actuate elements of the catheter without directly contacting the catheter or the catheter handle. Because this system allows non-contact control of the catheter (e.g., rotation of a drive shaft in the catheter), the sterile filed surrounding a patient may be kept intact even when using a non-sterile magnetic driver. For example, the magnetic driver can be covered in a sterile covering (e.g., a bag or sheet) that can be kept intact (not ripped or subject to tearing) while still engaging the catheter to drive actuation, such as rotation, steering, or lateral movement, of one or more elements of the catheter.

In general, a non-contact catheter driver may include one or more drive elements that can cause a moving magnetic field of sufficient strength to drive movement of a magnetic response element in a catheter that is placed (e.g., secured) within a channel of the non-contract catheter driver. A sterile drape or the like may be paced between the non-contract catheter driver and the catheter that it is driving; the drape does not interfere with the activity of the driver and the driver does not need to break the sterile field (e.g., drape) to operate on the catheter.

Figure 22:
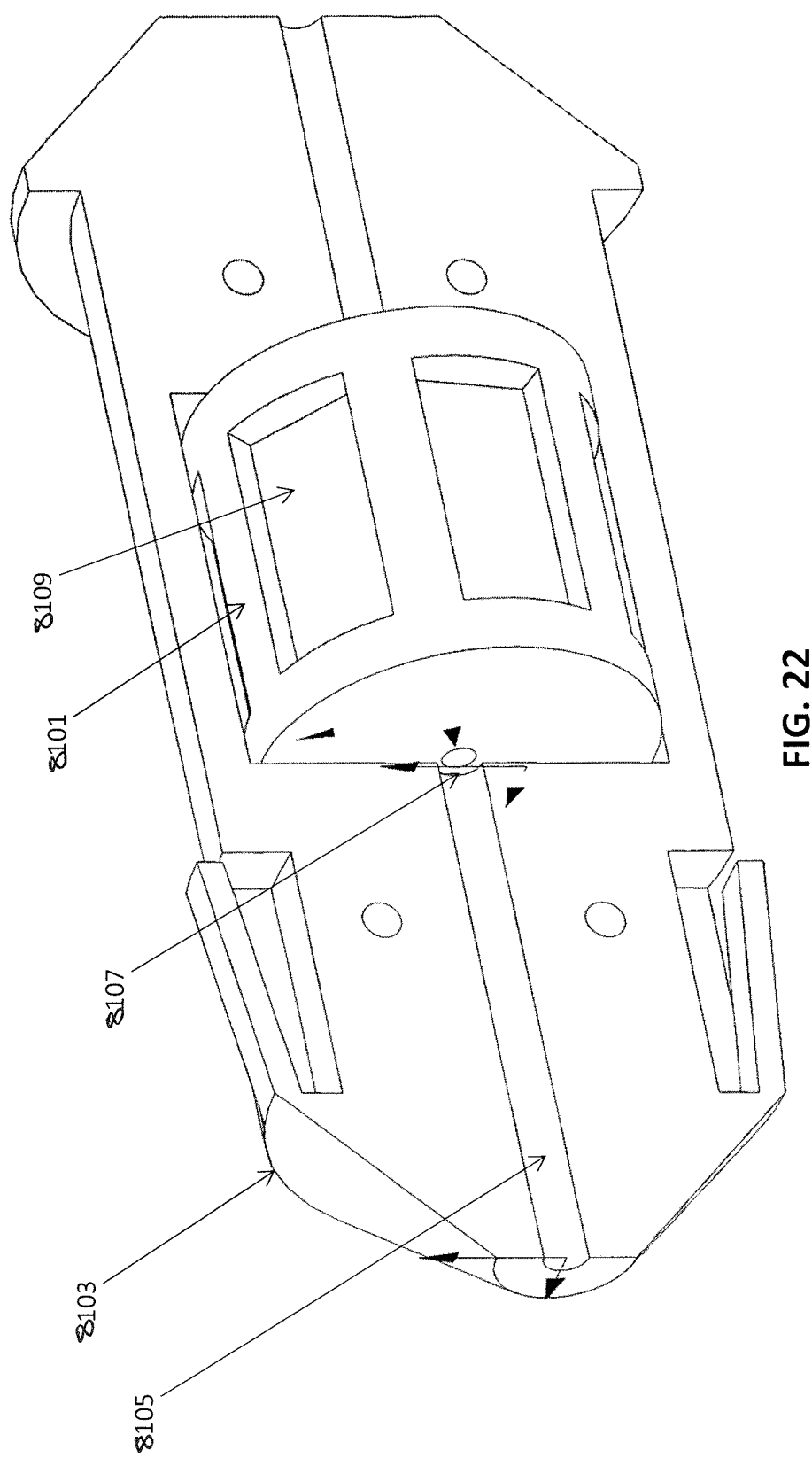
FIG. 22 shows one variation of a magnetic response element that can be attached to a shaft of a catheter for rotating the shaft.
Figure 23:
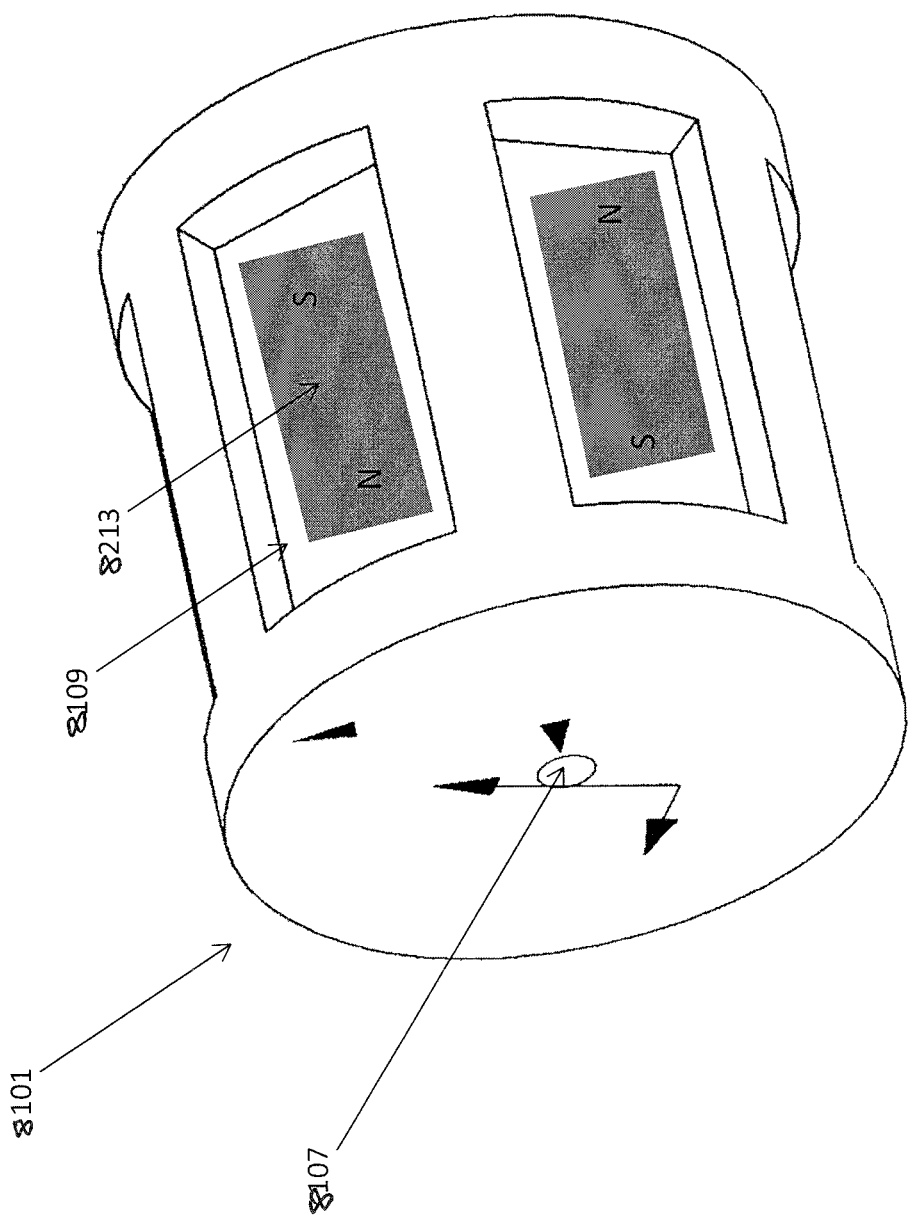
FIG. 23 shows a close-up of the bearing of the magnetic response element of FIG. 22.
Figure 24:
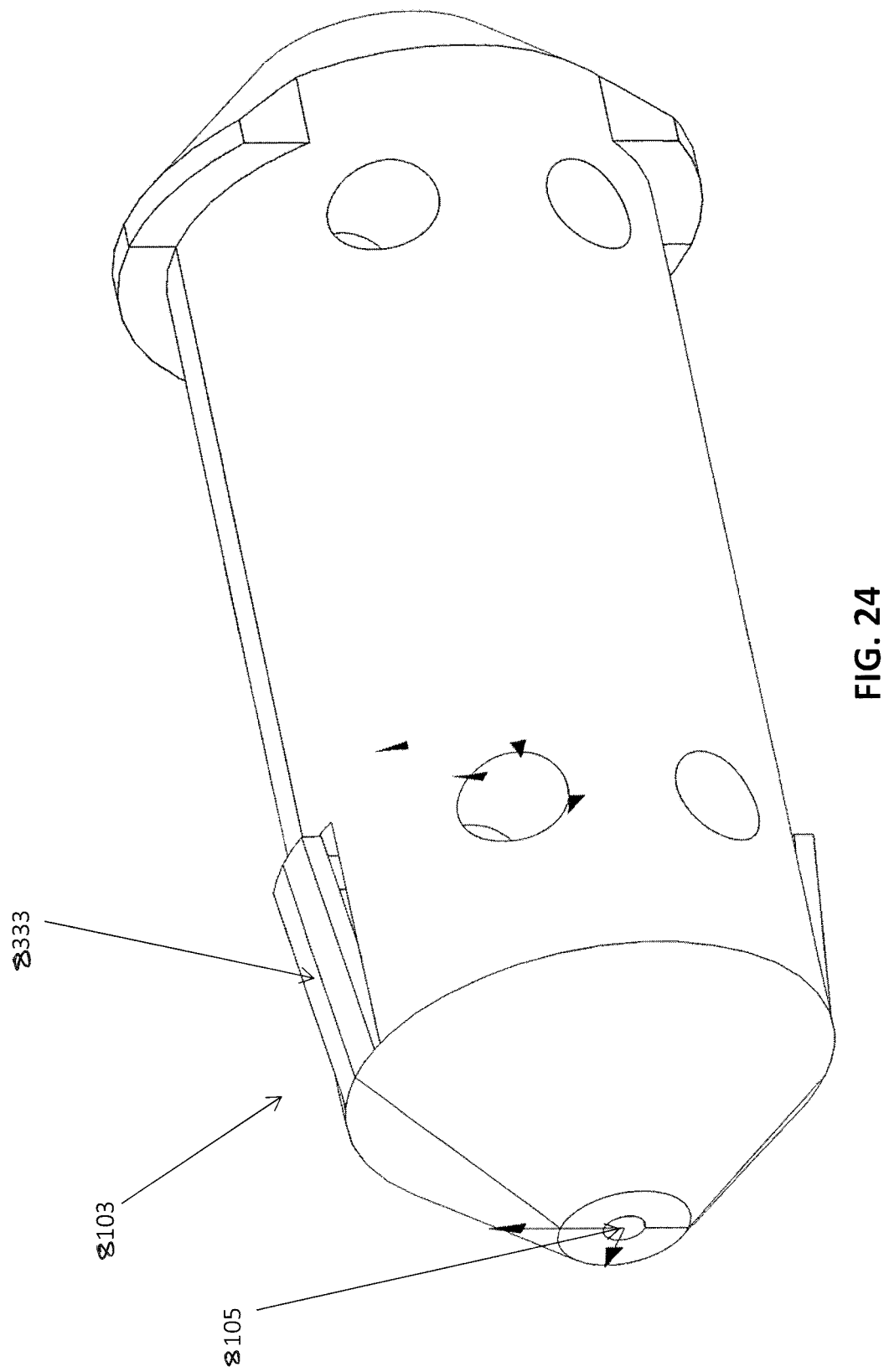
FIG. 24 shows the outer housing of the magnetic response element of FIG. 22.

FIGS. 22-24 illustrate one variation of a magnetic response element that can be coupled to a rotatable drive shaft within a catheter. Referring to FIG. 22, a magnetic response element 8100 can include a housing 8103 having a channel 8105 therethrough for engagement with a driveshaft of a catheter. The response element 8100 can further include a central magnetic bearing 8101. The bearing 8101 can include a bearing channel 8107 configured to fixedly attach to a driveshaft of the catheter (e.g. through glue, etc.). The bearing 8101 can rotate within the housing 8103, thus causing the catheter driveshaft to rotate as well (the driveshaft will rotate with the bearing 8101 and relative to the housing 8103).

The bearing 8101 can include a set of magnetic holders 8109, such as pockets in the bearing 8101, configured to hold magnetic domains of opposite polarity (i.e., N, S, N, S). There can be, for example 1-20 magnetic holders 8109 arranged around the circumference of the bearing 8101. A simple arrangement of a six holders 8109 around the circumference of the bearing 8101, each holder 8109 with a single magnet 8213, is shown in FIG. 23. In other embodiments, two or more magnets can be arranged per holder. As described further below, the magnetic domains can interact with a magnetic driver to drive rotation of the catheter shaft.

In some embodiments, there can be multiple magnetic response elements 8100 for use with a single catheter to drive different shafts within the catheter (for example, to drive rotation of a cutting element and rotation of the cutter).

Further, in some embodiments, there can be multiple magnetic response elements 8100 arranged in series and fixed to a single driveshaft. In one configuration, each response element 8100 in the series can include a different number or arrangements of magnetic domains or magnets 8213 therein, such that the shaft can be configured to counter-rotate and/or rotate at different speeds. In another configuration, each response element 8100 of the series can have the same arrangement of magnetic domains or magnets 8213 there, but the series alignment can advantageously provide more torque for rotating the driveshaft.

As shown in FIG. 24, the housing 8103 having a channel 8105 therethrough for engagement with a driveshaft of a catheter. The housing 8103 can further include a locking mechanism, such as a snap lock 8333 configured to keep the housing 8103 from sliding within the driver once mounted.

FIGS. 25A-27B illustrate one variation of a magnetic driver that may be mounted or held and which may engage the magnetic response element to drive rotation of the drive shaft in the device. The driver can secure the catheter within the sterile field.

Figure 25A:
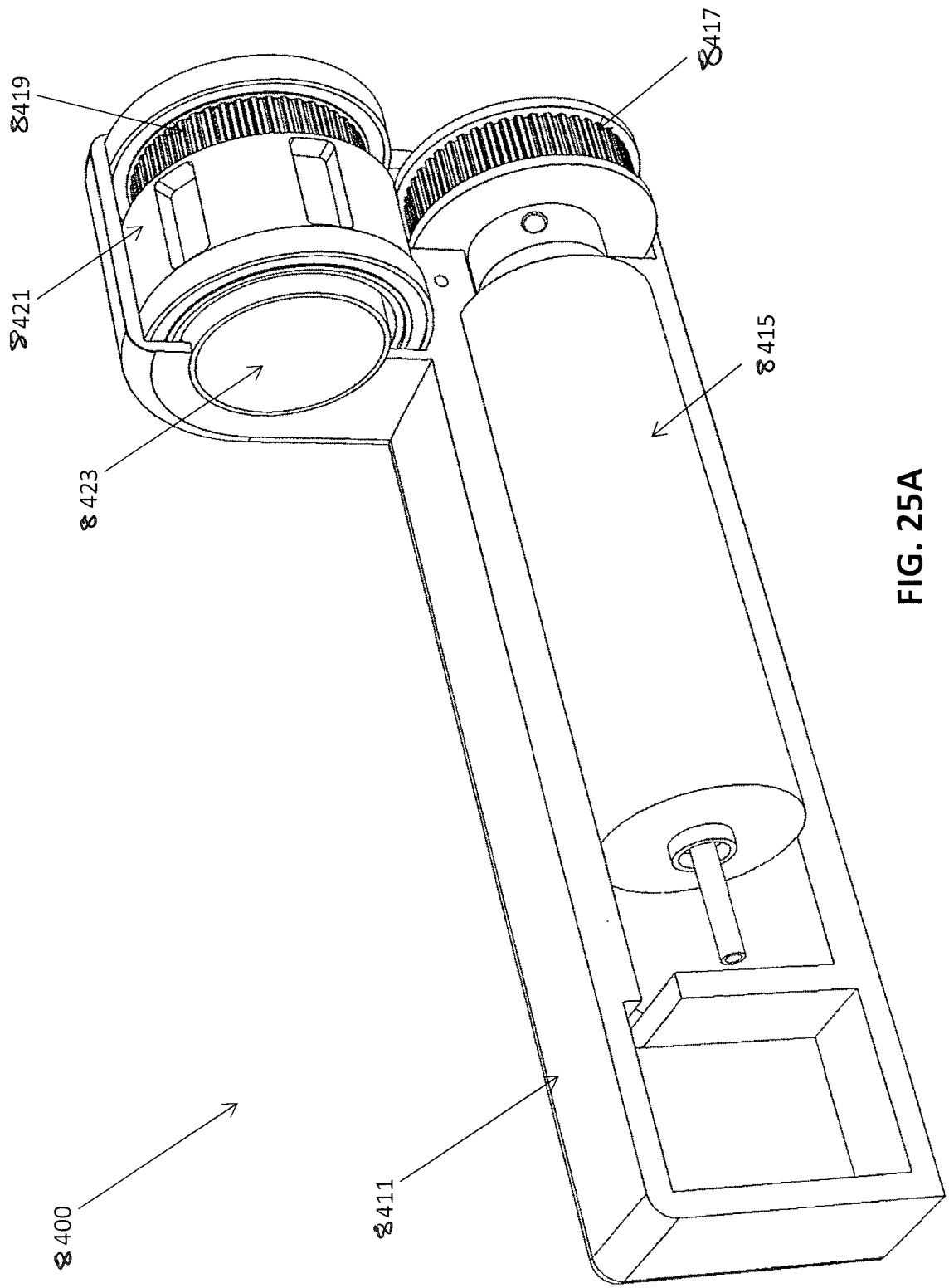
FIGS. 25A-25B show one variation of a magnetic (non-contact) driver configured to engage with a magnetic response element such as the one shown in FIGS. 22-24 to drive rotation of the catheter shaft
Figure 25B:
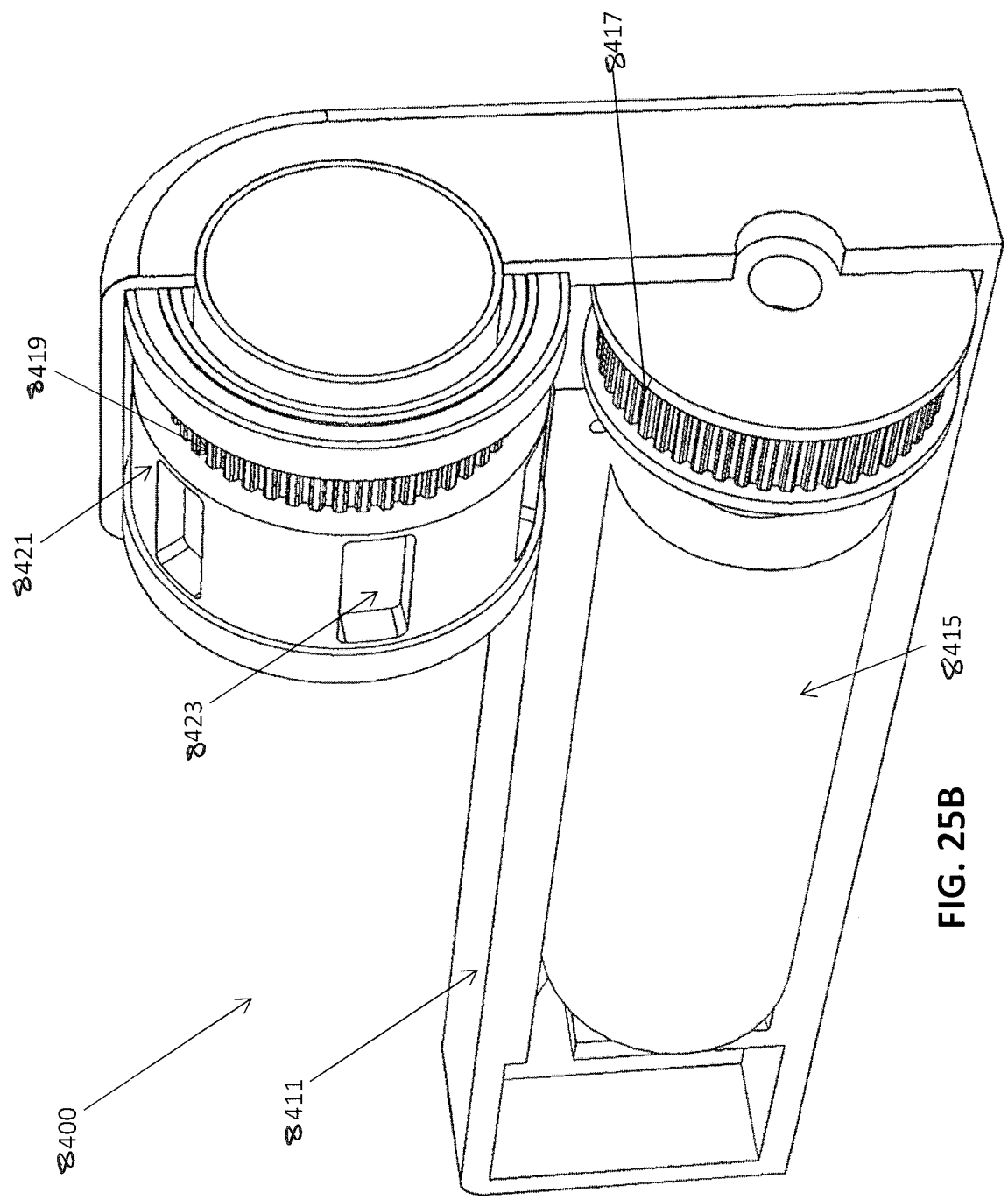

Referring to FIGS. 25A-25B, a magnetic driver 8400 includes a housing 8411 having a connector 8423, such as a cylindrical channel or opening, for engagement with a response element, such as response element 8100. The connector 8432 can include a mechanism configured to interlock with the locking mechanism on the housing 8103 of the response element 8100, such as to interact with the snap lock 8333.

The magnetic driver 8400 can further include a motor 8415 connected to a first gear 8417. The first gear 8417 can be engaged with a second gear 8419 through a belt 8525 (see FIG. 26). The second gear 8419 can be connected to a drive rotor 8421. The drive rotor 8421 can include magnetic holders 8409, such as pockets in the rotor 8421, configured to hold magnetic domains.

Figure 26:
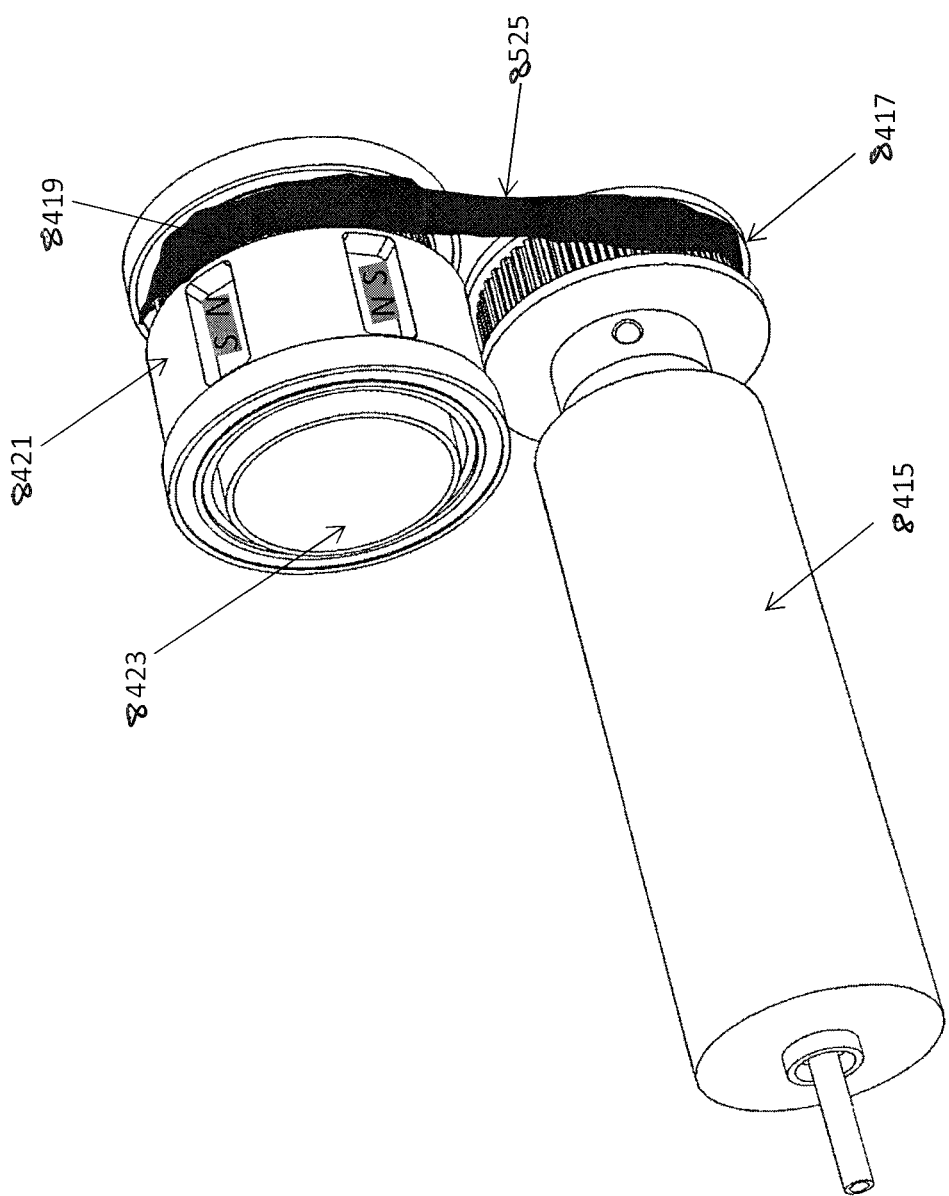
FIG. 26 shows the pulley system used to drive the gears and thus the rotor of the driver of FIGS. 25A-25B.

The holders 8409 and/or the magnetic domains in the pockets can be configured so as to align with (but of opposite polarity to) the holders 8109 and domains of the response element, such as response element 8100. Thus, for example, there can be six holders 8409, each with a single magnet 8513, as shown in FIG. 26.

Figure 27A:
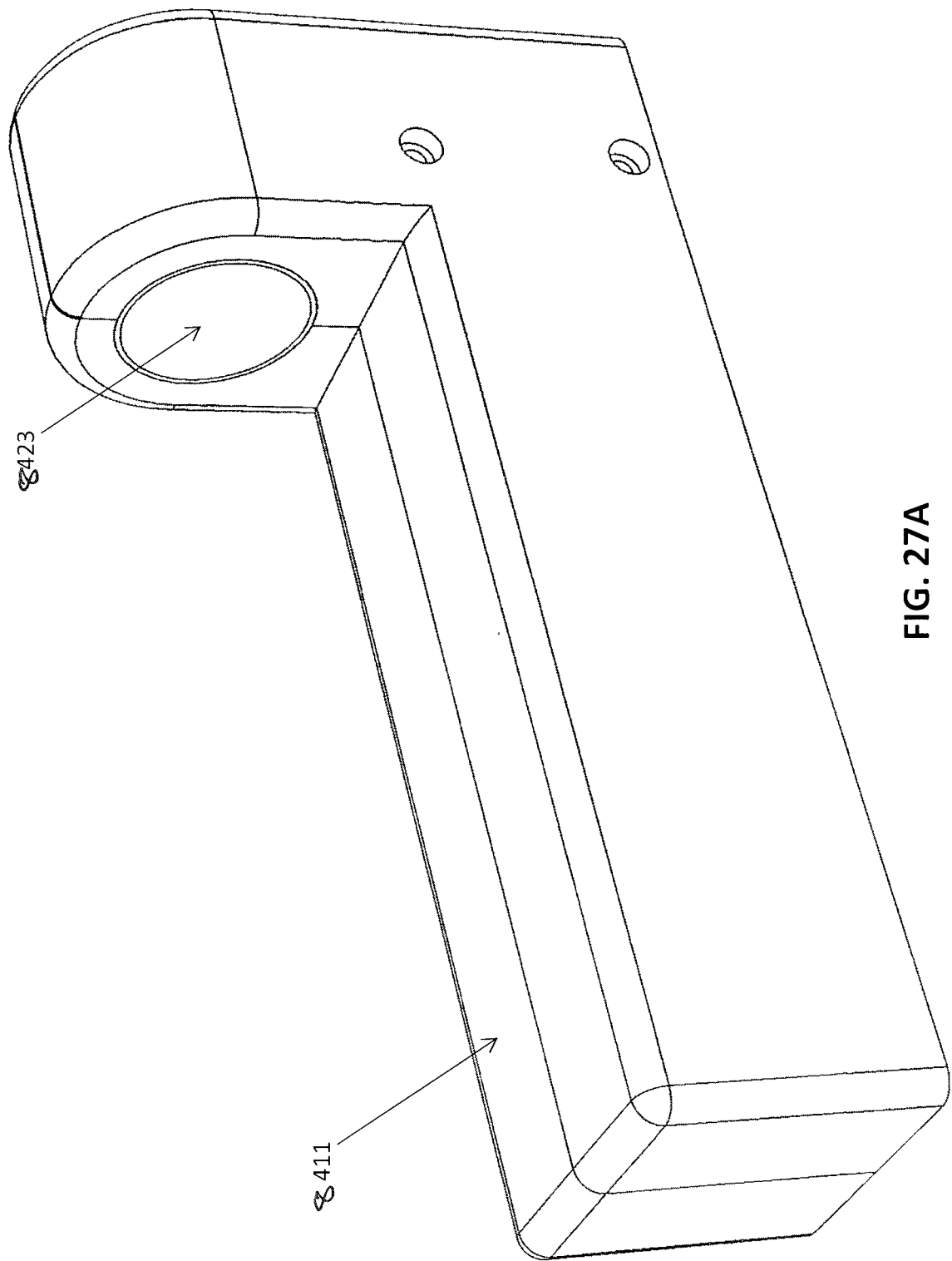
FIGS. 27A-27B show the outer housing of the driver of FIGS. 25A-25B.
Figure 27B:
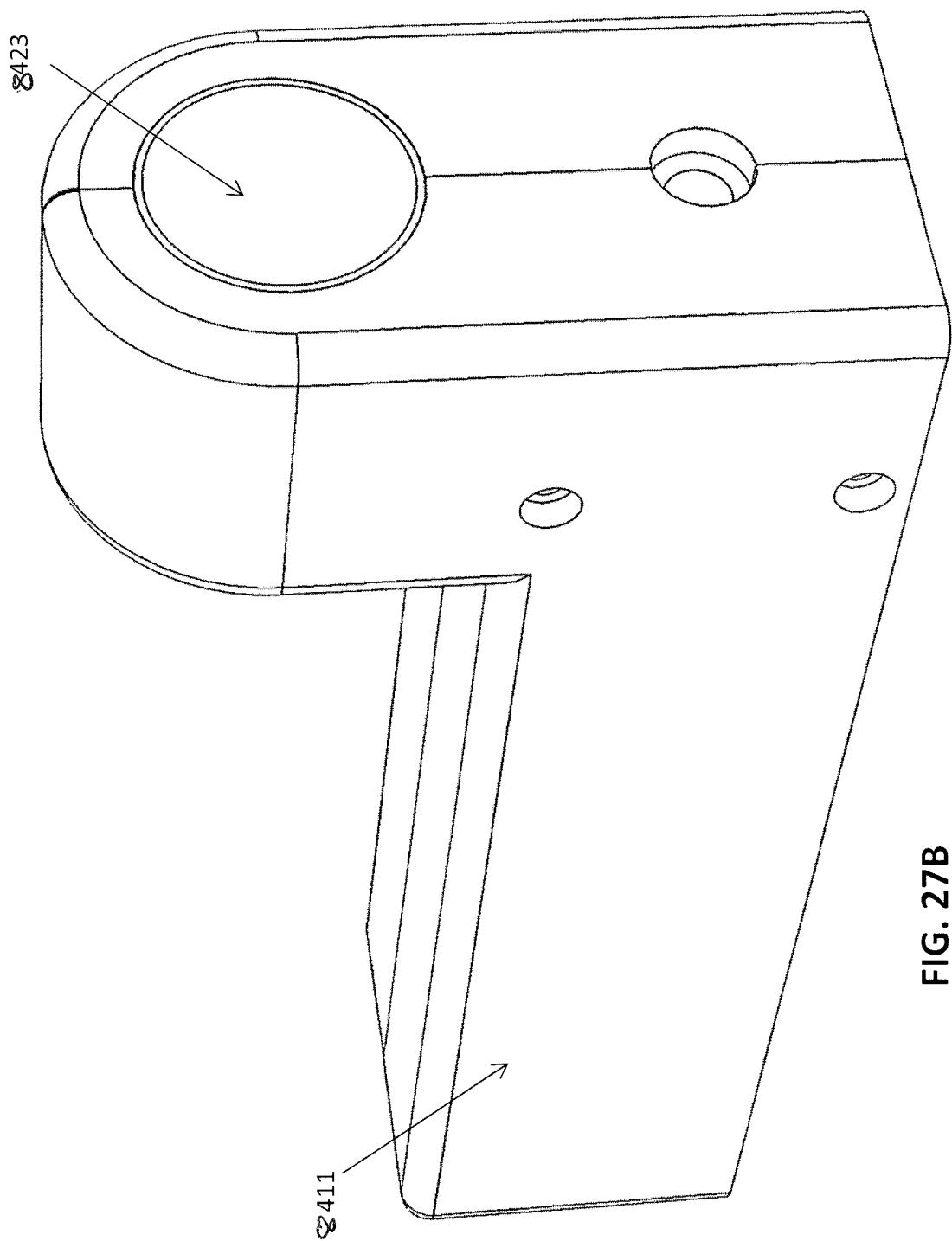

As shown in FIGS. 27A-27B, the housing 8411 includes a connector 8423 for engagement with the response element 8100. The connector 8423 can be a hollow channel, which can have an uninterrupted sealed interior.

The magnetic driver 8400 can be used to drive rotation of a catheter having a response element, such as response element 8100. In one embodiment, the housing 8103 of response element 8100 can be configured to slide into the opening of the connector 423. As the housing slides in, the magnetic domain of the response element 8100 can align with the magnetic domain of the driver. For example, the magnets 8513 shown in FIG. 26 can align with the magnets 8213 shown in FIG. 23. As such, when the motor 8415 is activated, it can turn the first gear 8417, which will activate the belt 8525, turning the second gear 8419 and thus the rotor 8421. Due to the interaction between the magnets 8513 on the rotor 8421 and the magnets 8213 on the bearing 8101, the bearing 8101 will rotate, thus causing the driveshaft connected thereto to rotate in the same clockwise/counter-clockwise direction as the gears 8417, 8419. Such rotation of the driveshaft can thus provide for cutting, imaging, etc. of a catheter. Thus, while the catheter and housing 8103 of the response element 8100 remain static, the driveshaft can be rotated by the interaction between the magnetic domains.

Advantageously, by using this this non-contact drive system, the catheter can remain sterile while the magnetic driver 8400 can be in the non-sterile field. For example, a sterile bag or sheet can be placed over the housing 8101 or lined within the connector 8423 to avoid direct contact between the catheter and the magnetic drive 8400.

Although the response element 8100 is described above for use with a driveshaft of a catheter, it can likewise be used for any shaft of a catheter, such as an outer torque shaft.

Figure 28:
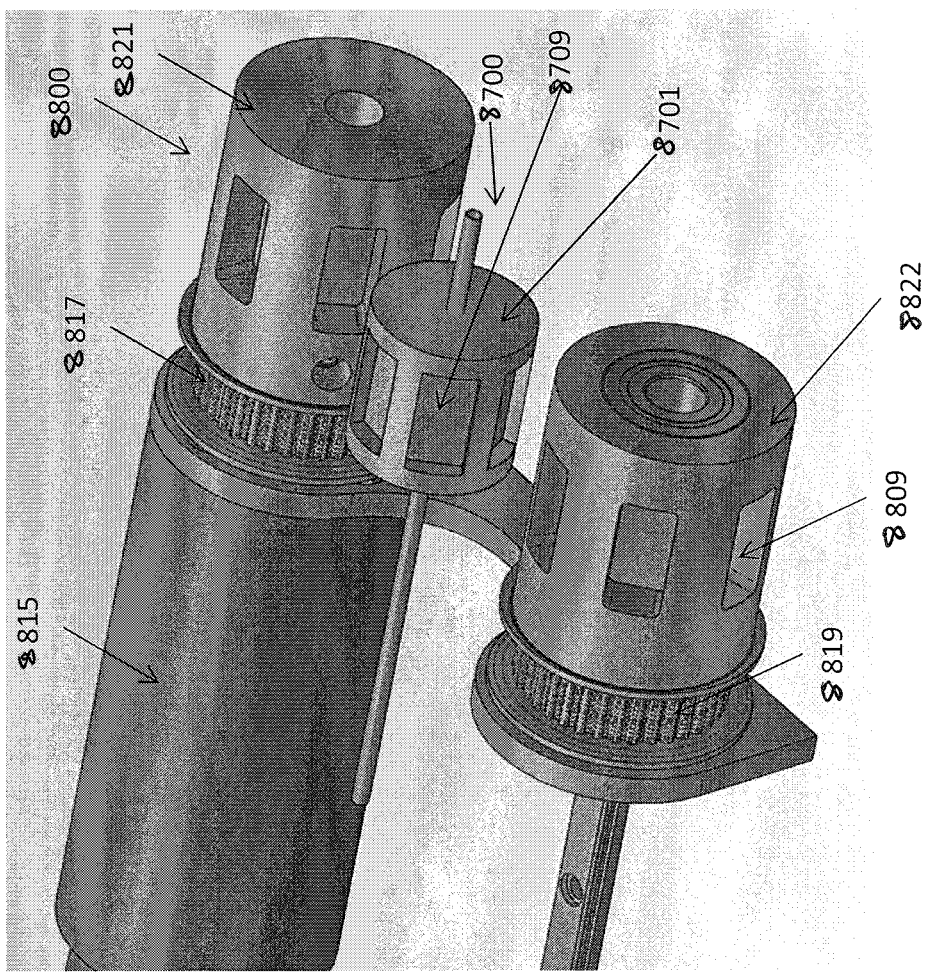
FIG. 28 shows another variation of a system for magnetic, non-contact rotation of a shaft of a catheter.
Figure 29:
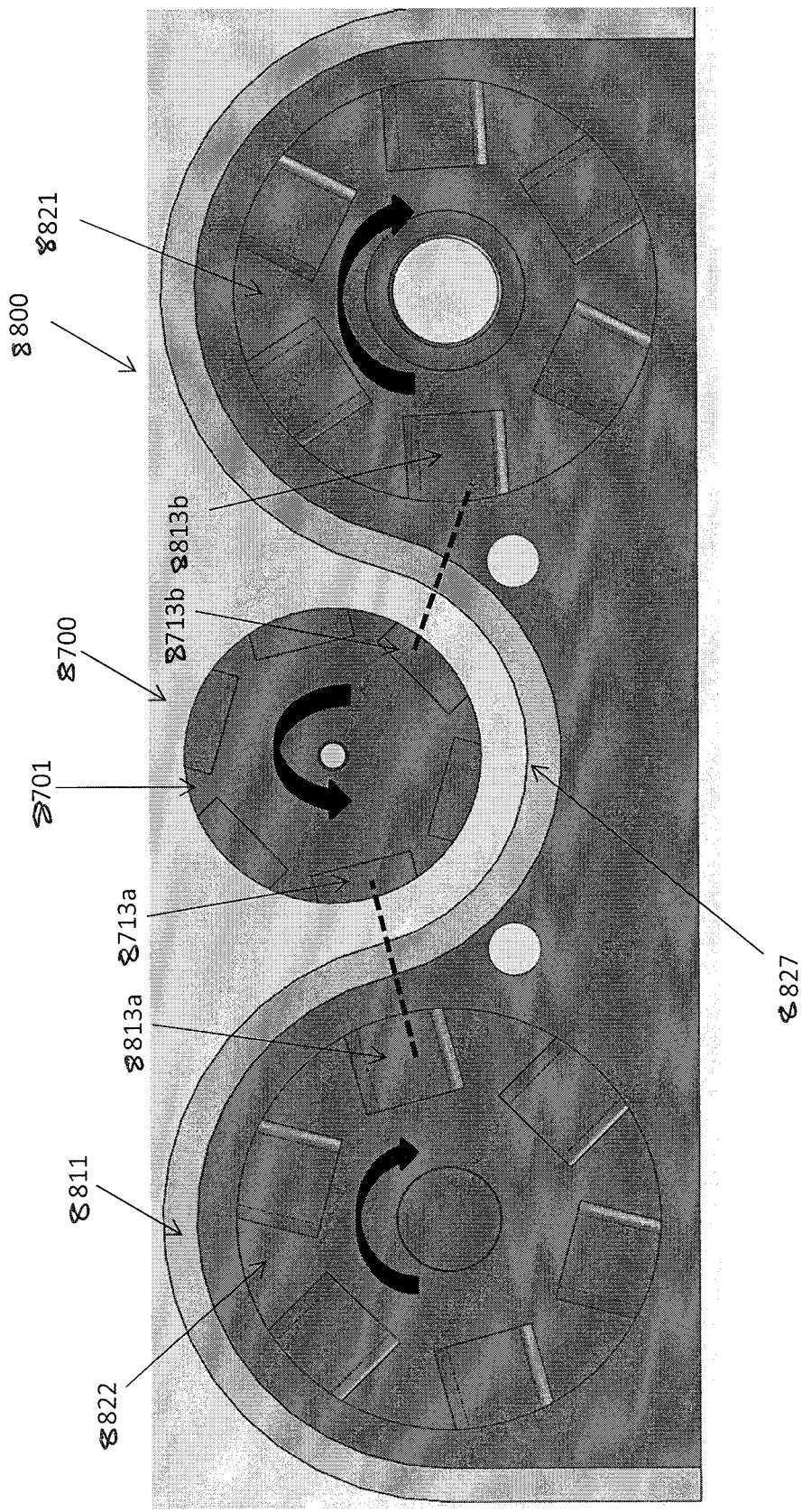
FIG. 29 is a cross-section of the system of FIG. 28.

FIGS. 28-29 illustrate another variation of a non-contact system including a response element and a driver that can impart rotational motion into a shaft of a catheter, such as a drive shaft or torque shaft. The response element 8700 can be configured similarly to the response element 8100. It can thus include a bearing 8701 having a bearing channel 8707 configured to fixedly attach to a shaft of the catheter. The bearing 8701 can include a set of magnetic holders 8709, such as pockets in the bearing 8701, configured to hold magnetic domains of opposite polarity, such as single magnets 8713 (see FIG. 29).

The magnetic driver 8800 can include a motor 8815 connected to a first gear 8817. The first gear 8817 can be engaged with a second gear 8819 through a belt extending between the gears 8817, 8819. In this embodiment, the first gear 8817 can be connected to a first rotor 8821 while the second gear 8819 can be connected to a second rotor 8822. Each of the rotors 8821, 8822 can include magnetic holders 8809, such as pockets in the rotors 8821,8822, configured to hold magnetic domains. The holders 8809 and/or the magnetic domains in the holders can be configured so as to align with (but of opposite polarity to) the holders 8709 and domains of the response element 8700. Thus, each rotor 8821, 8822 contain magnets 8813 (see FIG. 29) mounted with polarity opposite that of the adjacent magnet on the same rotor so as to create an alternating magnetic field. This may ensure proper "meshing" and alignment of the virtual magnetic gearing of the response element and driver. The magnetic driver 8800 can be contained within a housing 8811 (see FIG. 29) having a crevice or channel 8827 configured to hold the response element 8700, i.e., to allow the response element 8700 to rest therein.

The magnetic driver 8800 can be used to drive rotation of the shaft of the catheter to which the response element 8700 is attached. To do so, the response element 8700 (connected to the shaft of the catheter) can be placed in the channel 8827. The response element 8700 will thus sit between the first and second rotors 8821, 8822. When the motor 8715 is activated, it will turn the first gear 8717, which will activate the belt and thus turn the second gear 8719. As the gears 8717, 8719 turn, the rotors 8821, 8822 will turn. The rotation of the rotors 8821, 8822 will cause the bearing 8701 to rotate in the opposite direction (e.g. clockwise if the rotors 8821, 8822 are rotating counterclockwise) due to the interaction between the domains on the bearing 8701 and the domains on the rotors 8821.

For example, as shown in FIG. 29, the magnet 8713a will interact with the magnet 8813a. As the rotor 8821 spins clockwise, the attraction between the two magnets 8713a, 8813b will cause the bearing 8701 to spin counterclockwise. As it does so, the magnets 8713b and 8813b will come closer together, thereby causing the attraction between those magnets 8713b, 8813b to continue the counterclockwise spin of the bearing 8701. Continuous interaction between the magnets 8813 of the clockwise-rotating rotors 8821, 8822 and the magnets 8713 of the bearing 8701 will thus cause the bearing 8700 to continue to rotate counterclockwise.

In one embodiment, the rotors 8821, 8822 are aligned such that the holders 8709 in each respective rotor 8821, 8822 are slightly offset from one another (as best seen in FIG. 29). This offset can advantageously provide a smoother rotation of the bearing 8701 by allowing the magnets 8713 thereon to interact with a magnet 8813 of the first rotor 8822, followed by interaction with a magnet 8813 of the first rotor 8821, etc. Such back-and-form transitioning between the magnets of the first and second rotors 8811, 8822 avoids having a slowing or jolting of the bearing 8701 rotation that might otherwise occur if magnets 8813 of both rotors 8821, 8822 interacted and then disengaged simultaneously.

The response element 8700 driver 8800 can advantageously allow non-contact actuation of a driveshaft of a catheter. As a result, the catheter can be actuated while maintaining a sterile field. For example, a sterile bag or sheet can be placed over the housing 8811 and/or such that it lines the channel 8827 to separate the sterile and non-sterile field. Because the catheter with the response element 8700 can simply be placed on top of the housing 8811 to actuate the driveshaft, the system provides easier sterility options than those where snapping or physical connection of the catheter and the driver are required.

Figure 30:
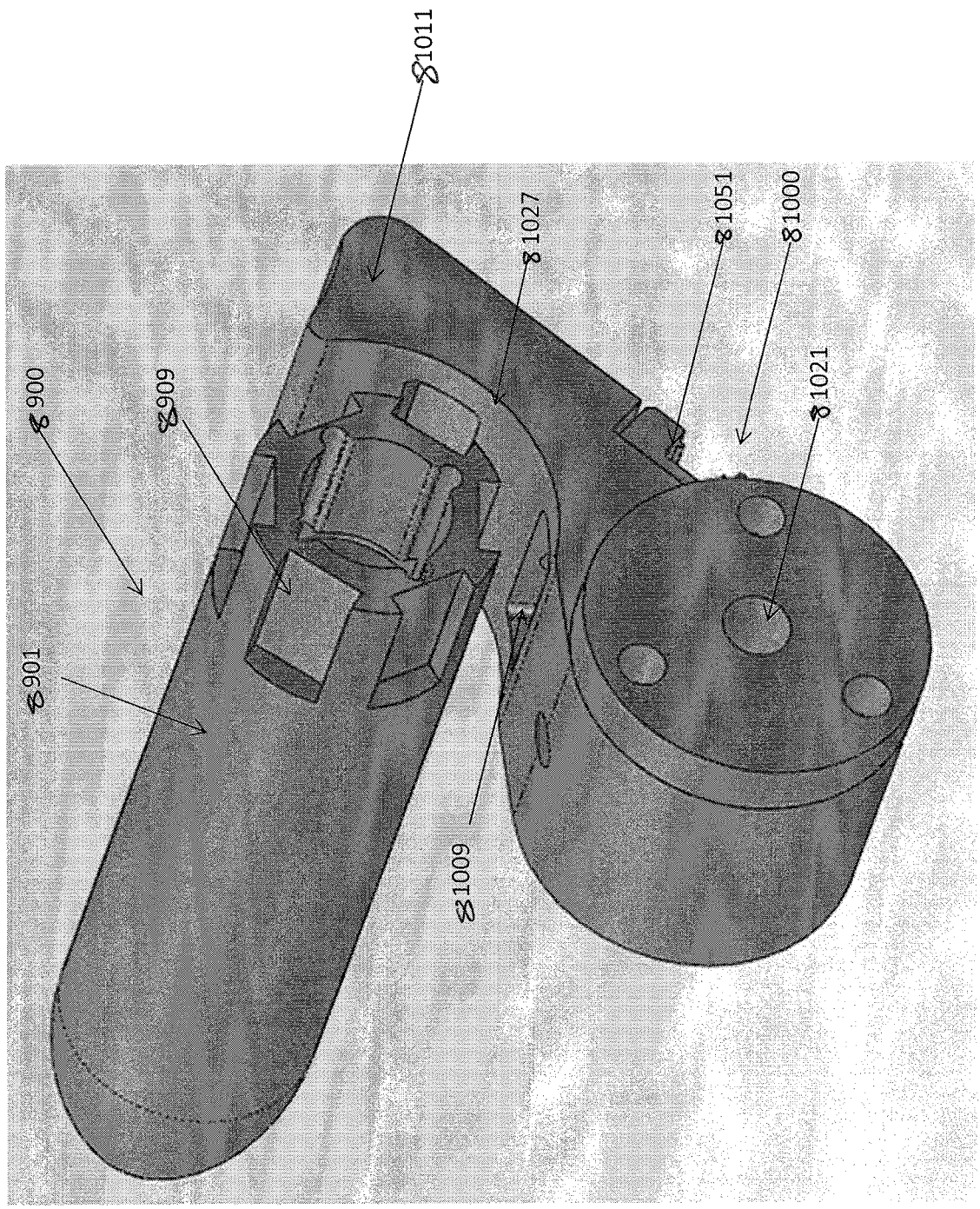
FIG. 30 shows a variation of a system for magnetic, non-contact translation of a shaft of a catheter.

FIG. 30 illustrates a variation of a non-contact system including a response element and a driver that can be used to impart translational linear motion into a component of a catheter. The response element 8900 can include a bearing 8901 configured to fixedly attach to an outer shaft or torque shaft of the catheter. The bearing 8901 can include a set of magnetic holders 8909, such as pockets in the bearing 8901, configured to hold magnets therein. In one embodiment, the bearing 8901 can be configured to only translate (not to rotate). As a result, the holders 8909 can include domains or magnets of the same polarity. The magnetic holders 8909 can extend around the circumference of the bearing 8901 such that the bearing 8901 can engaged with the driver 81000 regardless of the direction in which it is set down on the driver 81000.

The magnetic driver 81000 can be contained within a housing 81011 having a crevice or channel 81027 configured to hold the response element 8900, i.e., to allow the response element 8900 to rest therein. The channel 81027 can include magnetic holders 81009 therearound, such as a pocket in the driver 81000, configured to hold magnetic domains. The holders 81009 and/or magnetic domains in the holders can be configured to align with (but of opposite polarity to) the holders 8909 and domains of the response element 8900.

The magnetic driver 81000 can be configured to slide along a slide bearing plate via attachments 81051. The magnetic driver 81000 can further include a connector 81021 configured to connect to a motor for translating the driver 81000. For example, the connector 81021 can connect to a threaded rod attached to a rotary motor such that rotation of the motor imparts translation of the driver 81000.

The magnetic driver 81000 can be used to drive linear translational motion of the torque shaft attached to the response element 8900. To do so, the response element 8900 (connected to a torque shaft of the catheter) can be placed in the channel 81027. As the driver 81000 is moved linearly, the interaction between the magnetic domains on the driver 81000 and the magnetic domains on the response element 8900 will cause the response element 8900, and thus the attached torque shaft, to move linearly as well. As a result, the torque shaft can be driven forward (distally) or backwards (proximally). Such distal or proximal motion can be used, for example, to open a nosecone of an atherectomy device and/or pack tissue into the nosecone during an atherectomy procedure.

Although the response element 8900 and driver 81000 have been described as imparting linear motion to a torque shaft of a catheter, it could be used to impart linear motion to other shafts of a catheter, such as a drive shaft attached to a cutter.

Advantageously, the response element 8900 and driver 81000 can allow for non-contact linear actuation of a driveshaft of a catheter. As a result, the catheter can be actuated while maintaining a sterile field. For example, a sterile bag or sheet can be placed over the housing 81011 and/or such that it lines the channel 81027 to separate the sterile and non-sterile field. Because the catheter with the response element 8800 can simply be placed on top of the housing 81011 to actuate the driveshaft, the system provides easier sterility options than those where snapping or physical connection of the catheter and the driver are required.

In some embodiments, a drive system can be used to impart both linear and rotational motion into an element or multiple elements of a catheter. For example, a system can include a combination of response elements and drive elements on one or more shafts of the catheter. Referring to FIGS. 31A-34, a drive system 81300 can include a magnetic response element 81100*a* and a driver 81200*a* to impart rotational and linear translational motion to an outer torque shaft of a catheter and a response element 81100*b* and driver 81200*b* to impart rotational motion to a driveshaft of the catheter.

Figure 32:
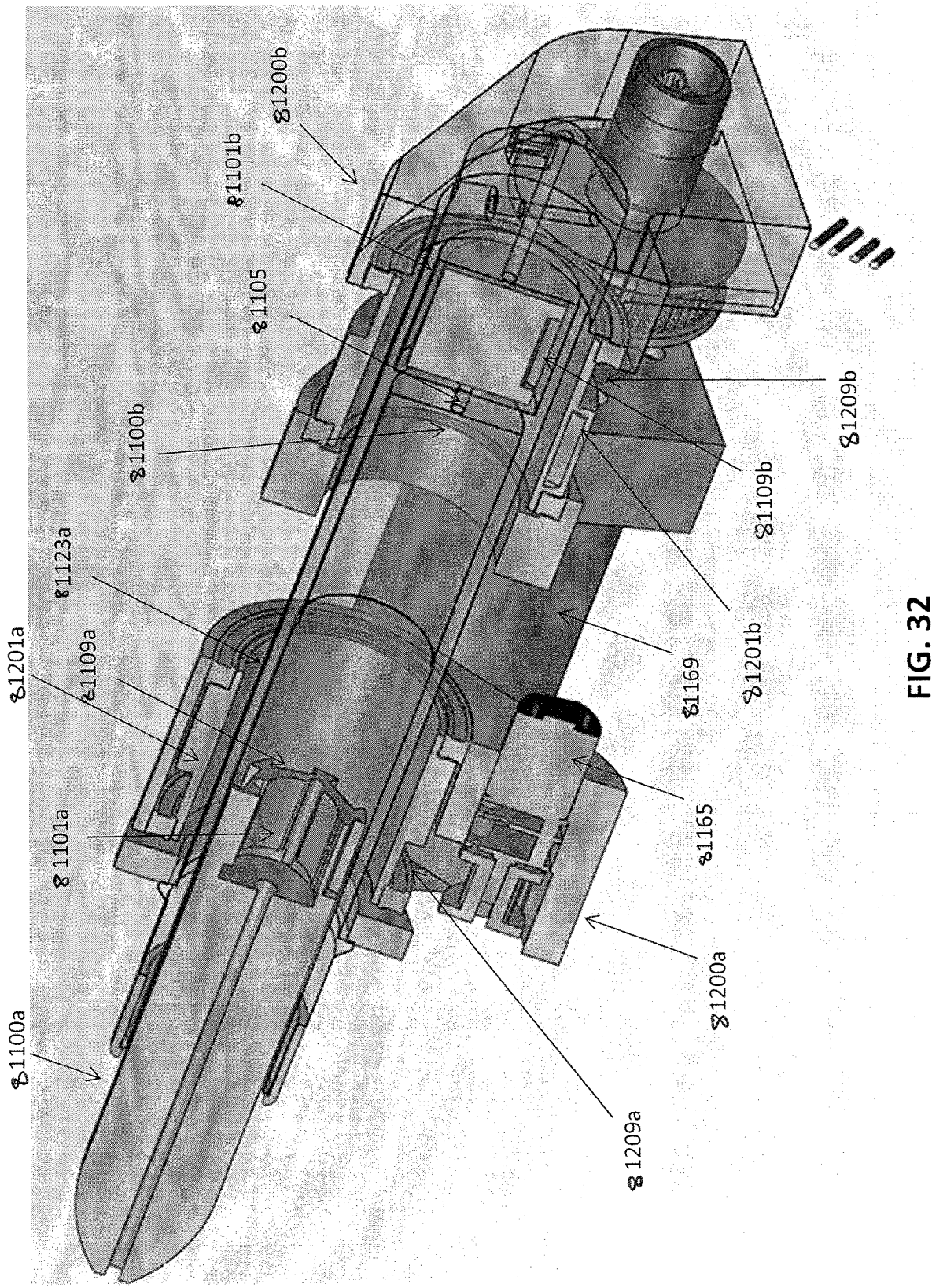
FIG. 32 is a horizontal cut away view of FIGS. 31A-31B.

Referring to FIG. 32, a first magnetic response element 81100*a*, similar to the response element 8900, can include a bearing 81101*a* configured to fixedly attach to a torque shaft of the catheter. The bearing 81101*a* can include a set of magnetic holders 81109*a*, such as pockets in the shaft 81101*a*, configured to hold magnets therein. The magnetic domains can be arranged in domains of opposite polarity, i.e. neighboring magnets around the circumference can have opposite polarities.

Figure 33:
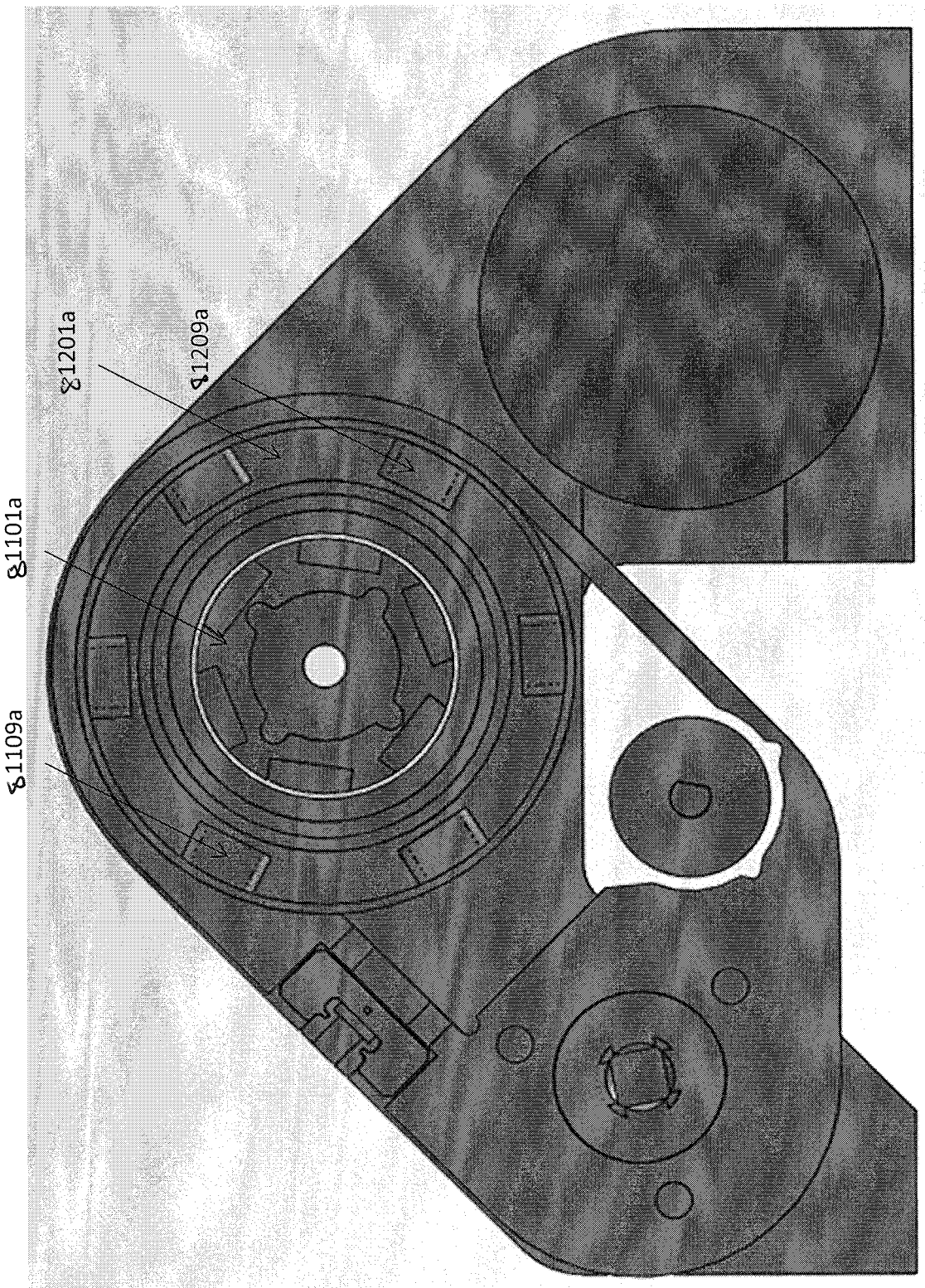
FIG. 33 shows a cross section of the distal response element and drive element of the system of FIGS. 31A-31B.
Figure 34:
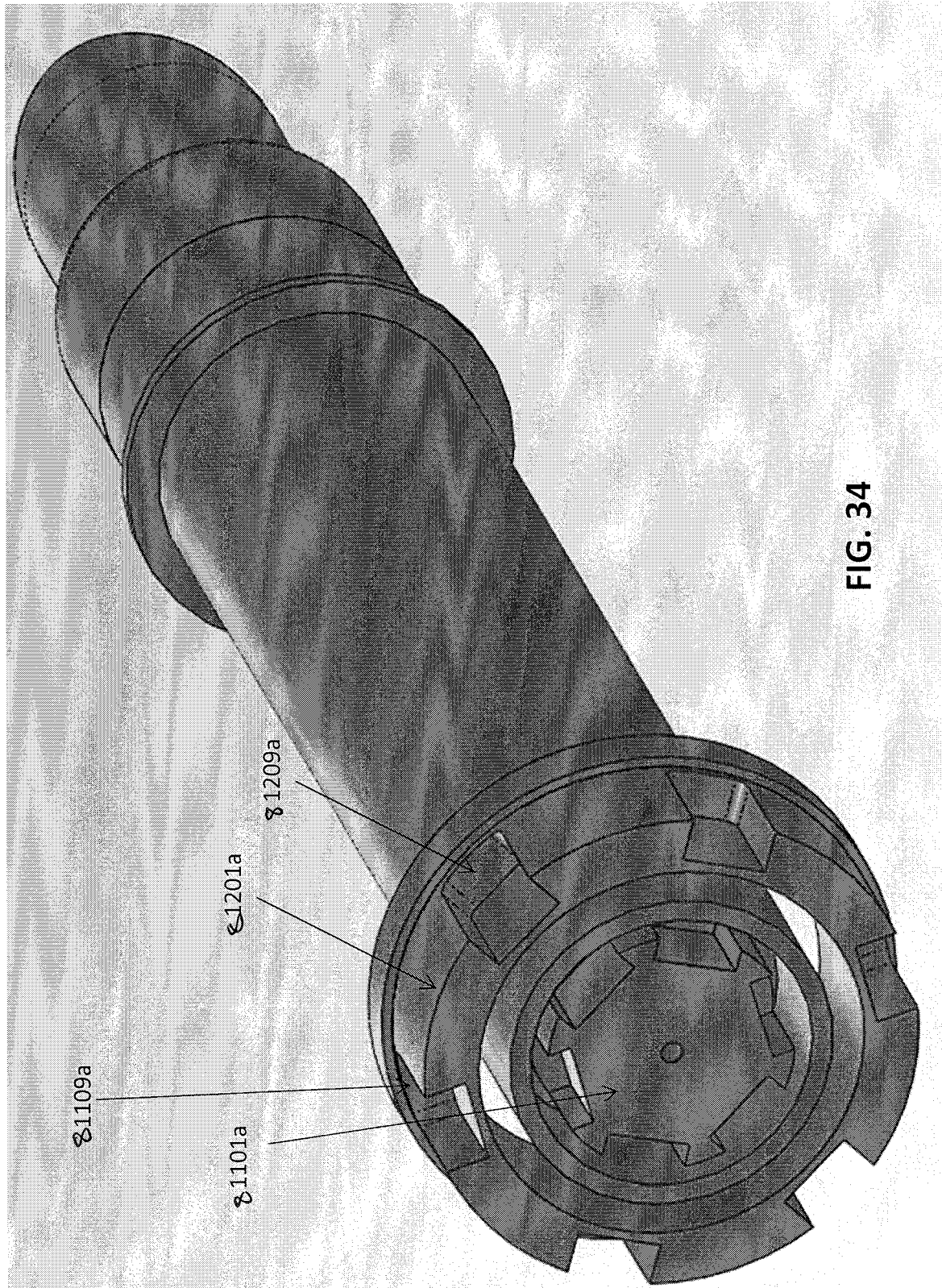
FIG. 34 shows distal response element and drive element of the system of FIGS. 31A-31B.

As seen best in FIGS. 33 and 34, the driver 81200*a* can include a rotor 81201*a* connected to a motor 81165 for translating the rotor 81201*a* as well as a motor 81167 to drive rotation of the rotor 81201*a*. The rotor 81201*a* can include magnetic holders 81209*a*, such as pockets in the rotor 81201*a*, configured to hold magnetic domains. The holders 81209*a* and/or the magnetic domains in the pockets can be configured so as to align with (but of opposite polarity to) the holders 81109*a* on the first magnetic response element 81100*a*. Similar to the driver 400 of FIGS. 25A-25B, the driver 81200*a* can be configured to actuate a shaft of a catheter having the response element 81101*a* by snapping the response element 81101*a* into a connector 81123 in a housing 8111 of the driver 81200*a* to align the rotor 81201*a* around the magnets of the response element 81101*a*.

Figure 31A:
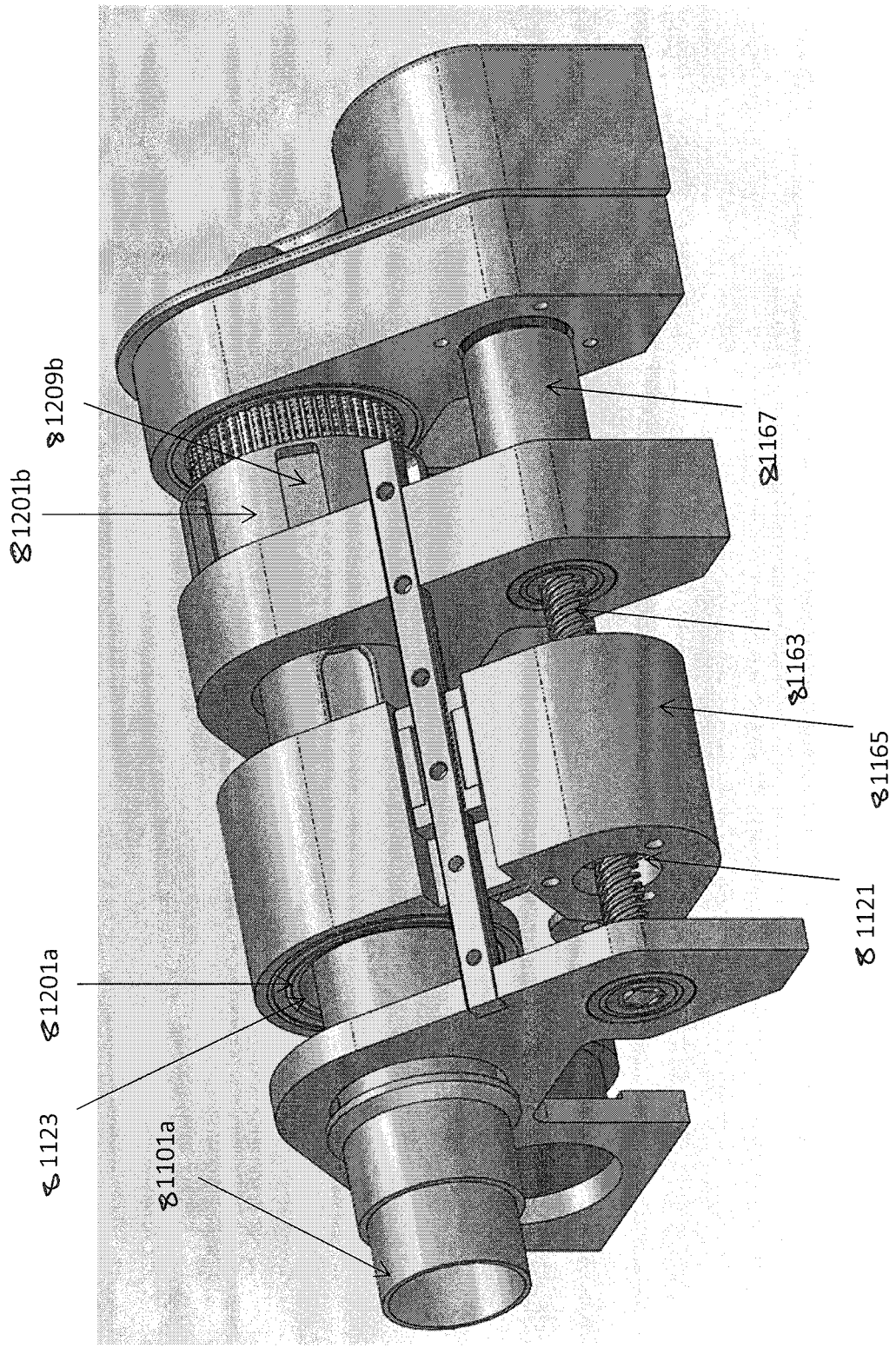
FIGS. 31A-31B show a variation of a system for magnetic, non-contact actuation of a catheter, including translation and rotation of a torque shaft and rotation of a driveshaft.
Figure 31B:
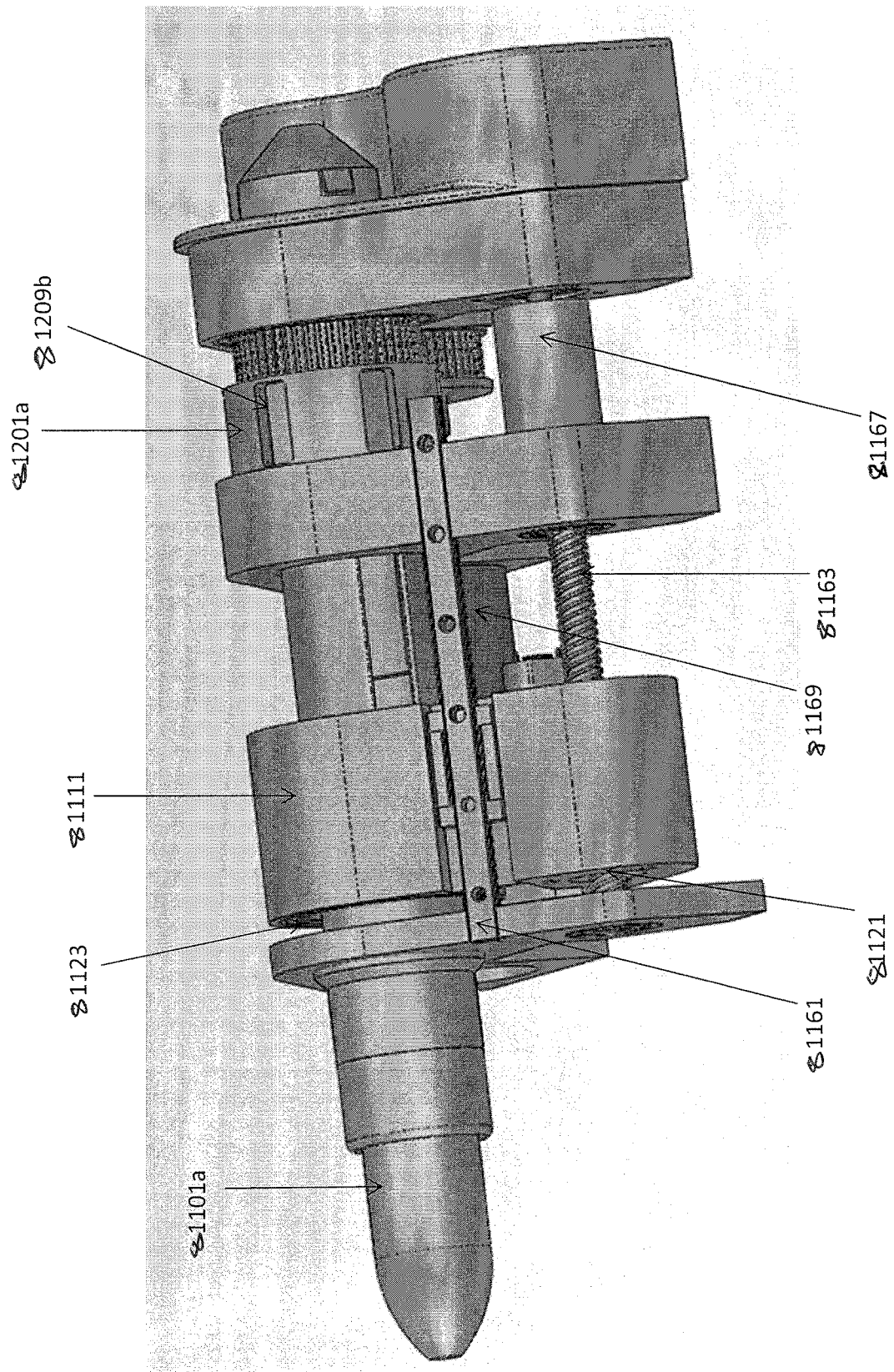

Rotation of the rotor 81201*a* (via motor 81167) will thus cause rotation of the response element 81101*a*, and thus the attached catheter shaft, such as a torque shaft, due to interaction between the magnets on the rotor 81201*a* and the response element 81101*a*. Further, translation of the rotor 81201 (via motor 81165 and a threaded rod 81163 extending through a connector 81121) will cause the response element, and thus the torque shaft, to translate linearly. As shown in FIGS. 31A and 31B, the sliding motion will thus cause the bearing 81101*a* of the response element 81100*a* to telescope in and out. In one embodiment, the driver can be used with an atherectomy catheter. Rotation of the driveshaft element can rotate the cutter and/or an imaging element of the atherectomy catheter. Rotation of the torque shaft of the atherectomy catheter can direct or orient the catheter and translation of the torque shaft relative to the drive shaft can deflect a distal end of the atherectomy catheter to expose the cutter.

Referring again to FIG. 32, a second response element 81100*b* can similarly include a bearing 81101*b* having magnetic domains 81109*b* therearound. The response element 81100*b* can include a 81105 therethrough for engagement with a driveshaft of a catheter. Further, a second drive element 81200*b* can include a rotor 81201*b* and magnetic holders 81209*b*. The response element 81100*b* can be configured to slide into the rotor 81201*b* such that the magnets of the response element 81100*b* and the rotor 81201*b* align. Accordingly, rotation of the rotor 81200*b* by the motor 81169 will cause the rotor 81201*b*, and thus the response element 81100*b* and attached driveshaft to rotate. In one embodiment, this rotation of the driveshaft can cause a distal cutter attached to the distal end of the driveshaft to rotate.

In some embodiments, the amount of possible "pull" force applied by the driver can be adjusted by the strengths of the magnets. The amount of force transmissible in both the rotational and translational motions can also be limited by the strength and arrangement of the magnets.

In some embodiments, a controller can be used to control the drivers described herein.

It is to be understood that the magnetic drive system described herein can be used with any of the catheters described herein and/or other catheter designs.

Figure 53A:
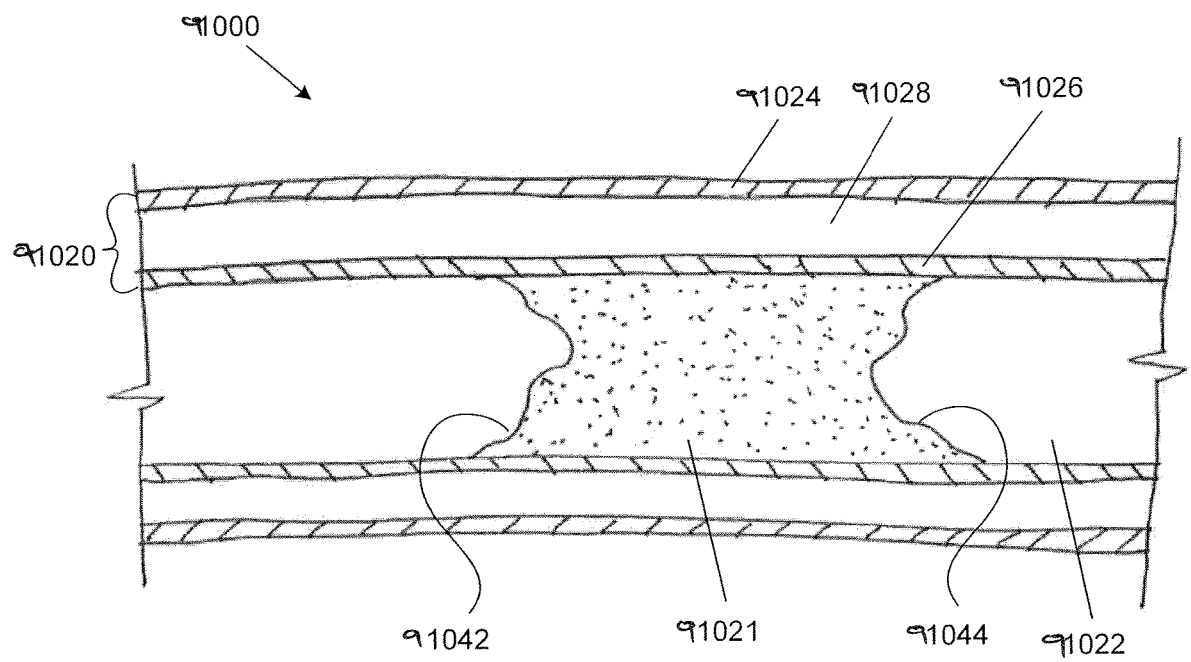
FIG. 53A shows an exemplary occluded vessel.
Figure 53B:
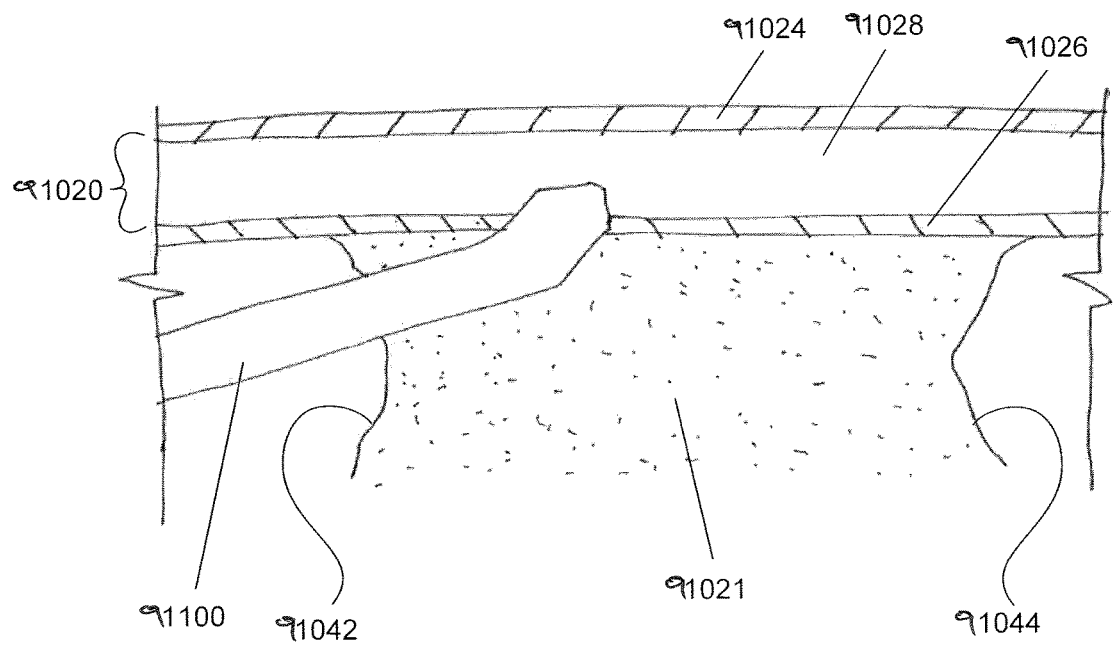
FIG. 53B shows an occlusion-crossing catheter that has extended into the subintimal layers of the occluded vessel of FIG. 53A.
Figure 53C:
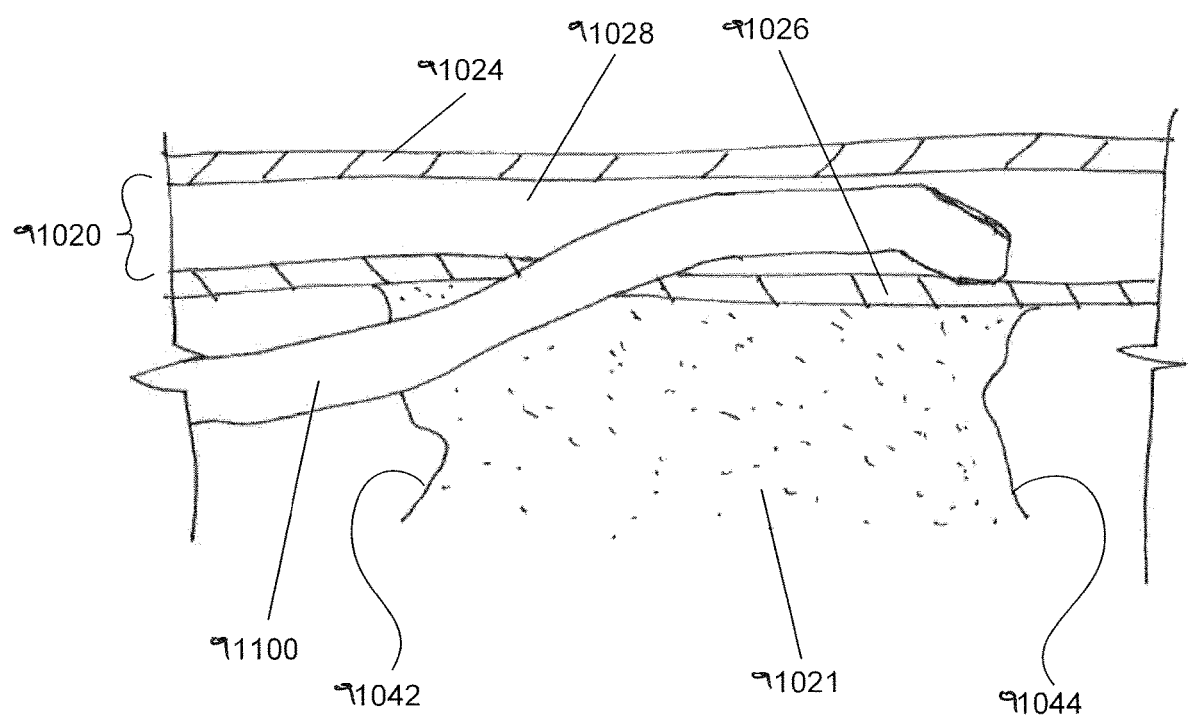
FIG. 53C shows an occlusion-crossing catheter that has been trapped in the subintimal space.

In some embodiments, the catheters described herein (and/or other catheters) can be used with a stylet, e.g., to assist in direction of the catheter into a true lumen. That is, referring to FIG. 53A, an occluded vessel 91000 includes a lumen 91022 (or "true lumen") with an occlusion 91021 and an arterial wall 91020. The arterial wall 91020 can include an innermost intimal layer 91026, which can include the endothelium, the subendothelial layer, and the internal elastic lamina. A relatively soft medial layer 91028 (also called the "subintimal space") surrounds the intimal layer 91026, which is then surrounded by an advential layer 91024. The proximal and distal caps 91042, 19044 of the occlusion are generally very hard relative to the rest of the occlusion. As a result, when a guidewire or occlusion-crossing device hits one of the caps 91042, 91044, it can often end up deflecting off of the cap 91042, 91044 and extending through the intimal layer 91026 and into the relatively soft medial layer 91028. For example, referring to FIG. 53B, an occlusion-crossing device 91100 has extended into the subintimal space within the medial layer 91028, which can define a "false lumen." As shown in FIG. 53C, the occlusion-crossing device 91100 can then get trapped in the subintimal space outside the true lumen 91022.

Stylets are described herein that can be used to assist in occlusion-crossing within a blocked vessel. For example, in some embodiments, the stylets described herein can redirect occlusion-crossing devices back into the true lumen of a vessel. In addition or alternatively, the stylets described herein can straighten and/or deflect an occlusion-crossing device to orient the device as needed.

In general, any of the stylets described herein can have a deflection region at the distal end thereof to provide directionality and steerability of the catheter. The deflection region can, for example, be imparted by a pre-shaped curve that matches an inner lumen of a catheter. The deflection region can also be imparted by an s-shaped curve at the distal tip of the stylet that helps orient and direct the stylet back into the true lumen of a vessel. In some embodiments, the deflection region can have a flattened profile to provide stability during piercing of the vessel wall into the true lumen.

Any of the stylets described herein can further be designed to include both flexible and stiff portions along the longitudinal axis to aid both in conforming the stylet to a catheter in which it is inserted and in providing the necessary stiffness to puncture a vessel wall. The stylets can include a proximal portion, a middle flexible portion, and a distal stiff portion. The middle flexible portion can be flexible enough to conform to a curve of a catheter in which the stylet is inserted while the distal stiff section can be stiff enough to provide a piercing force to guide the stylet into a true lumen of a vessel.

The stylets described herein can include an inner flexible body and an outer stiff tube. The flexible body and outer stiff tube can be moved axially relative to one another to provide the desired stiffness or flexibility for the stylet, e.g., to provide flexibility to extend around a pre-set curve in a catheter or to provide stiffness to straighten the pre-set curve. In other embodiments, the inner body can be stiff while the outer tube can be flexible.

Furthermore, the stylets described herein can include a coiled member attached to the distal tip to provide protection for the tip when in the extended configuration and allow for exposure of the tip when compressed.

Referring to FIGS. 43A through 44C, an exemplary directional re-entry stylet 9100 includes a proximal portion 9101, a middle curved portion 9102, and a distal pointed end 9103.

The proximal portion 9101 can be a wire, such as a stainless steel wire. The wire can be chosen to have a stiffness that corresponds to the required amount of pushability and column support needed for the particular wire diameter used. The proximal portion 9101 can further have a substantially round cross-section. The proximal portion 9101 can be approximately 0.010 to 0.035 inches in diameter, such as approximately 0.015 inches in diameter.

The curved middle portion 9102 can have a pre-set curve 9105 that is flexible enough to follow the contours of lumen of a catheter but stiff enough to orient its curved shape to align with a bent section of an the catheter. For example, referring to FIG. 44B, the pre-set curve 9105 can form an angle a of between 120 degrees and 180 degrees, such as between about 130 degrees and 170 degrees, for example approximately 150 degrees. The pre-set curve can advantageously ensure that the stylet 9100 aligns properly with the catheter in which it is inserted, thereby allowing the catheter to maintain its curved form and ensuring proper steering of the catheter.

Further, in other embodiments, the pre-set curve 9105 can be stiff enough to change the deflection region of the catheter in which it is inserted. Thus, for example, the pre-set curve 105 could force the catheter into a set angle of between 120 degrees and 180 degrees, such as between about 130 degrees and 170 degrees, such as 150 degrees. In some embodiments, rather than having a pre-set curve, the curved middle portion 9102 can have a flexible portion, such as a necked section or a coiled section, to allow the middle portion 9102 to flexibly conform to the shape of a catheter in which it is inserted.

The curved middle portion 9102 can be formed of a wire, such as a nitinol wire. The curved middle portion can further have a substantially round cross-section. The curved middle portion 9102 can have a diameter of approximately 0.008 inches to 0.015 inches, such as approximately 0.012 inches in diameter. In some embodiments, the middle portion 9102 is formed separately from the proximal portion 9101 and connected through a junction 9106, such as a hypotube joint (see FIG. 44C) or a laser welded sleeve. In other embodiments, the middle portion 9102 and proximal portion 9101 can be formed of a single piece of material, such as a single wire.

The pointed distal end 9103 can include an s-shaped curve 9107 (see FIGS. 43B and 44B), i.e., include two opposing curves 9109 and 9111 along the longitudinal axis. Referring to FIG. 44B, the proximal-most curve 9109 of the s-shaped curve 9107 can have an angle β of between approximately 90° to 180°, such as between about 120° to 160°, such as 150°, while the distal-most curve 9111 of the s-shaped curved 9107 can have an angle θ of between approximately 90° to 180°, such as 120° to 160°, such as 150°. The s-curve 9107 can be oriented such that the distal end 9103 points in approximately the same direction as the end of the catheter, as set by the pre-set curve 9105. That is, referring to FIG. 44B, the angle α can be oriented in approximately the same direction as the angle θ while the angle β can be aligned in substantially the opposite direction. Angles β and θ can be approximately equal to one another. Further, having the distal end 9103 point in the same direction as the distal end of the catheter (set by the jog in the catheter) advantageously provides more of an angle for re-entry into a true lumen. Finally, the alignment of the angle α with the angle θ also advantageously provides an indication as to the orientation of the stylet.

The distal tip 9115 (between the distal-most point and the distal curve 9111) can be less than about 3 mm, such as between about 1-2 mm. Further, the stylet 9100 itself can be about 150 cm-300 cm in length, such as 175 cm to 200 cm, such as approximately 180 cm in length. Thus, the distal tip 9115 can comprises less than 1%, such as less than 0.5% of the total length of the stylet 9100. The short length of the distal tip 9115 relative to the length of the entire stylet 9100 advantageously provides that the stylet will advance only partially through the vessel wall and back into the true lumen during reentry (i.e., to avoid puncturing the opposite wall of the vessel).

In other embodiments, rather than having an s-shaped curve 9107, the pointed distal end 9103 can include a J-shaped curve, i.e. a hook, that can be used to force the stylet 9100 (and thus the catheter in which it is inserted) back towards a true lumen.

The pointed distal end 9103 can further included a flattened portion, i.e., a portion in which the otherwise round cross-section has been flattened to include two substantially parallel and flat surfaces, e.g., such that a cross-section of the flattened portion is substantially oblong. As shown in FIG.

43B, the s-curve 9107 can be located within the flattened portion such that the shape of the "s" is formed on the flattened surface. This flattened portion can advantageously help to hold the pre-set curve as it is forced against tissue. The flattened portion can also advantageously provide rigidity as the tip of the stylet is forced into tissue.

Further, the pointed distal end 9103 can be tapered from the proximal end to the distal end. For example, the distal end can be 0.012 inches in diameter and can taper down to a tip 9115 of approximately 0.005 inches in diameter. The tip 9115 of the pointed distal end 9103 can be sharp, i.e., can be configured to penetrate tissue, such as subintimal layers of a blood vessel. The taper can advantageously provide smooth dilation or entry into a vessel wall or occlusion.

Figure 54A:
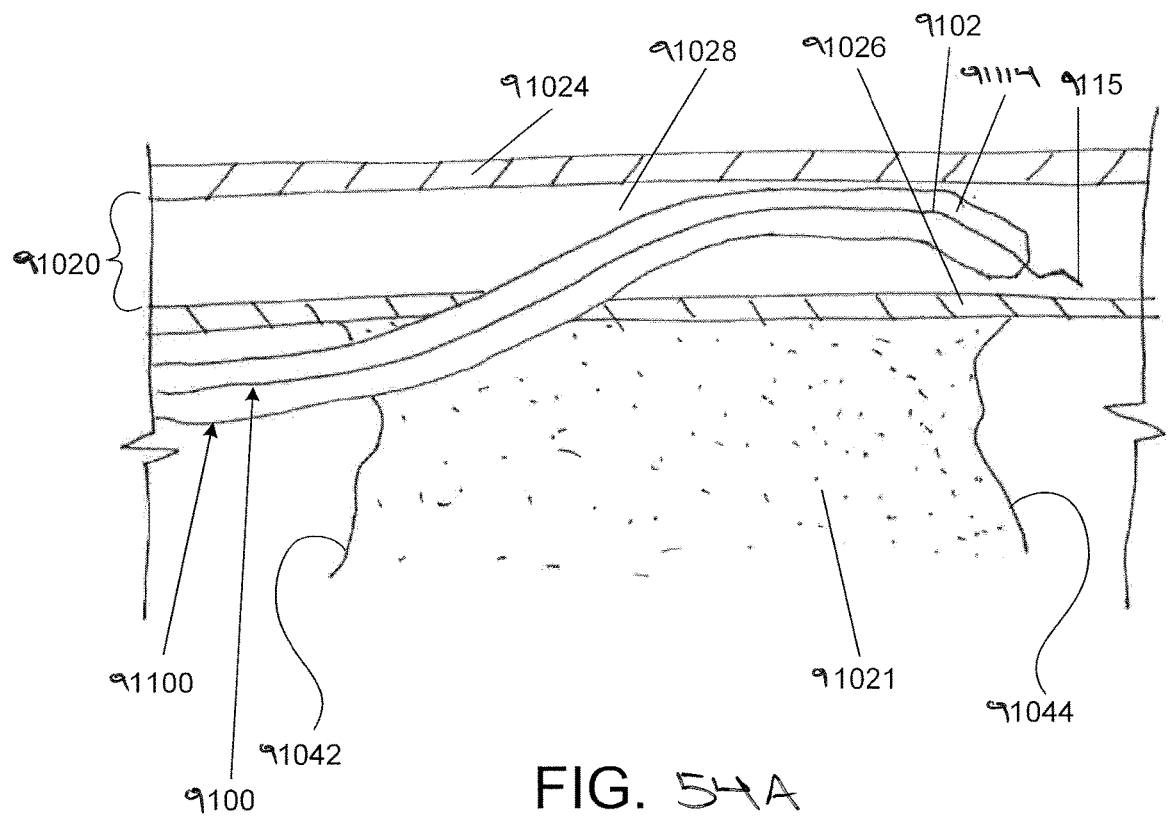
FIGS. 54A-54D show use of a stylet similar to the stylet of FIG. 43A to guide a catheter from the subintimal layer back into the true lumen.
Figure 54B:
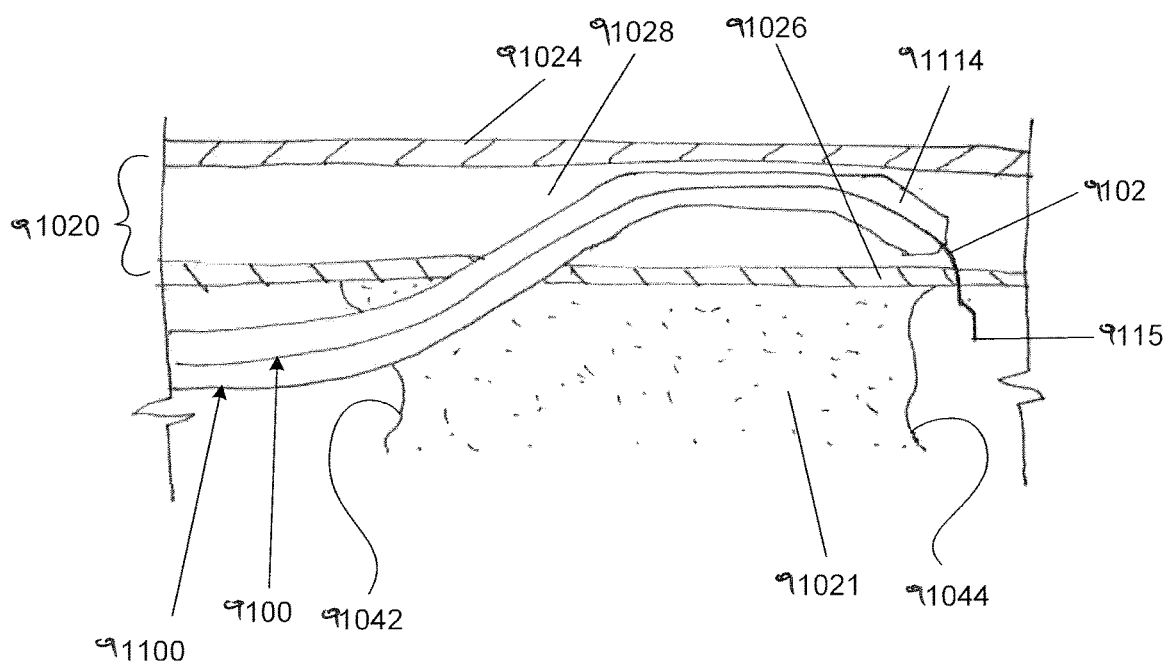
Figure 54C:
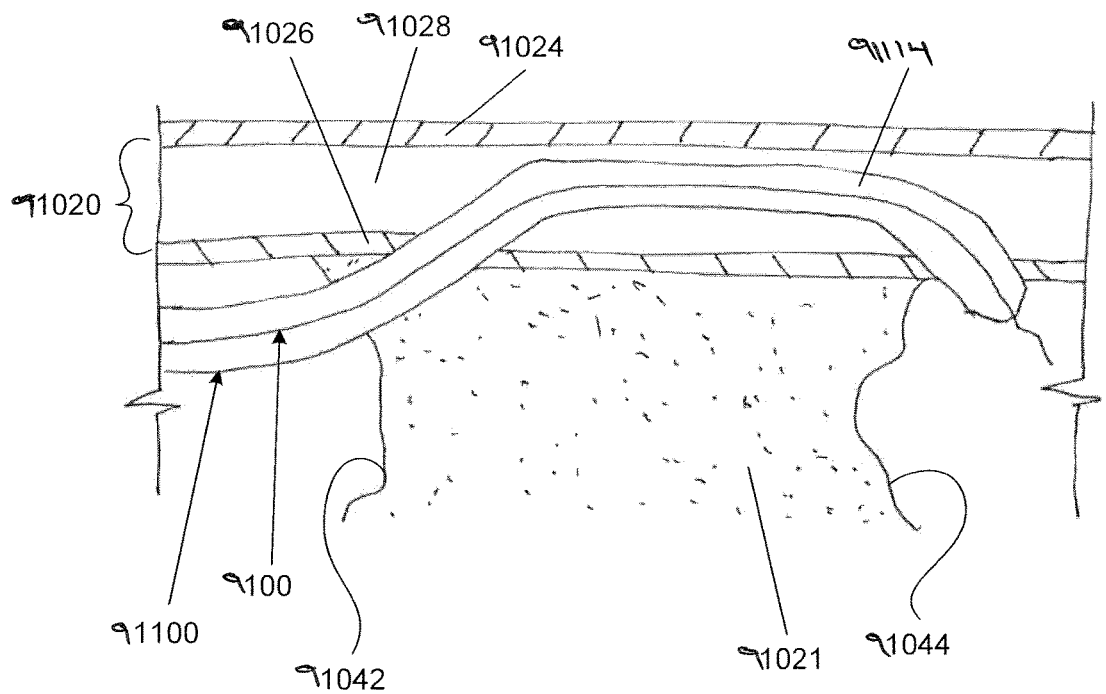
Figure 54D:
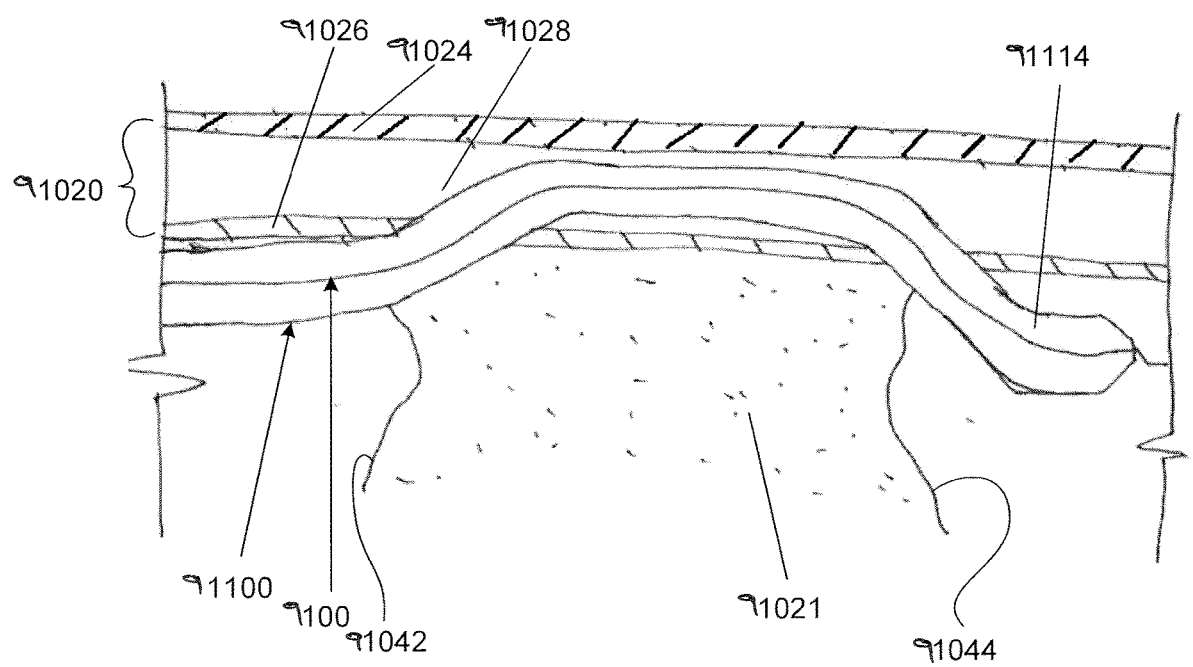

Referring to FIGS. 54A-54D, in one embodiment, a stylet 9100 can be used as a re-entry tool for an occlusion-crossing catheter 91100 that has exited the true lumen 91022 and entered the subintimal layer (e.g., medial layer 91028). The stylet 9100 can be placed through a guidewire channel of a catheter 91100. The catheter 91100 can have a fixed bend 91114, which can be rotated to point towards the true lumen 91022. As shown in FIG. 54A, the stylet 9100 can be threaded through the catheter 91100 such that the curved middle portion 9102 aligns with the bend 91114 in the catheter 91100 and such that the tip 9115 points out the distal end of the catheter. Because the angle of the curved middle portion 9102 is pointed in the same direction as the distal-most curve of the s-shaped curve, and because the fixed bend 91114 has been oriented towards the true lumen 91022, the distal tip 9115 will also point towards the true lumen 91022. Further, referring to FIG. 54B, because the curved middle portion 9102 has a pre-set curve, the curve will hold the stylet's orientation as it is advanced. Thus, as the stylet is advanced, the distal tip 9115 will curve even more sharply towards the true lumen 91022 and pierce back through the tissue of the vessel wall 91020 at a steep angle (e.g. at an angle of between approximately 60 and 90 degrees relative to the wall). Referring to FIG. 54C, the catheter 91100 can then be advanced over the stylet 9100 back into the true lumen 91022. As shown in FIG. 54D, to reorient the catheter 91100 towards down the axis of the lumen 91022, the catheter can be rotated approximately 180 degrees to point the fixed bend 91114 down the lumen 91022. In some embodiments, this process can be used to pass entirely by an occlusion (as shown in FIGS. 54A-54D). In other embodiments, the stylet 9100 can direct the catheter 91100 back into the occlusion at a point between the proximal 91042 and distal 91044 caps of the occlusion 91021, and then the catheter 91100 can be used to finish crossing through the lesion, such as will a rotating drill feature on the distal end of the catheter.

Referring to FIGS. 45A-45B, an aligning re-entry stylet 9200 includes a proximal portion 9201, a middle flexible portion 9202, and a distal stiff portion 9203.

The proximal portion 9201 can be a wire, such as a stainless steel wire. The wire can be stiff enough to provide pushability through a catheter. The proximal portion 9201 can be approximately 0.010 to 0.038 inches in diameter, such as approximately 0.015 inches in diameter.

The middle flexible portion 9202 is configured to be flexible so as to conform to the shape of a catheter in which it is inserted. In one embodiment, the flexible portion 9202 is a coil, such as a coil of wire. The coil can have an outer diameter of 0.010 to 0.038 inches, such as approximately 0.014 inches and an inner diameter of 0.005 to 0.010 inches, such as approximately 0.008 inches. The coil can be made, for example, of stainless steel. The wire forming the coil can have a diameter of 0.001 to 0.005 inches, such as approximately 0.003 inches. In another embodiment, the middle flexible portion 9202 could be a necked portion in a wire. In another embodiment, the middle flexible portion 9202 can be a separate flexible material, such as a plastic. In another embodiment, the middle flexible portion 9202 can be a hypotube that has been cut, such as laser cut, into a flexible spiral or plurality of rings along a spine.

The proximal stiff portion 9203 can be stiff enough to straighten a prebent catheter in which it is inserted. For example, the proximal stiff portion can be made of a stainless steel wire. The wire can have a diameter, for example, of 0.010 to 0.038 inches, such as approximately 0.015 inches. The distal portion 9203 can further include a sharp tip 9212, such as a needle-like or pointed end. In some embodiments, the sharp tip 9212 can be angled to assist in re-entry.

Figure 46A:
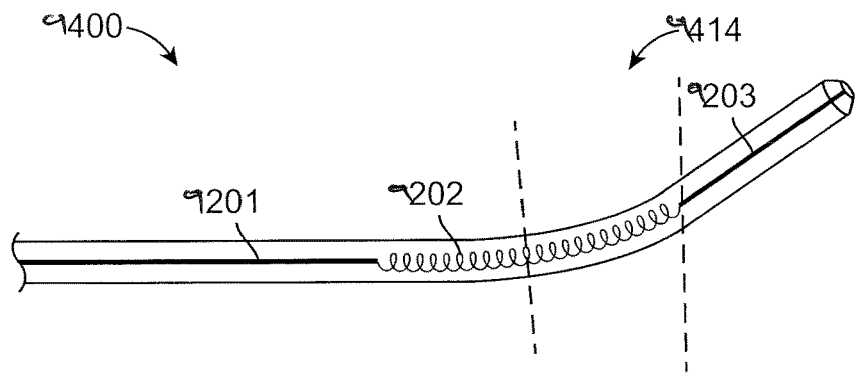
FIGS. 46A-46C show the re-entry stylet of FIG. 45A in an exemplary CTO crossing device with a pre-set curve.
Figure 46B:
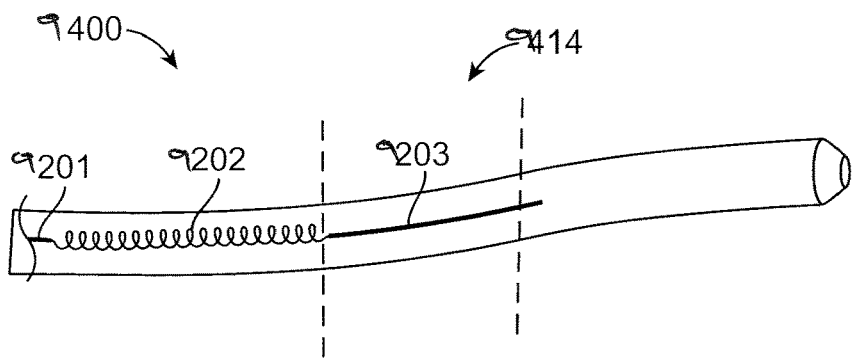
Figure 46C:
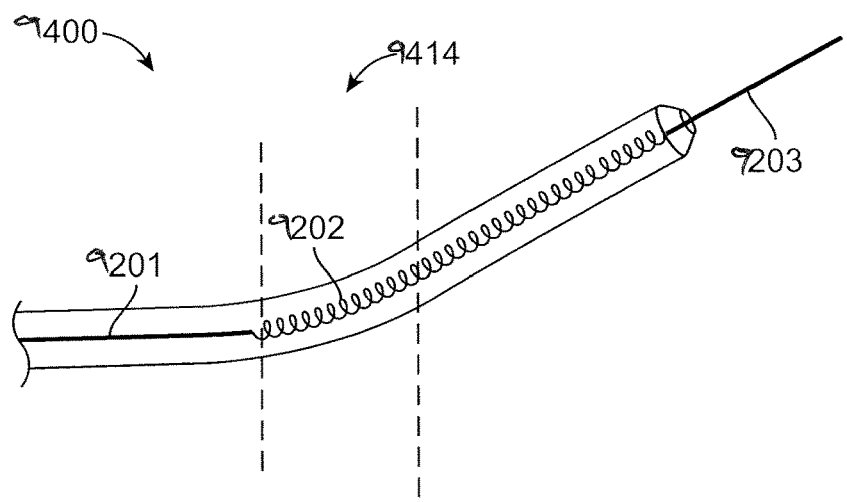

The flexible portion 9202 can have a length such that the flexible portion can align with a pre-set curve 9414 in a catheter 9400 in which it is inserted both while the distal stiff portion 9203 remains inside the catheter 9400 (FIG. 46A) and while the distal stiff portion 9203 extends distally from the distal end of the catheter 9400 (FIG. 46C).

In use, referring to FIGS. 46A-46C, the stylet 9200 can be inserted into a catheter, such as a catheter 9400 having a pre-bent curve 9414. As shown in FIG. 46A, the stylet 9200 can be inserted such that the flexible portion 9202 aligns with the pre-bent curve 9414 while the distal portion 9203 remains inside the catheter. This alignment can advantageously provide little interference with the catheter as the catheter is used under normal conditions.

The stylet 9200 can also be inserted such that the distal stiff portion 9203 aligns with the pre-bent curve 9414, thereby straightening the curve, as shown in FIG. 46B. This alignment can advantageously make directly entry into an occlusion easier, i.e., placing force on a straightened catheter, from within the true lumen, can provide a straight trajectory into the occlusion.

Figure 55A:
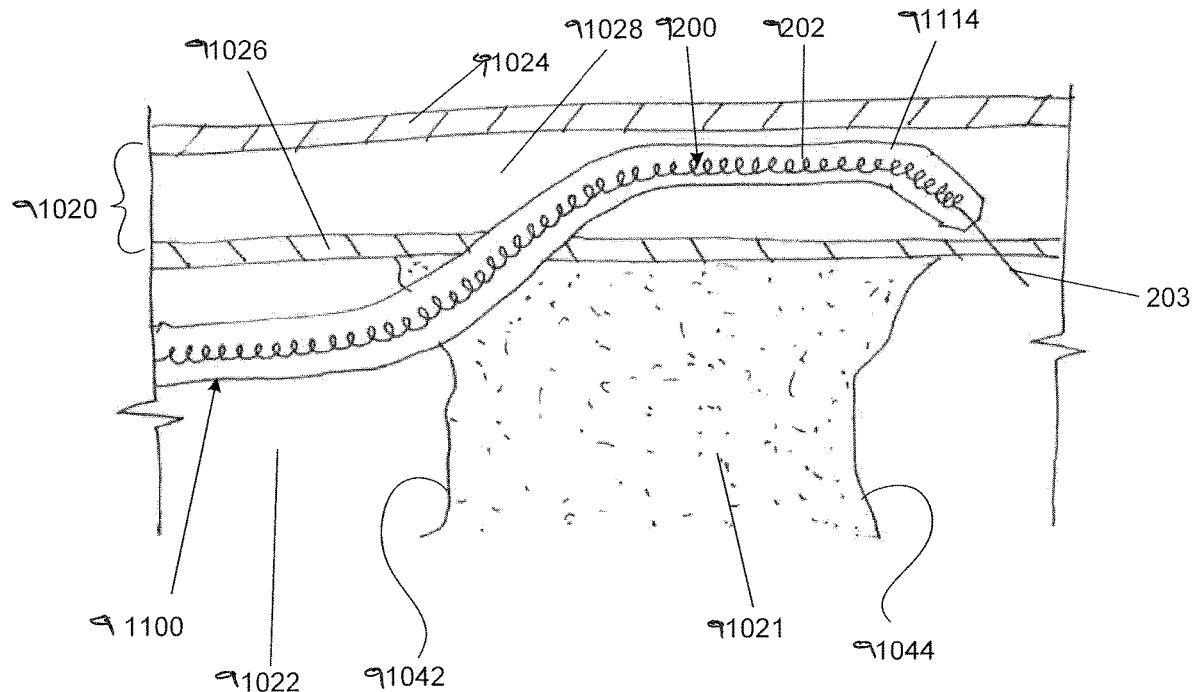
FIGS. 55A-55C show use of a stylet similar to the stylet of FIG. 4A to guide a catheter from the subintimal layer back into the true lumen.
Figure 55B:
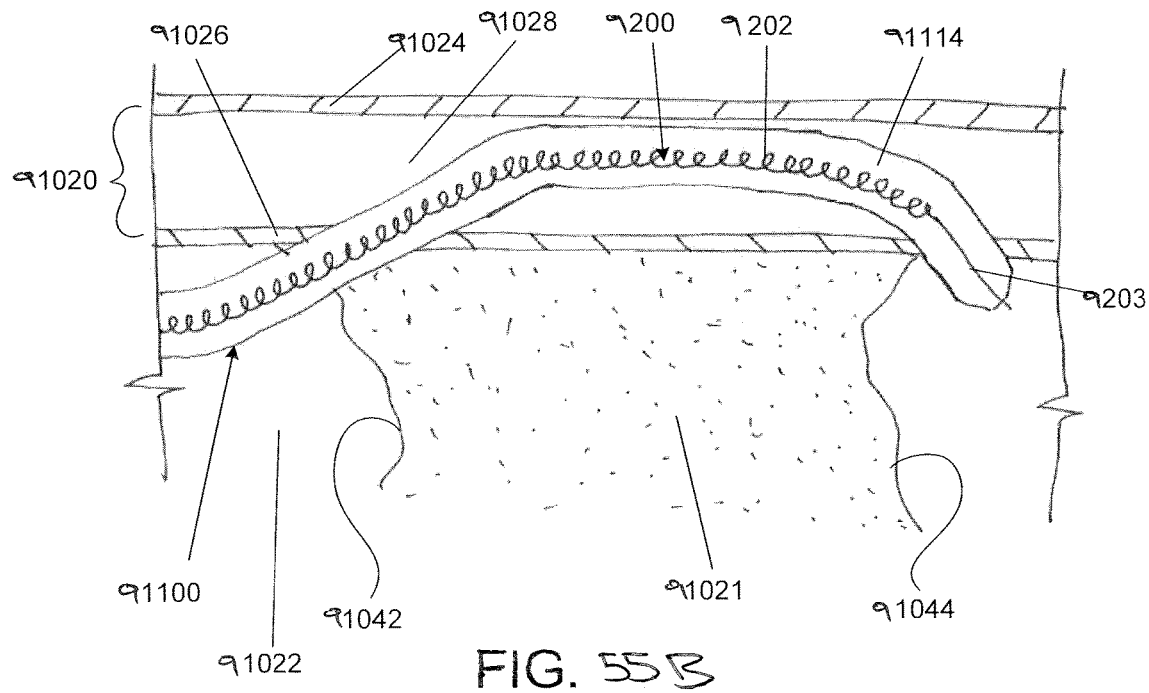
Figure 55C:
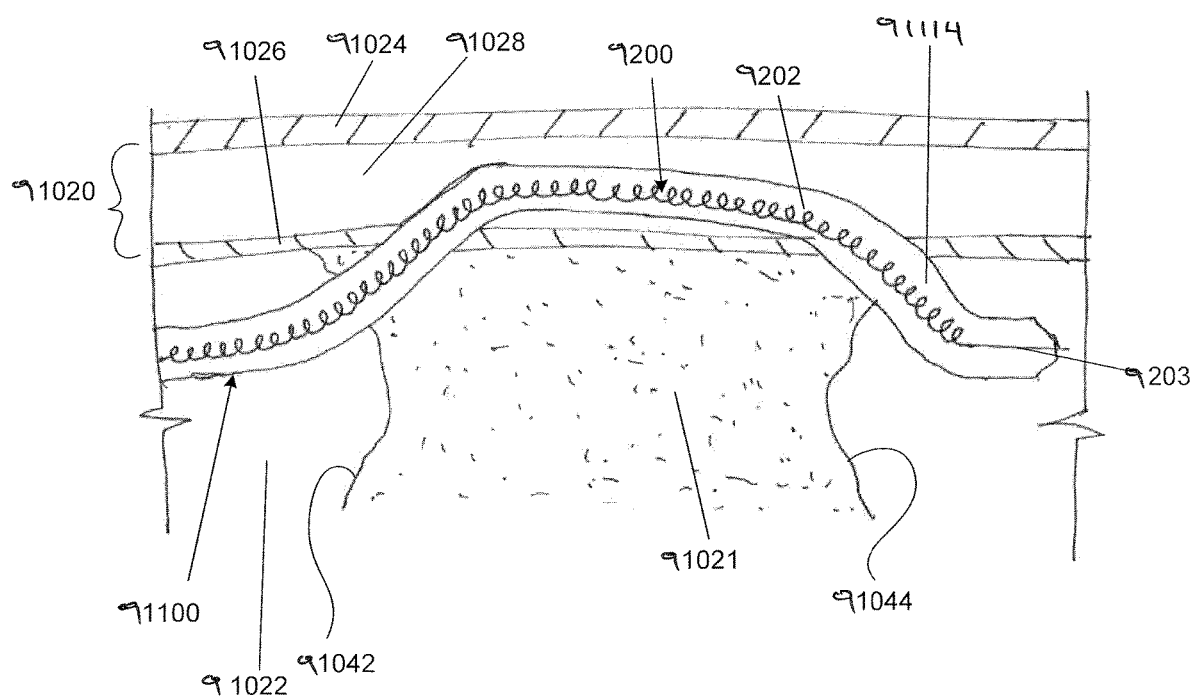

Finally, as shown in FIG. 46C, the stylet 9200 can be inserted such that the flexible portion 9202 aligns with the pre-bent curve 9414 while the distal portion 9203 extends out of the distal end of the catheter 9400. This alignment can advantageously assist in re-entry from a false lumen to a true lumen, i.e., the curve of the catheter 9400 can be turned towards the true lumen, and the distal end 9203 of the stylet 9200 can be used to pierce the vessel and guide the catheter 9400 back into the true lumen. For example, FIGS. 55A-55C show a stylet 9200 used as a re-entry tool for an occlusion-crossing catheter 91100 that has exited the true lumen 91022 and entered the subintimal layer (e.g., medial layer 91028). The stylet 9200 can be placed through a guidewire channel of the catheter 91100. The catheter 91100 can have a fixed bend 91114, which can be rotated to point towards the true lumen 91022. As shown in FIG. 55A, the stylet 9200 can be threaded through the catheter 91100 such that the flexible portion 9202 aligns with the fixed bend 91114 while the distal portion extends out of the distal end of the catheter 91100. Because the fixed bend 91114 has been oriented towards true lumen 91022, the sharp distal portion 9203 will also point towards the true lumen 91022, making it easy to pierce the wall 91020. Referring to FIG. 55B, the catheter 91100 can then be advanced over the stylet 9200 back into the true lumen 91022. As shown in FIG. 54C, to reorient the catheter 91100 towards down the axis of the lumen 91022, the catheter can be rotated approximately 180 degrees to point the fixed bend 91114 down the lumen 91022. In some embodiments, this process can be used to pass entirely by an occlusion (as shown in FIGS. 55A-55C). In other embodiments, the stylet 9200 can direct the catheter 91100 back into the occlusion at a point between the proximal 91042 and distal 91044 caps, and then the catheter 91100 can be used to finish crossing through the lesion, such as with drilling features on the catheter 91100.

Figure 47A:
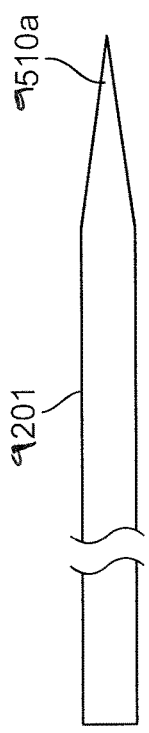
FIGS. 47A-47C show an exemplary process for producing the stylet of FIG. 45A.
Figure 47B:
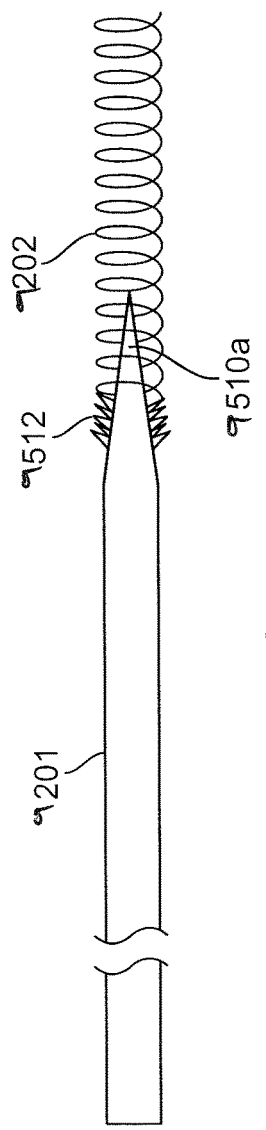
Figure 47C:
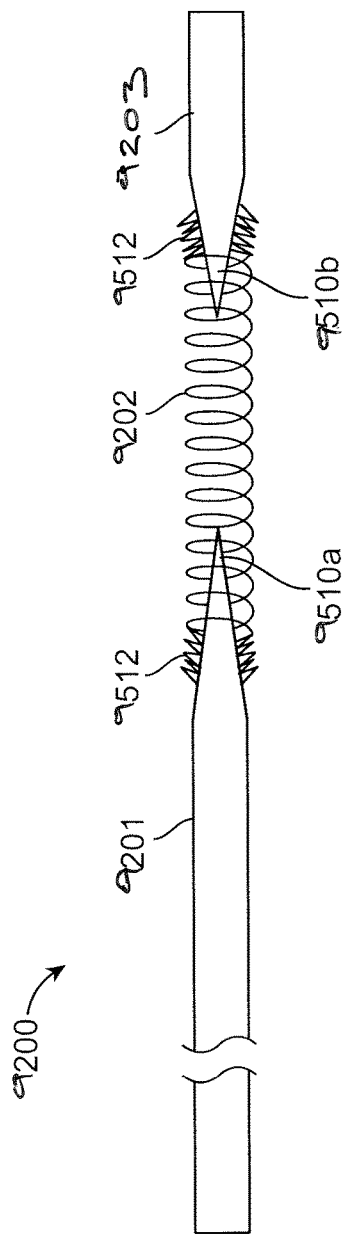

Referring to FIGS. 47A-47C, a stylet 9200 can be made, for example, by grinding two mandrels to a taper 9510a,b (the mandrels will form the proximal and distal ends, respectively), and then placing the tapers 9510a,b inside a coil 9202 and connecting the coil 9202 to each taper 9510a,b, as shown in FIG. 47C.

Figure 48:
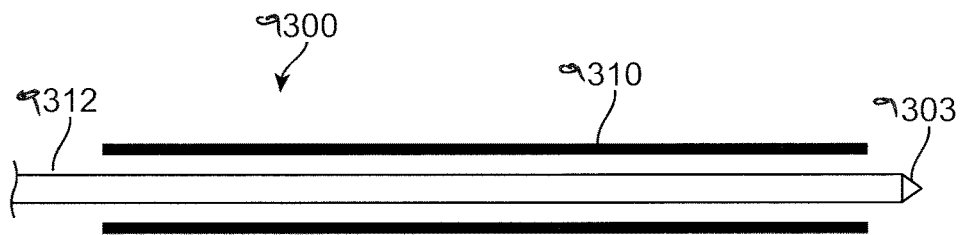
FIG. 48 shows an exemplary bilayer re-entry stylet having a stiff outer tube and a flexible inner elongate body.

Referring to FIG. 48, a stylet 9300 can include an outer tube 9310 and an inner elongate body 9312 axially movable relative to the outer tube 9310. The outer tube 9310 can be stiff relative to the inner elongate body 9312. The inner elongate body 9312 can have a pointed or sharp distal end 9303 similar to the distal end of the stylets 9100, 9200. The inner elongate body 9312 and/or the outer tube 9310 can be made of a metal, such as stainless steel or nitinol.

Figure 49A:
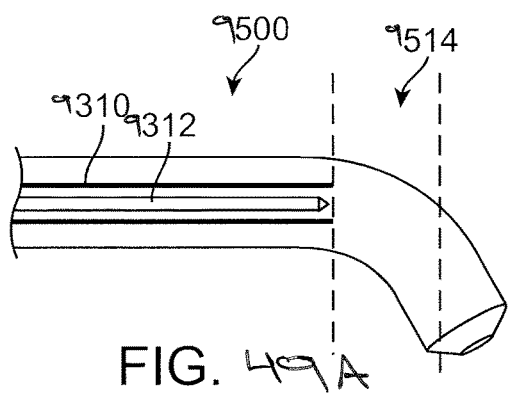
FIGS. 49A-49D shows the bilayer re-entry stylet of FIG. 48 in an exemplary CTO crossing device with a pre-set curve.
Figure 49B:
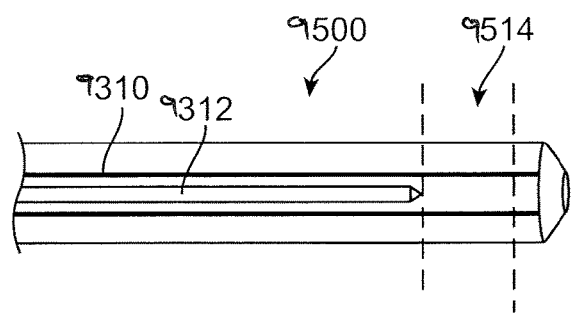
Figure 49C:
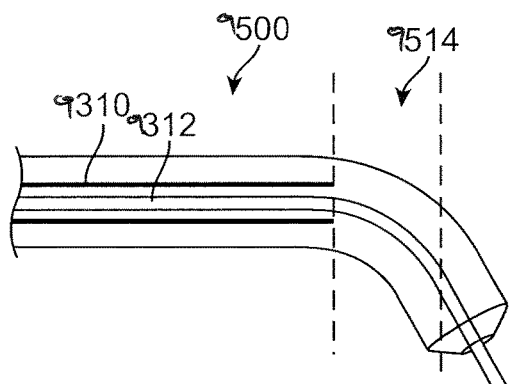

Further, referring to FIGS. 49A-49B, the stylet 9300 can be configured to be placed within a lumen of a catheter, such as a catheter 9500 having a pre-set curve 9514. The outer tube 310 can be stiff relative to the pre-set curve 9514 while the inner elongate body 9312 can be flexible relative to the pre-set curve 9514. As a result, the outer tube 310 can be used to straighten the pre-set curve 9514 while the inner elongate body 9312 can conform to the pre-set curve 9514.

Figure 49D:
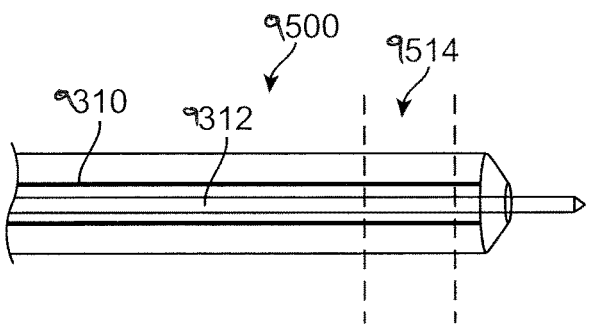

Thus, referring to FIG. 49A, the stylet 9300 can be placed such that the entire stylet 9300 is proximal to the pre-set curve 9514. As shown in FIG. 49B, if the outer tube 9310 is advanced distal to the pre-set curve 9514, then the pre-set curve 9514 of the catheter 9500 will substantially straighten out. Such straightening can be advantageous, for example, if the catheter 9500 is being used to cross a CTO from within the true lumen, as force can be applied on the CTO from substantially perpendicular to the CTO. Referring to FIG. 49D, the inner elongate body 9312 can also be extended out of the distal end of the catheter while the catheter is in a straightened position to assist with crossing the CTO (e.g. such that the pointed distal end 9303 can cut through the occlusion or pierce the proximal or distal cap). On the other hand, as shown in FIG. 46C, if only the inner elongate body 9312 is advanced distal to the pre-set curve 9514, then the pre-set curve 9514 can maintain its shape while the pointed distal end 9303 can be advanced out of the catheter 9500. This configuration can be advantageous, for example, for re-entry form a false lumen to a true lumen, i.e. the curve 9514 of the catheter 9514 can be turned towards the true lumen, and the pointed distal end 9303 of the inner elongate body 9312 can be used to pierce the vessel and guide the catheter 9500 back into the true lumen.

Figure 56A:
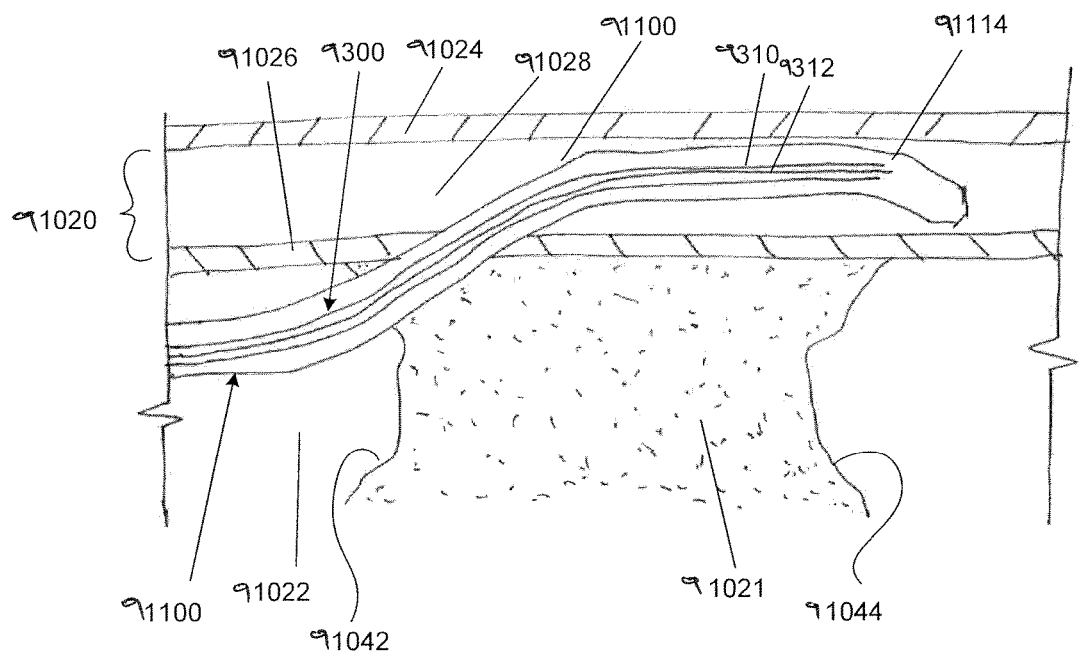
FIGS. 56A-56D shows use of a stylet similar to the stylet of FIG. 48 to guide a catheter from the subintimal layer back into the true lumen.
Figure 56B:
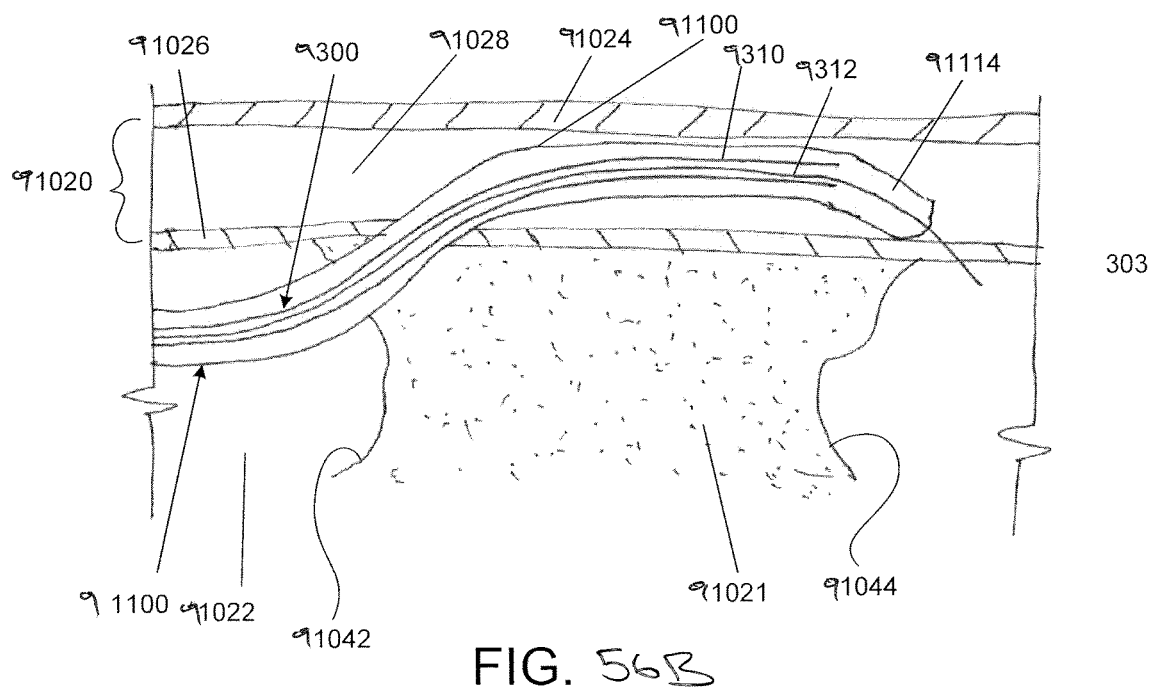
Figure 56C:
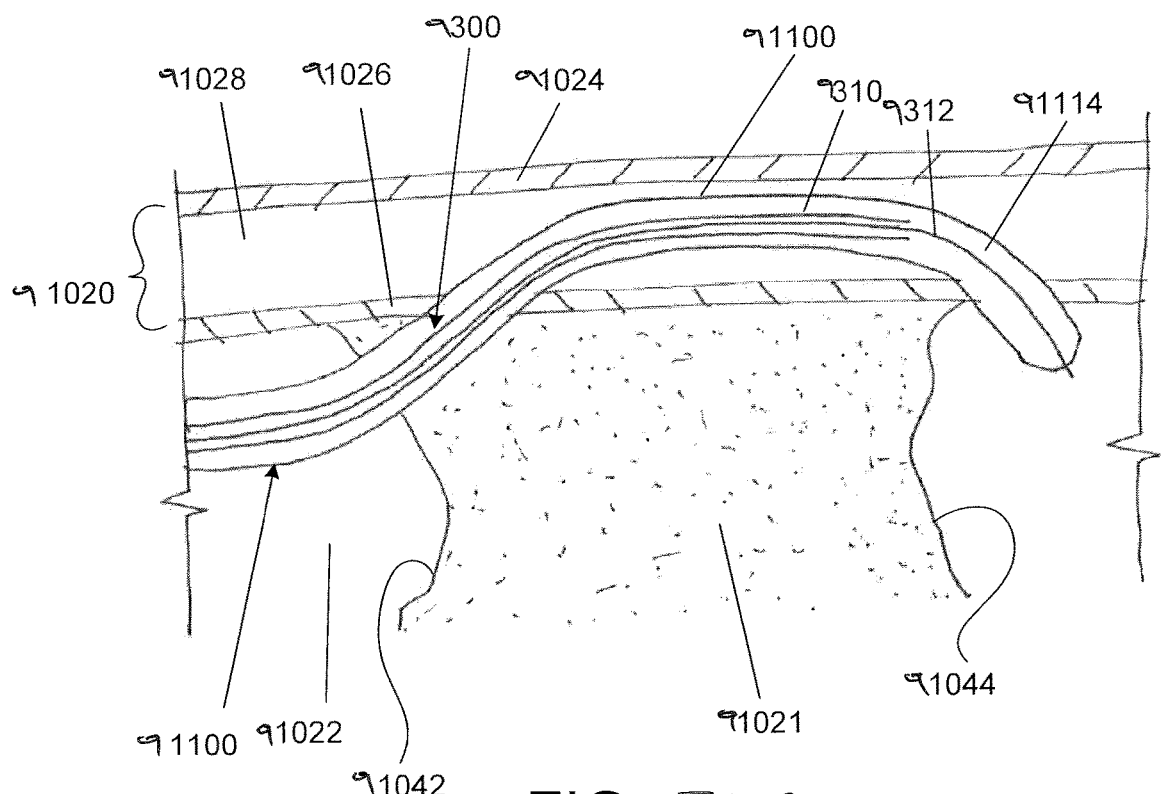
Figure 56D:
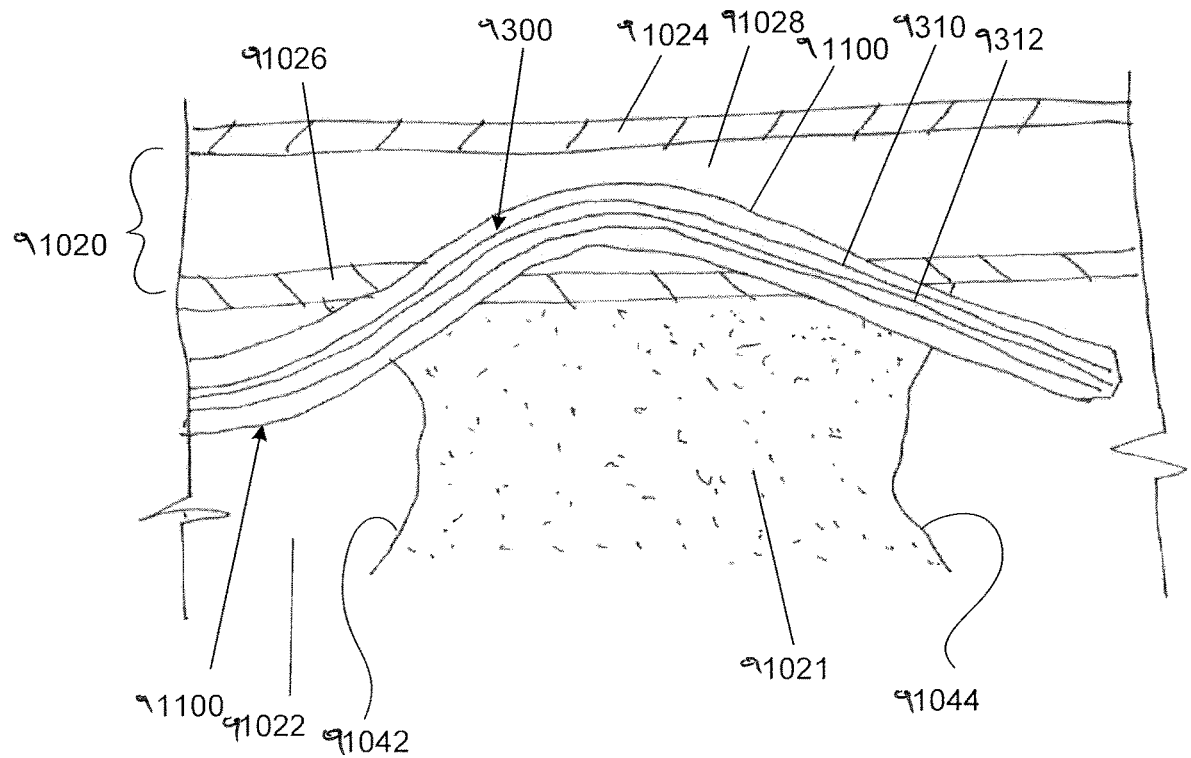

FIGS. 56A-56D show a stylet 9300 used as a re-entry tool for an occlusion-crossing catheter 91100 that has exited the true lumen 91022 and entered the subintimal layer (e.g., medial layer 91028). As shown in FIG. 56A, the stylet 9300 can be placed through a guidewire channel of the catheter 91100. The catheter 91100 can have a fixed bend 91114, which can be rotated to point towards the true lumen 91022. Referring to FIG. 56B, the inner elongate body 9312 can then be extended towards the true lumen 91022. Because the fixed bend 91114 has been oriented towards the true lumen 91022, the pointed distal end 9303 will also point towards the true lumen 91022, thereby allowing it to pierce the vessel wall 91020 as it is extended. Referring to FIG. 56, the catheter 91100 can then be advanced over the stylet 9300 back into the true lumen 91022. As shown in FIG. 56, the outer tube 9310 can then be extended within the catheter 91100 such that it straightens the fixed bend 91114. Such straightening of the fixed bend 91114 will point the catheter 91100 more directly down the true lumen 91022. In some embodiments, this process can be used to pass entirely by an occlusion (as shown in FIGS. 56A-56D). In other embodiments, the stylet 9300 can direct the catheter 91100 back into the occlusion at a point between the proximal 91012 and distal 91044 caps, and then the catheter 91100 can be used to finish crossing through the lesion.

In some embodiments, the inner elongate body 9312 can have a pre-set curve that substantially matches the pre-set curve 9514 of the catheter 9500. For example, the inner elongate body 9312 can be made of a shape memory material, such as nitinol, to set the curve. Having this matched curve can advantageously help with re-entry into the true lumen. That is, if the user steers the directionality of the catheter 9500 towards the true lumen, then when the curved inner elongate body 9312 exits, it will curve and be directed towards the true lumen even more than the catheter itself, helping to avoid deflection off of the vessel wall.

In general, a sharp distal tip of any of the stylets described herein may be protected or covered until deployment into tissue. For example, a spring loaded sheath or housing can be pushed distally along the long axis of the tip to expose the sharp tip. For example, as shown in FIGS. 52A and 52B, a stylet 9900 can include a spring-loaded mechanism 9902 on the distal end of a stylet body 9910. Thus, a coiled member 9904 can be configured to extend over the tip 9906 of the stylet, which can be sharp and/or tapered. Referring to FIG. 52A, in the passive mode, i.e. before contacting tissue, the coiled member 9904 can cover the tapered or sharp end of the stylet so that the end is atraumatic in non-targeted areas. Once the location of re-entry is reached, the tip 9906 can be advanced into the tissue, thus activating the spring mechanism (shown in FIG. 52) as the coil compresses and exposes the penetrating tip 9906.

The length of exposed tip 9906 can be controlled by placing the coiled member 9904 in the desired location along the stylet body 9910. Accordingly, the initial length of the tip 9906 that is exposed through the vessel wall or occlusion can be limited by the coiled member 9904, advantageously avoiding over-puncturing and possibly hitting the opposing vessel wall. Further, the pitch of the coiled member 9904 can be chosen based upon the desired spring force required to penetrate or puncture the tissue, such as based upon the type or thickness of the tissue. Once the tip has been pushed fully through, the coiled member 9904 can act as a temporary stop, providing tactile feedback for the user and allowing the user to adjust the angle or orientation of the stylet tip. Additional force can then be placed on the stylet 9900 to push the coiled member 9904 through. Once the proximal end of the coiled member 9904 is fully advanced through the tissue, the coiled member can relax, allowing the stylet 9900 to be in passive mode again as it traverses through the vessel.

Although a coiled member 9904 is shown in FIGS. 52A and 52B, other spring loaded mechanisms 9902 are possible. Advantageously, spring loaded mechanisms 9902 on the stylet can help control depth of penetration and also provide a safer method of controlling re-entry. The spring-loaded mechanism 9902 can be used with a traditional stylet or with any of the stylets described herein.

Figure 50:
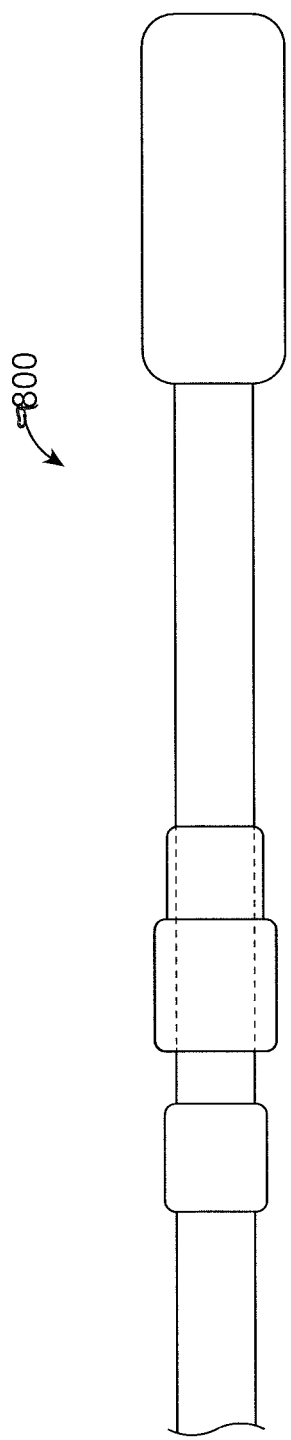
FIG. 50 shows an exemplary manipulator for steering a re-entry stylet.

Referring to FIG. 50, a handle 9800 can be used to steer any of the stylets described herein. The handle 9800 can include a locking mechanism to lock it onto the proximal end of the device, such as a luer fitting. In one embodiment, the handle 9800 can have predefined positions that align the stylet appropriately with the catheter. For example, if the handle 9800 is used with the stylet 9200, the handle can lock the stylet 9200 in a first position where the stylet 9300 is proximal of the bend in the catheter, thereby allowing the main body of the catheter to have extra support. The handle can also lock the stylet 9200 in a second position where the distal stiff section of the stylet 9200 is in the prebent section of the catheter, thereby straightening the catheter. Finally, the handle 9800 can lock the stylet 9200 in a third position where the distal part of the stylet 9200 sticks out of the distal tip of the catheter, thereby enabling re-entry into the true lumen. The handle 9800 can include similar predefined positions when used with the other stylets described in here.

Figure 51A:
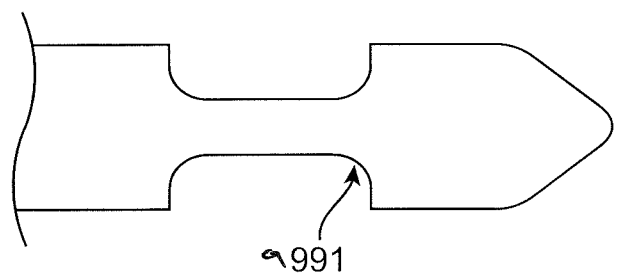
FIG. 51A shows an exemplary stylet tip having a hook anchoring mechanism.
Figure 51B:
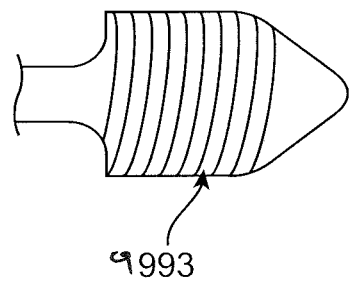
FIG. 51B shows an exemplary stylet tip having a drill anchoring mechanism.

Any of the embodiments of stylets herein can include an anchoring mechanism on or near the distal tip. For example, the distal end can include a hook 9991 as shown in FIG. 51A or a drill tip 9993 as shown in FIG. 51B. The anchoring mechanism can anchor the stylet in a particular location where re-entry is desired, i.e., can prevent proximal movement, and then can be dislodged as the stylet is advanced distally past the location.

Any of the stylets described herein can include a marker, such as a radiopaque marker, to help identify the location of the stylet in situ with imaging. For example, referring to the stylet 9100 of FIGS. 43A-44C, the connector 9106 between the proximal portion 9101 and the middle portion 9102 can form the radiopaque marker. In some embodiments, a radiopaque coating, such as platinum, can be applied to portions of the stylet 9100.

Any of the stylets described herein can include a torquer configured to be tightened onto the stylet for rotational control. In some embodiments, the torquer can be aligned with a particular angle in the stylet. For example, the torquer can align with one or more of the angles of the s-curve 9107 of the stylet 9100.

Any of the stylets described herein can be sized and configured to fit within a guidewire channel of a catheter, such as through a guidewire channel of an occlusion-crossing device. Such exemplary occlusion-crossing devices are described, for example, in U.S. Patent Applications: U.S. Pat. No. 9,125,562, titled "CATHETER- BASED OFF-AXIS OPTICAL COHERENCE TOMOGRAPHY IMAGING SYSTEM," filed Jul. 1, 2010, U.S. Pat. No. 8,644,913, titled "OCCLUSION-CROSSING DEVICES, IMAGING, AND ATHERECTOMY DEVICES," filed Mar. 28, 2012, International Patent Application titled "OCCLUSION-CROSSING DEVICES," filed herewith; and International Patent Application titled "CHRONIC TOTAL OCCLUSION CROSSING DEVICES WITH IMAGING," filed herewith, all of which are incorporated by reference in their entireties.

Further, any of the stylets and/or catheters described herein can be oriented, directed, or steered using image guidance, such as optical coherence tomography, ultrasound, radiofrequency imaging, or fluoroscopy.

It should be understood that any of the features described herein with respect to one embodiment may be substituted for or combined with the features described with respect to another embodiment.

Described herein are devices, including at least some specific exemplary devices, in which dimensions are provided. It is to be understood that these dimensions may be varied while staying within the scope of the invention as generally described. Thus, these figures may not be shown to scale. Unless otherwise indicated, these dimensions are intended as merely illustrative, and not limiting.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

We claim:

1. An atherectomy catheter device configured to visualize and cut tissue, the device comprising:
   an elongate catheter body having a side opening therein;
   a cutter configured to rotate relative to the elongate catheter body;
   a cutter drive shaft within the elongate catheter body and configured to rotate the cutter, wherein the cutter drive shaft is further configured to be longitudinally displaced to expose a distal cutting edge of the cutter through the side opening; and
   an optical fiber extending a length of the elongate catheter body within the cutter drive shaft, a distal end of the optical fiber attached to the cutter and configured to rotate therewith.

2. The atherectomy catheter device of claim 1, further comprising a distal tip attached to the elongate catheter body and configured to collect tissue cut by the cutter.

3. The atherectomy catheter device of claim 2, further comprising a tissue packer configured to push or pull tissue within the distal tip.

4. The atherectomy catheter device of claim 3, wherein the tissue packer is a plunger.

5. The atherectomy catheter device of claim 1, wherein the distal end of the optical fiber is configured to image through the side opening as the cutter rotates.

6. The atherectomy catheter device of claim 1, wherein in the optical fiber is part of an optical coherence tomography (OCT) imaging system.

7. The atherectomy catheter device of claim 1, wherein the cutter comprises a ring cutter.

8. The atherectomy catheter device of claim 1, wherein the distal cutting edge is serrated.

9. The atherectomy catheter device of claim 1, further comprising a mirror to deflect light from the distal end of the optical fiber into the tissue.

10. The atherectomy catheter device of claim 1, wherein the cutter drive shaft is configured to rotate the cutter at between about 200 and 5,000 RPM.

\* \* \* \* \*